(12) United States Patent
Maliga et al.

(10) Patent No.: US 6,987,215 B1
(45) Date of Patent: Jan. 17, 2006

(54) TRANSLATION CONTROL ELEMENTS FOR HIGH-LEVEL PROTEIN EXPRESSION IN THE PLASTIDS OF HIGHER PLANTS AND METHODS OF USE THEREOF

(75) Inventors: Pal Maliga, East Brunswick, NJ (US); Hiroshi Kuroda, Highland Park, NJ (US); Muhammad Sarwar Khan, Orlando, FL (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/762,105

(22) PCT Filed: Aug. 3, 1999

(86) PCT No.: PCT/US99/17806

§ 371 (c)(1),
(2), (4) Date: Apr. 23, 2001

(87) PCT Pub. No.: WO00/07431

PCT Pub. Date: Feb. 17, 2000

Related U.S. Application Data

(60) Provisional application No. 60/095,163, filed on Aug. 3, 1998, provisional application No. 60/095,167, filed on Aug. 3, 1998, provisional application No. 60/112,257, filed on Dec. 15, 1998, provisional application No. 60/131,611, filed on Apr. 29, 1999, and provisional application No. 60/138,764, filed on Jun. 11, 1999.

(51) Int. Cl.
*C12N 15/82* (2006.01)
*A01H 5/00* (2006.01)

(52) U.S. Cl. .................. 800/298; 435/320.1; 536/24.1
(58) Field of Classification Search .............. 435/320.1; 536/24.1; 800/298
See application file for complete search history.

(56) References Cited

U.S. PATENT DOCUMENTS

| 5,122,457 A | | 6/1992 | Reim et al. | |
|---|---|---|---|---|
| 5,451,513 A | | 9/1995 | Maliga et al. | |
| 5,627,061 A | * | 5/1997 | Barry et al. | ................. 800/288 |
| 5,877,402 A | * | 3/1999 | Maliga et al. | ............... 800/298 |
| 6,271,444 B1 | * | 8/2001 | McBride et al. | ............ 800/300 |

OTHER PUBLICATIONS

Jefferson, 1993, GenBank Accession No. A00196.*
Svab et al, 1993, Proc. Natl. Acad. Sci. USA 90:913–917.*
Kendrew, J. The encyclopedia of molecular biology, 1994, Blackwell Science, Oxford, see p. 485.*
Svab, Z. et al., "High Frequency plastid transformation in tobacco by selection for a chimeric aadA gene"; Proc. Natl. Acad. Sci. USA, 90: 913–97 (1993).

Twell, D. et al., "Promoter analysis of genes that are coordinately expressed during pollen development reveals pollen–specific enhancer sequences and shared regulatory elements"; Genes & Development 5: 496–507 (1991).

Cress, W.D. et al., "Critical Structural Elements of the VP16 Transcriptional Activation Domain"; Reports, 251: 87–90 (1991).

Chen, W. et al., "Distinguishing between Mechanisms of Eukaryotic Transcriptional Activation with Bacteriophage T7 RNA Polymerase"; Cell, 50: 1047–1055 (1987).

Kim, M. et al., "Identification of a Sequence–Specific DNA Binding Factor Required for Transcription of the Barley Chloroplast Blue Light–Responsive psbD–psbC Promoter"; The Plant Cell, 7: 1445–1457 (1995).

Lerbes–Mache, S., "The 110–kDa polypeptide of spinach plastid DNA–dependent RNA polymerase: Single–subunit enzyme or catalytic core of multimeric enzyme complexes?"; Proc. Natl. Acad. Sci. USA, 90: 5509–5513 (1993).

Kapoor, S. et al., "Identification and functional significance of a new class of non–consensus–type plastid promoters"; The EMBO Journal, 11(2): 327–337 (1997).

Vera, A. et al., "A ribosomal protein gene (rpl32) from tobacco chloroplast DNA is transcribed from alternative promoters: similarities in promoter region organization in plastid housekeeping genes"; Mol Gen Genet, 251: 518–525 (1996).

Clarke, A.K. et al., "Identification and expression of the chloroplast clpP gene in the conifer *Pinus contorta*"; Plant Molecular Biology, 26: 851–862 (1994).

Huang, C. et al., "The *Chlamydomonas* chloroplast clpP gene contains translated large insertion sequences and is essential for cell growth"; Mol Gen Genet, 244: 151–159 (1994).

Inada, H. et al., "The Existence of three regulatory regions each containing a highly conserved motif in the promoter of plastid–encoded RNA polymerase gene (rpoB)"; The Plant Journal, 11(4): 883–890 (1997).

Jefferson, R.A., NCBI GenBank Accession No. A00196 (1993).

* cited by examiner

*Primary Examiner*—Anne Kubelik
(74) *Attorney, Agent, or Firm*—Dann, Dorman, Herrell & Skillman

(57) ABSTRACT

DNA constructs containing translational control elements are provided. These 5' regulatory segments facilitate high level expression of transgenes introduced into the plastids of higher plants.

12 Claims, 49 Drawing Sheets

(1 of 49 Drawing Sheet(s) Filed in Color)

```
T7g10 mRNA         AUGGCUAGCAUGACUGGUGGACAGCAAAUGGGUCGCGGAUCCGGCUGCUA
                    |   |||||  | ••••|   |  ||
         Ec ADB   3'-GGGUCAGUACUUAGUGUUUCACCAUU-5'   (15)

NheI
T7g10+DB/Ec mRNA    AUGGCaAGCAUGACUGGUGGACAGgcuagc
                     ||  ||•| •  ||      ||•|
         pt ADB   3'-AGGUCAGUGAUCGGGACGGAAGCCGU-5'   (13)

NheI
T7g10+DB/pt mRNA    AUGGCaAucacuagcccugccuuGgcuagc
                     ||  ||||||||||||||||| •|
         pt ADB   3'-AGGUCAGUGAUCGGGACGGAAGCCGU-5'   (21)

NheI            neo
T7g10-DB mRNA       ACAUAUGgcuagcauugaacaagauggauugcau
                    |  | •|||||  •||      | ••
         pt ADB   3'-AGGUCAGUGAUCGGGACGGAAGCCGU-5'   (14)
```

Figure 2B

PrrnLatpB+DBwt (pHK10)
```
        SacI
    1   gagctcGCTC CCCCGCCGTC GTTCAATGAG AATGGATAAG AGGCTCGTGG
                                                  •
   51   GATTGACGTG AGGGGGCAGG GATGGCTATA TTTCTGGGAG AATTAACCGA 101   TCGACGTGCa AGCGGACATT TATTTTaAAT TCGATAATTT TTGCAAAAAC 151   ATTTCGACAT ATTTATTTAT TTTATTATTA TGAGAATCAA TCCTACTACT
                                                  NheI
  201   TCTGGTTCTG GGGTTTCCAC Ggctagc
```

PrrnLatpB-DB (pHK11)
```
        SacI
    1   gagctcGCTC CCCCGCCGTC GTTCAATGAG AATGGATAAG AGGCTCGTGG
                                                  •
   51   GATTGACGTG AGGGGGCAGG GATGGCTATA TTTCTGGGAG AATTAACCGA 101   TCGACGTGCa AGCGGACATT TATTTTaAAT TCGATAATTT TTGCAAAAAC
                                                  NheI
  151   ATTTCGACAT ATTTATTTAT TTTATTATTA TGAGAgctag c
```

PrrnLatpB+DBm (pHK50)
```
        SacI
    1   gagctcGCTC CCCCGCCGTC GTTCAATGAG AATGGATAAG AGGCTCGTGG
                                                  •
   51   GATTGACGTG AGGGGGCAGG GATGGCTATA TTTCTGGGAG AATTAACCGA 101   TCGACGTGCa AGCGGACATT TATTTTaAAT TCGATAATTT TTGCAAAAAC 151   ATTTCGACAT ATTTATTTAT TTTATTATTA TGAGAATaAA cCCgACaACa
                                                  NheI
  201   ..agTGGaagTG GGGTgTCCAC Ggctagc
```

PrrnLclpP+DBwt (pHK12)
```
        SacI                                      •
    1   gagctcGCTC CCCCGCCGTC GTTCAATGAG AATGGATAAG AGGCTCGTGG

51   GATTGACGTG AGGGGGCAGG GATGGCTATA TTTCTGGGAG TTACGTTTCC

101   ACCTCAAAGT GAAATATAGT ATTTAGTTCT TTCTTTCATT TAATGCCTAT
                                                  NheI
  151   TGGTGTTCCA AAAGTCCCTT TCCGAAGTCC TGGAGAGGAA gctagc
```

PrrnLclpP-DB (pHK13)
```
        SacI                                      •
    1   gagctcGCTC CCCCGCCGTC GTTCAATGAG AATGGATAAG AGGCTCGTGG 51   GATTGACGTG AGGGGGCAGG GATGGCTATA TTTCTGGGAG TTACGTTTCC
                                                  NheI
  101   ACCTCAAAGT GAAATATAGT ATTTAGTTCT TTCTTTCATT TAATGCCTgc 151   tagc
```

Figure 3A

PrrnLrbcL+DBwt (pHK14)
     SacI
   1 gagctcGCTC CCCCGCCGTC GTTCAATGAG AATGGATAAG AGGCTCGTGG
                                                        •
  51 GATTGACGTG AGGGGGCAGG GATGGCTATA TTTCTGGGAG TCGAGTAGAC
 101 CTTGTTGTTG TGAaAATTCT TAATTCATGA GTTGTAGGGA GGGATTTATG
                                                   NheI
 151 TCACCACAAA CAGAGACTAA AGCAAGTGTT GGATTCAAAg ctagc

PrrnLrbcL-DB (pHK15)
     SacI
   1 gagctcGCTC CCCCGCCGTC GTTCAATGAG AATGGATAAG AGGCTCGTGG
                                                        •
  51 GATTGACGTG AGGGGGCAGG GATGGCTATA TTTCTGGGAG TCGAGTAGAC
 101 CTTGTTGTTG TGAaAATTCT TAATTCATGA GTTGTAGGGA GGGATTTATG
             NheI
 151 TCAgctagc

PrrnLrbcL+DBm (pHK54)
     SacI
   1 gagctcGCTC CCCCGCCGTC GTTCAATGAG AATGGATAAG AGGCTCGTGG
                                                        •
  51 GATTGACGTG AGGGGGCAGG GATGGCTATA TTTCTGGGAG TCGAGTAGAC
 101 CTTGTTGTTG TGAaAATTCT TAATTCATGA GTTGTAGGGA GGGATTTATG
                                                   NheI
 151 aguCCuCAgA CAGAaACaAA AGCcucaGTa GGATTCAAAg ctagc

PrrnLpsbB+DBwt (pHK16)
     SacI                                               •
   1 gagctcGCTC CCCCGCCGTC GTTCAATGAG AATGGATAAG AGGCTCGTGG
  51 GATTGACGTG AGGGGGCAGG GATGGCTATA TTTCTGGGAG CAATGCAATA
 101 AAGTTACGTA GTGTCTATTT ATCTTTGATA TAAGGGGTAT TTCCATGGGT
                                                   NheI
 151 TTGCCTTGGT ATCGTGTTCA TACCGTTGTA TTGAATGATg ctagc

PrrnLpsbB-DB (pHK17)
     SacI                                               •
   1 gagctcGCTC CCCCGCCGTC GTTCAATGAG AATGGATAAG AGGCTCGTGG
  51 GATTGACGTG AGGGGGCAGG GATGGCTATA TTTCTGGGAG CAATGCAATA
                                                   NcoI NheI
 101 AAGTTACGTA GTGTCTATTT ATCTTTGATA TAAGGGGTAT TTccatggct
 151 agc

Figure 3B

PrrnLpsbA+DBwt (pHK21)
    SacI
  1 gagctcGCTC CCCCGCCGTC GTTCAATGAG AATGGATAAG AGGCTCGTGG
 51 GATTGACGTG AGGGGGCAGG GATGGCTATA TTTCTGGGA•A AAAAGCCTTC
101 CATTTTCTAT TTTGATTTGT AGAAAACTAG TGTGCTTGGG AGTCCCTGAT
                                                    NheI
151 GATTAAATAA ACCAAGATTT TACCATGACT GCAATTTTAG AGAGgctag
201 c

PrrnLpsbA-DB (pHK22)
    SacI
  1 gagctcGCTC CCCCGCCGTC GTTCAATGAG AATGGATAAG AGGCTCGTGG
 51 GATTGACGTG AGGGGGCAGG GATGGCTATA TTTCTGGGA•A AAAAGCCTTC
101 CATTTTCTAT TTTGATTTGT AGAAAACTAG TGTGCTTGGG AGTCCCTGAT
                                     NcoI NheI
151 GATTAAATAA ACCAAGATTT TAccatggct agc

PrrnLpsbA-DB(+GC) (pHK23)
    SacI
  1 gagctcGCTC CCCCGCCGTC GTTCAATGAG AATGGATAAG AGGCTCGTGG
 51 GATTGACGTG AGGGGGCAGG GATGGCTATA TTTCTGGGA•G CAAAAAGCCT
101 TCCATTTTCT ATTTTGATTT GTAGAAAACT AGTGTGCTTG GGAGTCCCTG
                                                NcoI NheI
151 ATGATTAAAT AAACCAAGAT TTTAccatgg ctagc

Figure 3C

PrrnLT7g10+DB/Ec (pHK18)
     SacI
  1  gagctcGCTC CCCCGCCGTC GTTCAATGAG AATGGATAAG AGGCTCGTGG
                                              •
 51  GATTGACGTG AGGGGGCAGG GATGGCTATA TTTCTGGGAG GGAGACCACA
101  ACGGTTTCCC aCTAGAAATA ATTTTGTTTA ACTTTAAGAA GGAGATATAC
                                                 NheI
151  ATATGGCaAG CATGACTGGT GGACAGgcta gc

PrrnLT7g10+DB/pt (pHK19)
     SacI
  1  gagctcGCTC CCCCGCCGTC GTTCAATGAG AATGGATAAG AGGCTCGTGG
                                              •
 51  GATTGACGTG AGGGGGCAGG GATGGCTATA TTTCTGGGAG GGAGACCACA
101  ACGGTTTCCC aCTAGAAATA ATTTTGTTTA ACTTTAAGAA GGAGATATAC
                                                 NheI
151  ATATGGCaAt cactagccct gccttGgcta gc

PrrnLT7g10-DB (pHK20)
     SacI
  1  gagctcGCTC CCCCGCCGTC GTTCAATGAG AATGGATAAG AGGCTCGTGG
                                              •
 51  GATTGACGTG AGGGGGCAGG GATGGCTATA TTTCTGGGAG GGAGACCACA
101  ACGGTTTCCC aCTAGAAATA ATTTTGTTTA ACTTTAAGAA GGAGATATAC
         NheI
151  ATATGgctag c

Figure 3D

PCR-1
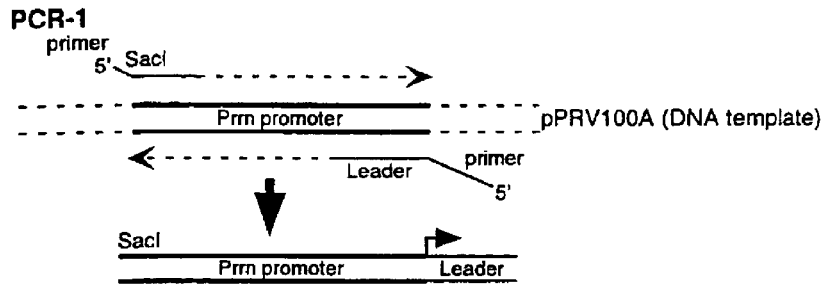
PCR-2: Construct with wild-type DB (DBwt)
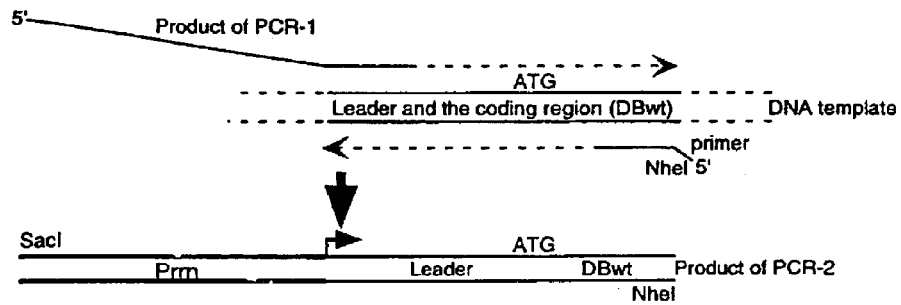
PCR-3: Construct without DB
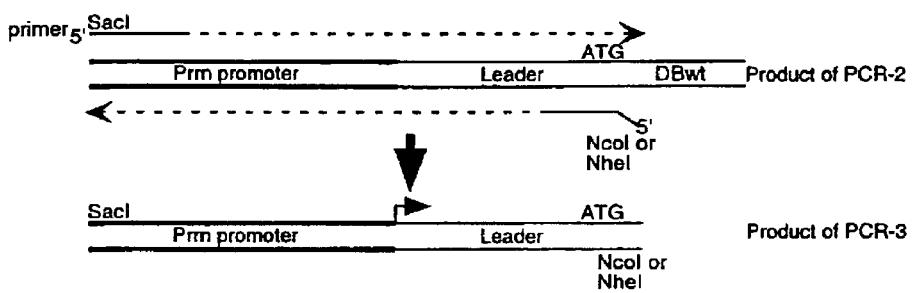
PCR-4: Construct with mutant DB (DBm)
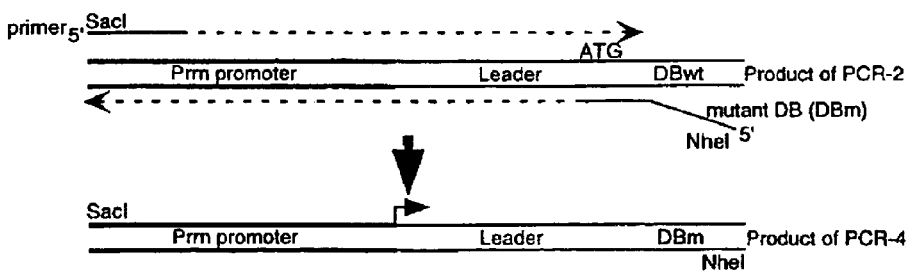
Figure 5

```
        SacI
   1    gagctcggta cccaaaGCTC CCCCGCCGTC GTTCAATGAG AATGGATAAG
  51    AGGCTCGTGG GATTGACGTG AGGGGGCAGG GATGGCTATA TTTCTGGGAG
                                                              NcoI
 101    CGAACTCCGG GCGAATAcGA AGCGCtTGGA TACAGTTGTA GGGAGGGATc
             NheI
 151    catggctagc ATTGAACAAG ATGGATTGCA CGCAGGTTCT CCGGCCGCTT
 201    GGGTGGAGAG GCTATTCGGC TATGACTGGG CACAACAGAC AATCGGCTGC
 251    TCTGATGCCG CCGTGTTCCG GCTGTCAGCG CAGGGGCGCC CGGTTCTTTT
 301    TGTCAAGACC GACCTGTCCG GTGCCCTGAA TGAACTCCAG GACGAGGCAG
 351    CGCGGCTATC GTGGCTGGCC ACGACGGGCG TTCCTTGCGC AGCTGTGCTC
 401    GACGTTGTCA CTGAAGCGGG AAGGGACTGG CTGCTATTGG GCGAAGTGCC
 451    GGGGCAGGAT CTCCTGTCAT CTCACCTTGC TCCTGCCGAG AAAGTATCCA
 501    TCATGGCTGA TGCAATGCGG CGGCTGCATA CGCTTGATCC GGCTACCTGC
 551    CCATTCGACC ACCAAGCGAA ACATCGCATC GAGCGAGCAC GTACTCGGAT
 601    GGAAGCCGGT CTTGTCGATC AGGATGATCT GGACGAAGAG CATCAGGGGC
 651    TCGCGCCAGC CGAACTGTTC GCCAGGCTCA AGGCGCGCAT GCCCGACGGC
 701    GAGGATCTCG TCGTGACACA TGGCGATGCC TGCTTGCCGA ATATCATGGT
 751    GGAAAATGGC CGCTTTTCTG GATTCATCGA CTGTGGCCGG CTGGGTGTGG
 801    CGGACCGCTA TCAGGACATA GCGTTGGCTA CCCGTGATAT TGCTGAAGAG
 851    CTTGGCGGCG AATGGGCTGA CCGCTTCCTC GTGCTTTACG GTATCGCCGC
 901    TCCCGATTCG CAGCGCATCG CCTTCTATCG CCTTCTTGAC GAGTTCTTCT
             XbaI
 951    GAgcgggtct agagtAGACA TTAGCAGATA AATTAGCAGG AAATAAAGAA
1001    GGATAAGGAG AAAGAACTCA AGTAATTATC CTTCGTTCTC TTAATTGAAT
1051    TGCAATTAAA CTCGGCCCAA TCTTTTACTA AAAGGATTGA GCCGAATACA
1101    ACAAAGATTC TATTGCATAT ATTTGACTA AGTATATACT TACCTAGATA
                                             HindIII
1151    TACAAGATTT GAAATACAAA ATCTAGcaag ctt
```

Figure 9

Figure 12 atpB wt

| | AUG Met | AGA Arg | AUC Ile | AAU Asn | CCU Pro | ACU Thr | ACU Thr | UCU Ser | GGU Gly | UCU Ser | GGG Gly | GUU Val | UCC Ser | ACG Thr |
|---|---|---|---|---|---|---|---|---|---|---|---|---|---|---|
| Fraction | 1.0 | 0.22 | 0.27 | 0.61 | 0.30 | 0.37 | 0.37 | 0.31 | 0.38 | 0.31 | 0.26 | 0.35 | 0.14 | 0.15 |
| Triplet/1000 | 24.6 | 7.8 | 15.5 | 18.1 | 13.5 | 18.4 | 18.4 | 20.2 | 28.2 | 20.2 | 19.2 | 24.9 | 9.1 | 7.5 | atpB m

| | AUG Met | AGA Arg | AUa Ile | AAc Asn | CCg Pro | ACa Thr | ACU Thr | UCU Ser | Gga Gly | agU Ser | GGG Gly | GUg Val | UCC Ser | ACG Thr |
|---|---|---|---|---|---|---|---|---|---|---|---|---|---|---|
| Fraction | 1.0 | 0.22 | 0.29 | 0.39 | 0.30 | 0.23 | 0.23 | 0.14 | 0.24 | 0.14 | 0.26 | 0.21 | 0.14 | 0.15 |
| Triplet/1000 | 24.6 | 7.8 | 16.6 | 11.4 | 13.2 | 11.7 | 11.7 | 9.3 | 17.9 | 9.3 | 19.2 | 15.3 | 9.1 | 7.5 | rbcL wt

| | AUG Met | UCA Ser | CCA Pro | CAA Gln | ACA Thr | GAG Glu | ACU Thr | AAA Lys | GCA Ala | AGU Ser | GUU Val | GGA Gly | UUC Phe | AAA Lys |
|---|---|---|---|---|---|---|---|---|---|---|---|---|---|---|
| Fraction | 1.0 | 0.21 | 0.24 | 0.57 | 0.23 | 0.38 | 0.37 | 0.60 | 0.29 | 0.14 | 0.35 | 0.24 | 0.40 | 0.60 |
| Triplet/1000 | 24.6 | 13.5 | 10.6 | 21.0 | 11.7 | 12.4 | 18.4 | 22.0 | 18.1 | 9.3 | 24.9 | 17.9 | 22.5 | 22.0 | rbcL m

| | AUG Met | agu Ser | CCu Pro | CAg Gln | ACA Thr | GAa Glu | ACa Thr | AAA Lys | GCc Ala | uca Ser | GUa Val | GGA Gly | UUC Phe | AAA Lys |
|---|---|---|---|---|---|---|---|---|---|---|---|---|---|---|
| Fraction | 1.0 | 0.14 | 0.30 | 0.43 | 0.23 | 0.62 | 0.23 | 0.60 | 0.16 | 0.21 | 0.31 | 0.24 | 0.40 | 0.60 |
| Triplet/1000 | 24.6 | 9.3 | 13.5 | 15.5 | 11.7 | 20.7 | 11.7 | 22.0 | 10.1 | 13.5 | 21.8 | 17.9 | 22.5 | 22.0 |

T7g10+DB/Ec

| | AUG Met | GCa Ala | AGC Ser | AUG Met | ACU Thr | GGU Gly | GGA Gly | CAG Gln | gcu Ala | agc Ser | auu Ile | gaa Glu | caa Gln | gau Asp |
|---|---|---|---|---|---|---|---|---|---|---|---|---|---|---|
| Fraction | 1.0 | 0.29 | 0.07 | 1.00 | 0.37 | 0.38 | 0.24 | 0.43 | 0.39 | 0.07 | 0.45 | 0.62 | 0.57 | 0.75 |
| Triplet/1000 | 24.6 | 18.1 | 4.7 | 24.6 | 18.4 | 28.2 | 17.9 | 15.5 | 24.4 | 4.7 | 25.9 | 20.7 | 21.0 | 24.6 |

T7g10+DB/pt

| | AUG Met | GCa Ala | Auc Ile | acu Thr | agc Ser | ccu Pro | gcc Ala | uuG Leu | gcu Ala | agc Ser | auu Ile | gaa Glu | caa Gln | gau Asp |
|---|---|---|---|---|---|---|---|---|---|---|---|---|---|---|
| Fraction | 1.0 | 0.29 | 0.27 | 0.37 | 0.07 | 0.07 | 0.16 | 0.24 | 0.39 | 0.07 | 0.45 | 0.62 | 0.57 | 0.75 |
| Triplet/1000 | 24.6 | 18.1 | 15.5 | 18.4 | 4.7 | 4.7 | 10.1 | 34.7 | 24.4 | 4.7 | 25.9 | 20.7 | 21.0 | 24.6 |

T7g10-DB

| | AUG Met | gcu Ala | agc Ser | auu Ile | gaa Glu | caa Gln | gau Asp | gga Gly | uug Leu | cac His | gca Ala | ggu Gly | ucu Ser | ccg Pro |
|---|---|---|---|---|---|---|---|---|---|---|---|---|---|---|
| Fraction | 1.0 | 0.39 | 0.07 | 0.45 | 0.62 | 0.57 | 0.75 | 0.24 | 0.24 | 0.28 | 0.29 | 0.38 | 0.31 | 0.30 |
| Triplet/1000 | 24.6 | 24.4 | 4.7 | 25.9 | 20.7 | 21.0 | 24.6 | 17.9 | 34.7 | 9.1 | 18.1 | 28.2 | 20.2 | 13.2 |

```
NcoI
CCATGgcaccacaaacagagAGCCCAGAACGACGCCCGGCCGACATCCGCCGTGCCACCG
---------+---------+---------+---------+---------+---------+  60
GGTACcgtggtgtttgtctcTCGGGTCTTGCTGCGGGCCGGCTGTAGGCGGCACGGTGGC
     M  A  P  Q  T  E  S  P  E  R  R  P  A  D  I  R  R  A  T  E AGGCGGACATGCCGGCGGTCTGCACCATCGTCAACCACTACATCGAGACAAGCACGGTCA
---------+---------+---------+---------+---------+---------+ 120
TCCGCCTGTACGGCCGCCAGACGTGGTAGCAGTTGGTGATGTAGCTCTGTTCGTGCCAGT
   A  D  M  P  A  V  C  T  I  V  N  H  Y  I  E  T  S  T  V  N ACTTCCGTACCGAGCCGCAGGAACCGCAGGAGTGGACGGACGACCTCGTCCGTCTGCGGG
---------+---------+---------+---------+---------+---------+ 180
TGAAGGCATGGCTCGGCGTCCTTGGCGTCCTCACCTGCCTGCTGGAGCAGGCAGACGCCC
    F  R  T  E  P  Q  E  P  Q  E  W  T  D  D  L  V  R  L  R  E AGCGCTATCCCTGGCTCGTCGCCGAGGTGGACGGCGAGGTCGCCGGCATCGCCTACGCGG
---------+---------+---------+---------+---------+---------+ 240
TCGCGATAGGGACCGAGCAGCGGCTCCACCTGCCGCTCCAGCGGCCGTAGCGGATGCGCC
     R  Y  P  W  L  V  A  E  V  D  G  E  V  A  G  I  A  Y  A  G GCCCCTGGAAGGCACGCAACGCCTACGACTGGACGGCCGAGTCGACCGTGTACGTCTCCC
---------+---------+---------+---------+---------+---------+ 300
CGGGGACCTTCCGTGCGTTGCGGATGCTGACCTGCCGGCTCAGCTGGCACATGCAGAGGG
    P  W  K  A  R  N  A  Y  D  W  T  A  E  S  T  V  Y  V  S  P CCCGCCACCAGCGGACGGGACTGGGCTCCACGCTCTACACCCACCTGCTGAAGTCCCTGG
---------+---------+---------+---------+---------+---------+ 360
GGGCGGTGGTCGCCTGCCCTGACCCGAGGTGCGAGATGTGGGTGGACGACTTCAGGGACC
    R  H  Q  R  T  G  L  G  S  T  L  Y  T  H  L  L  K  S  L  E AGGCACAGGGCTTCAAGAGCGTGGTCGCTGTCATCGGGCTGCCCAACGACCCGAGCGTGC
---------+---------+---------+---------+---------+---------+ 420
TCCGTGTCCCGAAGTTCTCGCACCAGCGACAGTAGCCCGACGGGTTGCTGGGCTCGCACG
     A  Q  G  F  K  S  V  V  A  V  I  G  L  P  N  D  P  S  V  R GCATGCACGAGGCGCTCGGATATGCCCCCCGCGGCATGCTGCGGGCGGCCGGCTTCAAGC
---------+---------+---------+---------+---------+---------+ 480
CGTACGTGCTCCGCGAGCCTATACGGGGGGCGCCGTACGACGCCCGCCGGCCGAAGTTCG
    M  H  E  A  L  G  Y  A  P  R  G  M  L  R  A  A  G  F  K  H ACGGGAACTGGCATGACGTGGGTTTCTGGCAGCTGGACTTCAGCCTGCCGGTACCGCCCC
---------+---------+---------+---------+---------+---------+ 540
TGCCCTTGACCGTACTGCACCCAAAGACCGTCGACCTGAAGTCGGACGGCCATGGCGGGG
     G  N  W  H  D  V  G  F  W  Q  L  D  F  S  L  P  V  P  P  R
                                           BglII
GTCCGGTCCTGCCCGTCACCGAGATCTGATGAtcgaattcctgcagcccggggggatccac
---------+---------+---------+---------+---------+---------+ 600
CAGGCCAGGACGGGCAGTGGCTCTAGACTACTagcttaaggacgtcgggcccctaggtg
    P  V  L  P  V  T  E  I  *
      XbaI
tagttctaga
---------+ 610
atcaagatct
```

Figure 19

```
NcoI   NheI
CcATGgctAGCCCAGAAaGAaGaCCGGCCGAtATtaGaCGTGCtACaGAaGCtGAtATGC
---------+---------+---------+---------+---------+---------+
ggTACcgaTCGGGTCTTtCTtCtGGCCGGCTaTAatCtGCACGaTGtCTtCGaCTaTACG
    M  A  S  P  E  R  R  P  A  D  I  R  R  A  T  E  A  D  M  P CaGCaGTtTGtACaATtGTtAAtCAtTAtATaGAaACAAGtACcGTaAACTTtcGaACtG
---------+---------+---------+---------+---------+---------+
GtCGtCAaACaTGtTAaCAaTTaGTaATaTAtCTtTGTTCaTGgCATTGAAagCtTGaC
    A  V  C  T  I  V  N  H  Y  I  E  T  S  T  V  N  F  R  T  E AaCCtCAaGAACCtCAaGAaTGGACtGAtGAttTaGTCCGTtTaCGaGAGCGCTATCCtT
---------+---------+---------+---------+---------+---------+
TtGGaGTtCTTGGaGTtCTtACCTGaCTaCTaaAtCAGGCAaAtGCtCTCGCGATAGGaA
    P  Q  E  P  Q  E  W  T  D  D  L  V  R  L  R  E  R  Y  P  W GGCTtGTaGCaGAaGTtGACGGaGAaGTaGCtGGgATtGCaTAtGCGGGCCCgTGGAAaG
---------+---------+---------+---------+---------+---------+
CCGAaCATCGtCTtCAaCTGCCtCTtCATCGaCCtAaCGtATaCGCCCGGGcACCTTtC
    L  V  A  E  V  D  G  E  V  A  G  I  A  Y  A  G  P  W  K  A CAcGaAATGCaTAtGAtTGGACgGCtGAaTCaACtGTgTACGTtTCaCCaCGtCAtCAaC
---------+---------+---------+---------+---------+---------+
GTgCtTTaCGtATaCTaACCTGCCGaCTtAGtTGaCACATGCAaAGtGGtGCaGTaGTtG
    R  N  A  Y  D  W  T  A  E  S  T  V  Y  V  S  P  R  H  Q  R GgACaGGACTtGGtTCtACttTaTATaCCcATCTaCTGAAaTCttTGGAGGCACAgGGtT
---------+---------+---------+---------+---------+---------+
CcTGtCCTGAaCCaAGaTGaaATaTATGgGTaGATGACTTtAGaaACCTCCGTGTCCCaA
    T  G  L  G  S  T  L  Y  T  H  L  L  K  S  L  E  A  Q  G  F TtAAGAGtGTgGTaGCTGTtATaGGatTGCCgAAtGAtCCctcgGTaCGCATGCAcGAaG
---------+---------+---------+---------+---------+---------+
AaTTCTCaCAcCAtCGACAaTATCCtaACGGcTTaCTaGGgagcCATGCGTACGTgCTtC
    K  S  V  V  A  V  I  G  L  P  N  D  P  S  V  R  M  H  E  A CtCTcGGATATGCtCCcaGaGGtATGtTGaGGGCcGCaGGtTTCAAacAtGGaAAtTGGC
---------+---------+---------+---------+---------+---------+
GaGAgCCTATACGaGGgtCtCCaTACaACtCCCGgCGtCCaAAGTTtGTaCCtTTaACCG
    L  G  Y  A  P  R  G  M  L  R  A  A  G  F  K  H  G  N  W  H ATGAtGTaGGTTTtTGGCAaCTtGAcTTCtctttTaCCaGTACCtCCtCGTCCcGTttaC
---------+---------+---------+---------+---------+---------+
TACTaCAtCCAAAaACCGTtGAaCTgAAGagaaAtGGtCATGgAGGaGCAGGgCAaaATG
    D  V  G  F  W  Q  L  D  F  S  L  P  V  P  P  R  P  V  L  P BglII      XbaI
CcGTtACtGAGATCTGATGAtctaga
---------+---------+------
GgCAaTGaCTCTAGACTACTagatct
    V  T  E  I  *  *
```

Figure 20A

```
NcoI   NheI
ccATGgctAGCCCAGAAaGAaGaCCGGCCGAtATtaGaCGTGCtACaGAaGCtGAtATGC
---------+---------+---------+---------+---------+---------+
ggTACcgaTCGGGTCTTtCTtCtGGCCGGCTaTAatCtGCACgaTGtCTtCGaCTaTACG
  M  A  S  P  E  R  R  P  A  D  I  R  R  A  T  E  A  D  M  P CaGCaGTtTGtACaATtGTtAAtCAtTAtATaGAaACAAGtACaGTaAAtTTtcGaACtG
---------+---------+---------+---------+---------+---------+
GtCGtCAaACaTGtTAaCAaTTaGTaATaTAtCTtTGTTCaTGtCAtTTaAAagCttGac
   A  V  C  T  I  V  N  H  Y  I  E  T  S  T  V  N  F  R  T  E AaCCtCAaGAACCtCAaGAaTGGACtGAtGAttTaGTaCGTtTaCGaGAaCGtTATCCtT
---------+---------+---------+---------+---------+---------+
TtGGaGTtCTTGGaGTtCTtACCTGaCTaCTaaAtCAtGCAaAtGCtCTtGCaATAGGaA
   P  Q  E  P  Q  E  W  T  D  D  L  V  R  L  R  E  R  Y  P  W GGCTtGTaGCaGAaGTtGAcGGaGAaGTaGCtGGaATtGCaTAtGCtGGtCCgTGGAAaG
---------+---------+---------+---------+---------+---------+
CCGAaCAtCGtCTtCAaCTgCCtCTtCAtCGaCCtTAacGtATaCGaCCaGGcACCTTtC
   L  V  A  E  V  D  G  E  V  A  G  I  A  Y  A  G  P  W  K  A CAcGaAAtGCaTAtGAtTGGACaGCtGAaTCAaCtGTtTAtGTtTCaCCaCGtCAtCAaC
---------+---------+---------+---------+---------+---------+
GTgCtTTaCGtATaCTaACCTGtCGaCTtAGtTGaCAaATaCAaAGtGGtGCaGTaGTtG
   R  N  A  Y  D  W  T  A  E  S  T  V  Y  V  S  P  R  H  Q  R GtACaGGACTtGGtTCtACttTaTAtACtCAtCTtCTtAAaTCttTGGAaGCACAaGGtT
---------+---------+---------+---------+---------+---------+
CaTGtCCTGAaCCaAGaTGaaATaTAtGaGTaGAaGAaTTtAGaaACCTtCGTGTtCCaA
   T  G  L  G  S  T  L  Y  T  H  L  L  K  S  L  E  A  Q  G  F TtAAaAGtGTaGTaGCTGTtATaGGatTGCCgAAtGAtCCctcaGTaCGCATGCAtGAaG
---------+---------+---------+---------+---------+---------+
AaTTtTCaCAtCAtCGACAaTATCCtaACGGcTTaCTaGGgagtCAtGCGTACGTaCTtC
   K  S  V  V  A  V  I  G  L  P  N  D  P  S  V  R  M  H  E  A CtCTtGGATATGCtCCcaGaGGtATGtTGaGGGCaGCaGGtTTCAAaCAtGGaAAtTGGC
---------+---------+---------+---------+---------+---------+
GaGAaCCTATACGaGGgtCtCCaTACaACtCCCGtCGtCCaAAGTTtGTaCCtTTaACCG
   L  G  Y  A  P  R  G  M  L  R  A  A  G  F  K  H  G  N  W  H ATGAtGTaGGTTTtTGGCAaCTtGAcTTCtcttTaCCaGTACCtCCtCGtCCcGTttTaC
---------+---------+---------+---------+---------+---------+
TACTaCAtCCAAAaACCGTtGAaCTgAAGagaaATGGtCATGGaGGaGCAGGgCAaaAtG
   D  V  G  F  W  Q  L  D  F  S  L  P  V  P  P  R  P  V  L  P BglII      XbaI
CcGTtACtGAGATCTGATGAtctaga
---------+---------+------
GgCAaTGaCTCTAGACTACTagatct
   V  T  E  I  *  *
```

Figure 20B

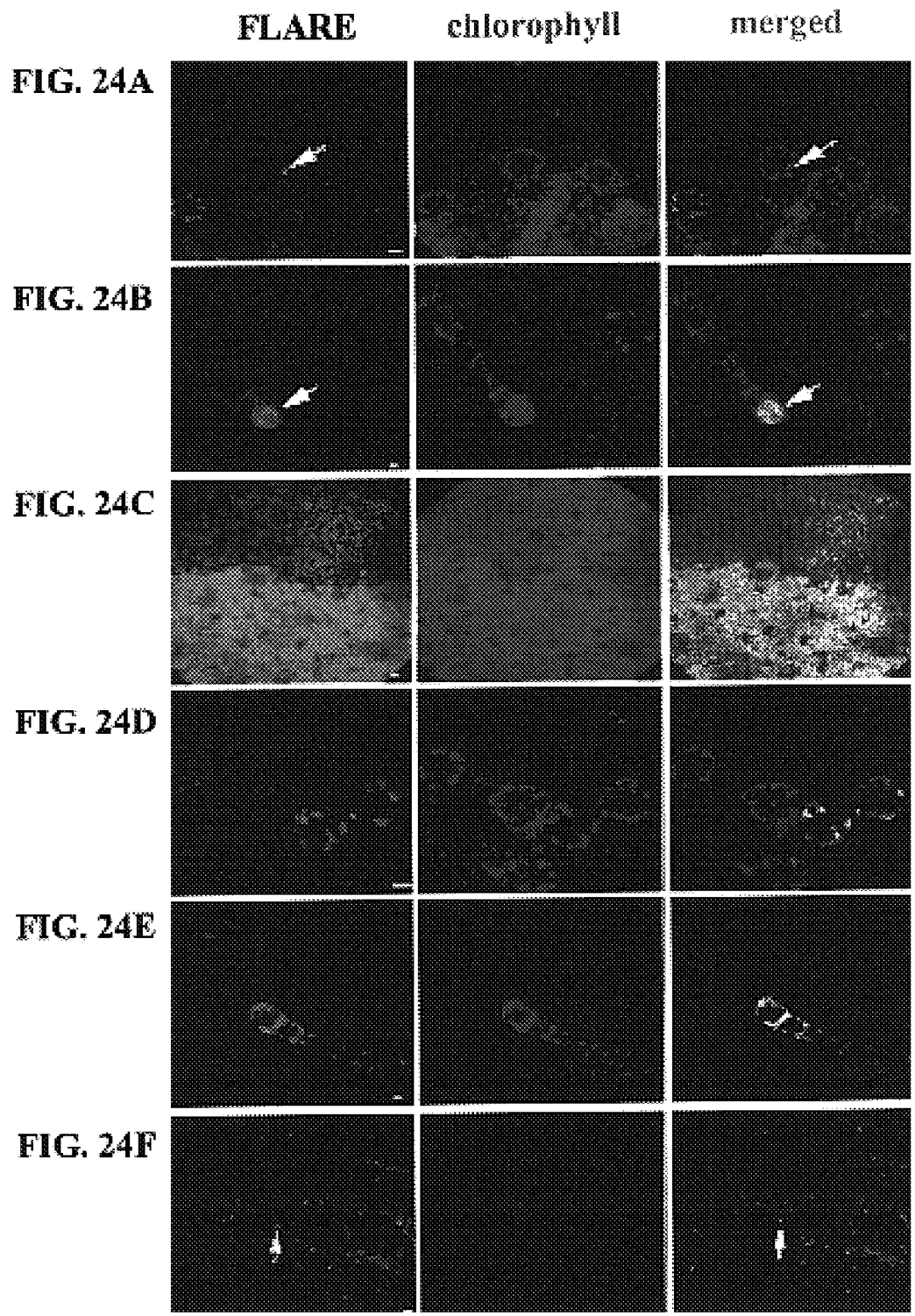

FLARE16-S.seq Length: 1574

NcoI

```
    1 cCATGgGGgc tagcGAAGCG GTGATCGCCG AAGTATCGAC TCAACTATCA
   51 GAGGTAGTTG GCGTCATCGA GCGCCATCTC GAACCGACGT TGCTGGCCGT
  101 ACATTTGTAC GGCTCCGCAG TGGATGGCGG CCTGAAGCCA CACAGTGATA
  151 TTGATTTGCT GGTTACGGTG ACCGTAAGGC TTGATGAAAC AACGCGGCGA
  201 GCTTTGATCA ACGACCTTTT GGAAACTTCG GCTTCCCCTG GAGAGAGCGA
  251 GATTCTCCGC GCTGTAGAAG TCACCATTGT TGTGCACGAC GACATCATTC
  301 CGTGGCGTTA TCCAGCTAAG CGCGAACTGC AATTTGGAGA ATGGCAGCGC
  351 AATGACATTC TTGCAGGTAT CTTCGAGCCA GCCACGATCG ACATTGATCT
  401 GGCTATCTTG CTGACAAAAG CAAGAGAACA TAGCGTTGCC TTGGTAGGTC
  451 CAGCGGCGGA GGAACTCTTT GATCCGGTTC CTGAACAGGA TCTATTTGAG
  501 GCGCTAAATG AAACCTTAAC GCTATGGAAC TCGCCGCCCG ACTGGGCTGG
  551 CGATGAGCGA AATGTAGTGC TTACGTTGTC CCGCATTTGG TACAGCGCAG
  601 TAACCGGCAA AATCGCGCCG AAGGATGTCG CTGCCGACTG GGCAATGGAG
  651 CGCCTGCCGG CCCAGTATCA GCCCGTCATA CTTGAAGCTA GACAGGCTTA
  701 TCTTGGACAA GAAGAAGATC GCTTGGCCTC GCGCGCAGAT CAGTTGGAAG
  751 AATTTGTCCA CTACGTGAAA GGCGAGATCA CCAAGGTAGT GGGCAAAgaa
  801 .cttgttgaag gaaaattgga gctagtagaa ggtcttaaag tcgccATGgc
  851 cAGTAAAGGA GAAGAACTTT TCACTGGAGT TGTCCCAATT CTTGTTGAAT
  901 TAGATGGTGA TGTTAATGGG CACAAATTTT CTGTCAGTGG AGAGGGTGAA
  951 GGTGATGCAA CATACGGAAA ACTTACCCTT AAATTTATTT GCACTACTGG
 1001 AAAACTACCT GTTCCTTGGC CAACACTTGT CACTACTTTC TCTTATGGTG
 1051 TTCAATGCTT TTCAAGATAC CCAGATCATA TGAAGCGGCA CGACTTCTTC
 1101 AAGAGCGCCA TGCCTGAGGG ATACGTGCAG GAGAGGACCA TCTCTTTCAA
 1151 GGACGACGGG AACTACAAGA CACGTGCTGA AGTCAAGTTT GAGGGAGACA
 1201 CCCTCGTCAA CAGGATCGAG CTTAAGGGAA TCGATTTCAA GGAGGACGGA
 1251 AACATCCTCG GCCACAAGTT GGAATACAAC TACAACTCCC ACAACGTATA
 1301 CATCACGGCA GACAAACAAA AGAATGGAAT CAAAGCTAAC TTCAAAATTA
 1351 GACACAACAT TGAAGATGGA AGCGTTCAAC TAGCAGACCA TTATCAACAA
 1401 AATACTCCAA TTGGCGATGG CCCTGTCCTT TTACCAGACA ACCATTACCT
 1451 GTCCACACAA TCTGCCCTTT CGAAAGATCC CAACGAAAAG AGAGACCACA
 1501 TGGTCCTTCT TGAGTTTGTA ACAGCTGCTG GGATTACACA TGGCATGGAT
 1551 GAACTATACA AATAAGgctc taga
```

← aadA

← gfp

XbaI

Figure 28

FLARE16-S1.seq  Length: 1953

```
        SacI
   1  gagctcGCTC CCCCGCCGTC GTTCAATGAG AATGGATAAG AGGCTCGTGG
  51  GATTGACGTG AGGGGGCAGG GATGGCTATA TTTCTGGGAG TCGAGTAGAC
 101  CTTGTTGTTG TGAaAATTCT TAATTCATGA GTTGTAGGGA GGGATTTATG
 151  TCACCACAAA CAGAGACTAA AGCAAGTGTT GGATTCAAAg ctagcAAGC
 201  GGTGATCGCC GAAGTATCGA CTCAACTATC AGAGGTAGTT GGCGTCATCG
 251  AGCGCCATCT CGAACCGACG TTGCTGGCCG TACATTTGTA CGGCTCCGCA
 301  GTGGATGGCG GCCTGAAGCC ACACAGTGAT ATTGATTTGC TGGTTACGGT
 351  GACCGTAAGG CTTGATGAAA CAACGCGGCG AGCTTTGATC AACGACCTTT
 401  TGGAAACTTC GGCTTCCCCT GGAGAGAGCG AGATTCTCCG CGCTGTAGAA
 451  GTCACCATTG TTGTGCACGA CGACATCATT CCGTGGCGTT ATCCAGCTAA
 501  GCGCGAACTG CAATTTGGAG AATGGCAGCG CAATGACATT CTTGCAGGTA
 551  TCTTCGAGCC AGCCACGATC GACATTGATC TGGCTATCTT GCTGACAAAA
 601  GCAAGAGAAC ATAGCGTTGC CTTGGTAGGT CCAGCGGCGG AGGAACTCTT
 651  TGATCCGGTT CCTGAACAGG ATCTATTTGA GGCGCTAAAT GAAACCTTAA
 701  CGCTATGGAA CTCGCCGCCC GACTGGGCTG GCGATGAGCG AAATGTAGTG
 751  CTTACGTTGT CCCGCATTTG GTACAGCGCA GTAACCGGCA AAATCGCGCC
 801  GAAGGATGTC GCTGCCGACT GGGCAATGGA GCGCCTGCCG GCCCAGTATC
 851  AGCCCGTCAT ACTTGAAGCT AGACAGGCTT ATCTTGGACA AGAAGAAGAT
 901  CGCTTGGCCT CGCGCGCAGA TCAGTTGGAA GAATTTGTCC ACTACGTGAA
 951  AGGCGAGATC ACCAAGGTAG TGGGCAAAga acttgttgaa ggaacattgg
1001  agctagtaga aggtcttaaa gtcgccATGg CTAGTAAAGG AGAAGAACTT
1051  TTCACTGGAG TTGTCCCAAT TCTTGTTGAA TTAGATGGTG ATGTTAATGG
1101  GCACAAATTT TCTGTCAGTG GAGAGGGTGA AGGTGATGCA ACATACGGAA
1151  AACTTACCCT TAAATTTATT TGCACTACTG GAAAACTACC TGTTCCttGG
1201  CCAACACTTG TCACTACTTT CTCTTATGGT GTTCAATGCT TTTCAAGATA
1251  CCCAGATCAT ATGAAGCGGC ACGACTTCTT CAAGAGCGCC ATGCCTGAGG
1301  GATACGTGCA GGAGAGGACC ATCTCTTTCA AGGACGACGG GAACTACAAG
1351  ACACGTGCTG AAGTCAAGTT TGAGGGAGAC ACCCTCGTCA ACAGGATCGA
1401  GCTTAAGGGA ATCGATTTCA AGGAGGACGG AAACATCCTC GGCCACAAGT
1451  TGGAATACAA CTACAACTCC CACAACGTAT ACATCACGGC AGACAAACAA
1501  AAGAATGGAA TCAAAGCTAA CTTCAAAATT AGACACAACA TTGAAGATGG
1551  AAGCGTTCAA CTAGCAGACC ATTATCAACA AAATACTCCA ATTGGCGATG
1601  GCCCTGTCCT TTTACCAGAC AACCATTACC TGTCCACACA ATCTGCCCTT
1651  TCGAAAGATC CCAACGAAAA GAGAGACCAC ATGGTCCTTC TTGAGTTTGT
1701  AACAGCTGCT GGGATTACAC ATGGCATGGA TGAACTATAC AAATAAggct
1751  ctagagcAT CCTGGCCTAG TCTATAGGAG GTTTGAAAA GAAAGGAGCA
1801  ATAATCATTT TCTTGTTCTA TCAAGAGGGT GCTATTGCTC CTTTCTTTTT
1851  TTCTTTTTAT TTATTACTA GTATTTTACT TACATAGACT TTTTTGTTTA
1901  CATTATAGAA AAAGAAGGAG AGGTTATTTT CTTGCATTTA TTCATgaaag
1951  ctt
```

Figure 29

FLARE16-S2.seq  Length: 1985

```
          SacI
    1 gagctcGCTC CCCCGCCGTC GTTCAATGAG AATGGATAAG AGGCTCGTGG
   51 GATTGACGTG AGGGGGCAGG GATGGCTATA TTTCTGGGAG AATTAACCGA
  101 TCGACGTGCa AGCGGACATT TATTTTaAAT TCGATAATTT TTGCAAAAAC
  151 ATTTCGACAT ATTTATTTAT TTATTATTA TGAGAATCAA TCCTACTACT
  201 TCTGGTTCTG GGGTTTCCAC GgctagcGAA GCGGTGATCG CCGAAGTATC
  251 CACTCAACTA TCAGAGGTAG TTGGCGTCAT CGAGCGCCAT CTCGAACCGA
  301 CGTTGCTGGC CGTACATTTG TACGGCTCCG CAGTGGATGG CGGCCTGAAG
  351 CCACACAGTG ATATTGATTT GCTGGTTACG GTGACCGTAA GGCTTGATGA
  401 AACAACGCGG CGAGCTTTGA TCAACGACCT TTTGGAAACT TCGGCTTCCC
  451 CTGGAGAGAG CGAGATTCTC CGCGCTGTAG AAGTCACCAT TGTTGTGCAC
  501 GACGACATCA TTCCGTGGCG TTATCCAGCT AAGCGCGAAC TGCAATTTGG
  551 AGAATGGCAG CGCAATGACA TTCTTGCAGG TATCTTCGAG CCAGCCACGA
  601 TCGACATTGA TCTGGCTATC TTGCTGACAA AAGCAAGAGA ACATAGCGTT
  651 GCCTTGGTAG GTCCAGCGGC GGAGGAACTC TTTGATCCGG TTCCTGAACA
  701 GGATCTATTT GAGGCGCTAA ATGAAACCTT AACGCTATGG AACTCGCCGC
  751 CCGACTGGGC TGGCGATGAG CGAAATGTAG TGCTTACGTT GTCCCGCATT
  801 TGGTACAGCG CAGTAACCGG CAAAATCGCG CCGAAGGATG TCGCTGCCGA
  851 CTGGGCAATG GAGCGCCTGC CGGCCCAGTA TCAGCCCGTC ATACTTGAAG
  901 CTAGACAGGC TTATCT GGA CAAGAAGAAG ATCGCTTGGC CTCGCGCGCA
  951 GATCAGTTGG AAGAATTTGT CCACTACGTG AAAGGCGAGA TCACCAAGGT
 1001 AGTGGCAAA gaacttgttg aaggaaaatt ggagctagta gaaggtctta
 1051 aagtcgccAT GgcTAGTAAA GGAGAAGAAC TTTTCACTGG AGTTGTCCCA
 1101 ATTCTTGTTG AATTAGATGG TGATGTTAAT GGGCACAAAT TTTCTGTCAG
 1151 TGGAGAGGGT GAAGGTGATG CAACATACGG AAAACTTACC CTTAAATTTA
 1201 TTTGCACTAC TGGAAAACTA CCTGTTCCtT GGCCAACACT TGTCACTACT
 1251 TTCTCTTATG GTGTTCAATG CTTTTCAAGA TACCCAGATC ATATGAAGCG
 1301 GCACGACTTC TTCAAGAGCG CCATGCCTGA GGGATACGTG CAGGAGAGGA
 1351 CCATCTCTTT CAAGGACGAC GGGAACTACA AGACACGTGC TGAAGTCAAG
 1401 TTTGAGGGAG ACACCCTCGT CAACAGGATC GAGCTTAAGG GAATCGATTT
 1451 CAAGGAGGAC GGAAACATCC TCGGCCACAA GTTGGAATAC AACTACAACT
 1501 CCCACAACGT ATACATCACG GCAGACAAAC AAAAGAATGG AATCAAAGCT
 1551 AACTTCAAAA TTAGACACAA CATTGAAGAT GGAAGCGTTC AACTAGCAGA
 1601 CCATTATCAA CAAAATACTC CAATTGGCGA TGGCCCTGTC CTTTTACCAG
 1651 ACAACCATTA CCTGTCCACA CAATCTGCCC TTTCGAAAGA TCCCAACGAA
 1701 AAGAGAGACC ACATGGTCCT TCTTGAGTTT GTAACAGCTG CTGGGATTAC
 1751 ACATGGCATG GATGAACTAT ACAAATAAGg ctctagagcG ATCCTGGCCT
 1801 AGTCTATAGG AGGTTTTGAA AAGAAGGAG CAATAATCAT TTTCTTGTTC
 1851 TATCAAGAGG GTGCTATTGC TCCTTTCTTT TTTTCTTTTT ATTTATTTAC
 1901 TAGTATTTTA CTTACATAGA CTTTTTTGTT TACATTATAG AAAAGAAGG
 1951 AGAGGTTATT TTCTTGCATT TATTCATGaa agctt
                                   HindIII
```

Figure 30

```
FLARE11-S.seq  Length: 1595
                NcoI            c-Myc
     1  ccatggggc tagcgaacaa aaactcattt ctgaagaaga cttgcctagc
    51  GAAGCGGTGA TCGCCGAAGT ATCGACTCAA CTATCAGAGG TAGTTGGCGT
   101  CATCGAGCGC CATCTCGAAC CGACGTTGCT GGCCGTACAT TTGTACGGCT
   151  CCGCAGTGGT TGGCGGCCTG AAGCCACACA GTGATATTGA TTTGCTGGTT
   201  ACGGTGACCG TAAGGCTTGA TGAAACAACG CGGCGAGCTT TGATCAACGA
   251  CCTTTTGGAA ACTTCGGCTT CCCCTGGAGA GAGCGAGATT CTCCGCGCTG
   301  TAGAAGTCAC CATTGTTGTG CACGACGACA TCATTCCGTG GCGTTATCCA
   351  GCTAAGCGCG AACTGCAATT TGGAGAATGG CAGCGCAATG ACATTCTTGC
   401  AGGTATCTTC GAGCCAGCCA CGATCGACAT TGATCTGGCT ATCTTGCTGA
   451  CAAAAGCAAG AGAACATAGC GTTGCCTTGG TAGGTCCAGC GGCGGAGGAA
   501  CTCTTTGATC CGGTTCCTGA ACAGGATCTA TTTGAGGCGC TAAATGAAAC
   551  CTTAACGCTA TGGAACTCGC CGCCCGACTG GGCTGGCGAT GAGCGAAATG
   601  TAGTGCTTAC GTTGTCCCGC ATTTGGTACA GCGCAGTAAC CGGCAAAATC
   651  GCGCCGAAGG ATGTCGCTGC CGACTGGGCA ATGGAGCGCC TGCCGGCCCA
   701  GTATCAGCCC GTCATACTTG AAGCTAGACA GGCTTATCTT GGACAAGAAG
   751  AAGATCGCTT GGCCTCGCGC GCAGATCAGT TGGAAGAATT TGTCCACTAC
   801  GTGAAAGGCG AGATCACCAA GGTAGTGGGC AAAGaacttg cagttgaagg
   851  aaaattggag gtcgccATGg CTAGTAAAGG AGAAGAACTT TTCACTGGAG
   901  TTGTCCCAAT TCTTGTTGAA TTAGATGGTG ATGTTAATGG CACAAATTT
   951  TCTGTCAGTG GAGAGGGTGA AGGTGATGCA ACATACGGAA AACTTACCCT
  1001  TAAATTTATT TGCACTACTG GAAAACTACC TGTTCCtTGG CCAACACTTG
  1051  TCACTACTTT CTCTTATGGT GTTCAATGCT TTCAAGATA CCCAGATCAT
  1101  ATGAAGCGGC ACGACTTCTT CAAGAGCGCC ATGCCTGAGG GATACGTGCA
  1151  GGAGAGGACC ATCTCTTTCA AGGACGACGG GAACTACAAG ACACGTGCTG
  1201  AAGTCAAGTT TGAGGGAGAC ACCCTCGTCA ACAGGATCGA GCTTAAGGGA
  1251  ATCGATTTCA AGGAGGACGG AAACATCCTC GGCCACAAGT TGGAATACAA
  1301  CTACAACTCC CACAACGTAT ACATCACGGC AGACAAACAA AAGAATGGAA
  1351  TCAAAGCTAA CTTCAAAATT AGACACAACA TTGAAGATGG AAGCGTTCAA
  1401  CTAGCAGACC ATTATCAACA AAATACTCCA ATTGGCGATG CCCTGTCCT
  1451  TTTACCAGAC AACCATTACC TGTCCACACA ATCTGCCCTT TCGAAAGATC
  1501  CCAACGAAAA GAGAGACCAC ATGGTCCTTC TTGAGTTTGT AACAGCTGCT
  1551  GGGATTACAC ATGGCATGGA TGAACTATAC AAATAAggct ctaga
                                                      XbaI
``` aadA (right side label, middle section)
gfp (right side label, lower section)

Figure 31

```
FLARE11-S3.seq  Length: 1961
       SacI
   1  gagctcGCTC CCCCGCCGTC GTTCAATGAG AATGGATAAG AGGCTCGTGG
  51  GATTGACGTG AGGGGGCAGG GATGGCTATA TTTCTGGGAG GGAGACCACA      L Tr910D8
 101  ACGGTTTCCC aCTAGAAATA ATTTTGTTTA ACTTTAAGAA GGAGATATAC
 151  ATATGGCaAG CATGACTGGT GGACAGcta gcgaacaaaa actcatttct
 201  gaagaagact tgcctagcCA AGCGGTGATC GCCGAAGTAT CGACTCAACT
 251  ATCAGAGGTA GTTGGCGTCA TCGAGCGCCA TCTCGAACCG ACGTTGCTGG
 301  CCGTACATTT GTACGGCTCC GCAGTGGATG GCGGCCTGAA GCCACACAGT
 351  GATATTGATT TGCTGGTTAC GGTGACCGTA AGGCTTGATG AAACAACGCG
 401  GCGAGCTTTG ATCAACGACC TTTTGGAAAC TTCGGCTTCC CCTGGAGAGA
 451  GCGAGATTCT CCGCGCTGTA GAAGTCACCA TTGTTGTGCA CGACGACATC
 501  ATTCCGTGGC GTTATCCAGC TAAGCGCGAA CTGCAATTTG GAGAATGGCA
 551  GCGCAATGAC ATTCTTGCAG GTATCTTCGA GCCAGCCACG ATCGACATTG
 601  ATCTGGCTAT CTTGCTGACA AAAGCAAGAG AACATAGCGT TGCCTTGGTA
 651  GGTCCAGCGG CGGAGGAACT CTTTGATCCG GTTCCTGAAC AGGATCTATT      aadA
 701  TGAGGCGCTA AATGAAACCT TAACGCTATG GAACTCGCCG CCCGACTGGG
 751  CTGGCGATGA GCGAAATGTA GTGCTTACGT TGTCCCGCAT TTGGTACAGC
 801  GCAGTAACCG GCAAAATCGC GCCGAAGGAT GTCGCTGCCG ACTGGGCAAT
 851  GGAGCGCCTG CCGGCCCAGT ATCAGCGCGT CATACTTGCG CGC AGATCAGTTG
 901  CTTATCTTGG ACAAGAAGAA GATCGCTTGG CCTCGCGCGC AGATCAGTTG
 951  GAAGAATTTG TCCACTACGT GAAAGGCGAG ATCACCAAGG TAGTGGGCAA
1001  Agaacttgca gttgaaggaa aattggaggt cgccATGgct AGTAAAGGAG
1051  AAGAACTTTT CACTGGAGTT GTCCCAATTC TTGTTGAATT AGATGGTGAT
1101  GTTAATGGGC ACAAATTTTC TGTCAGTGGA GAGGGTGAAG GTGATGCAAC
1151  ATACGGAAAA CTTACCCTTA AATTTATTTG CACTACTGGA AAACTACCTG
1201  TTCCttGGCC AACACTTGTC ACTACTTTCT CTTATGGTGT-TCAATGCTTT
1251  TCAAGATACC CAGATCATAT GAAGCGGCAC GACTTCTTCA AGAGCGCCAT
1301  GCCTGAGGGA TACGTGCAGG AGAGGACCAT CTCTTTCAAG GACGACGGGA
1351  ACTACAAGAC ACGTGCTGAA GTCAAGTTTG AGGGAGACAC CCTCGTCAAC
1401  AGGATCGAGC TTAAGGGAAT CGATTTCAAG GAGGACGGAA ACATCCTCGG      GFP
1451  CCACAAGTTG GAATACAACT ACAACTCCCA CAACGTATAC ATCACGGCAG
1501  ACAAACAAAA GAATGGAATC AAAGCTAACT TCAAAATTAG ACACAACATT
1551  GAAGATGGAA GCGTTCAACT AGCAGACCAT TATCAACAAA ATACTCCAAT
1601  TGGCGATGGC CCTGTCCTTT TACCAGACAA CCATTACCTG TCCACACAAT
1651  CTGCCCTTTC GAAAGATCCC AACGAAAAGA GAGACCACAT GGTCCTTCTT
1701  GAGTTTGTAA CAGCTGCTGG GATTACACAT GGCATGGATG AACTATACAA
1751  ATAAGctct agagcGATCC TGGCCTAGTC TATAGGAGGT TTGAAAAGA
1801  AAGGAGCAAT AATCATTTTC TTGTTCTATC AAGAGGGTGC TATTGCTCCT
1851  TTCTTTTTTT CTTTTTATTT ATTTACTAGT ATTTACTTA CATAGACTTT      TpsbA
1901  TTTGTTTACA TTATAGAAAA AGAAGGAGAG GTTATTTTCT TGCATTTATT
1951  CATGaaagct t
       HindIII
```

Figure 32 pMSK35.seq Length: 4671

Figure 33A p12248

```
   1 GGGAACGGAT TCACCGCCGT ATGGCTGACC GGCGATTACT AGCGATTCCT
  51 GCTTCATGCA GGCGAGTTGC AGCCTGCAAT CCGAACTGAG GACGGGTTTT
 101 TGGAGTTAGC TCACCCTCGC GAGATCGCGA CCCTTTGTCC CGCCCATTGT
 151 AGCACGTGTG TCGCCCAGGG CATAAGGGGC ATGATGACTT GGCCTCATCC
 201 TCTCCTTCCT CCGGCTTAAC ACCGGCGGTC TGTTCAGGGT TCCAAACTCA
 251 TAGTGGCAAC TAAACACGAG GGTTGCGCTC GTTGCGAGAC TTAACCCAAC
 301 ACCTTACGGC ACGAGCTGAC GACAGCCATG CACCACCTGT GTCCGCGTTC
 351 CCGAGGGCAC CCCTCTCTTT CAAGAGGATT CGCGGCATGT CAAGCCCTGG
 401 TAAGGTTCTT CGCTTTGCAT CGAATTAAAC CACATGCTCC ACCGCTTGTG
 451 CGGGCCCCCG TCAATTCCTT TGAGTTTCAT TCTTGCGAAC GTACTCCCCA
 501 GGCGGGATAC TTAACGCGTT AGCTACAGCA CTGCCACGGGT CGAGTCGCAC
 551 AGCACCTAGT ATCCATCGTT TACGGCTAGG ACTACTGGGG TCTCTAATCC
 601 CATTTGCTCC CCTAGCTTTC GTCTCTCAGT GTCAGTGTCG GCCCAGCAGA
 651 GTGCTTTCGC CGTTGGTGTT CTTTCCGATC TCAATGCATT TCACCGCTCC
 701 ACCGGAAATT CCCTCTGCCC CTACCGTACT CCAGCTTGGT AGTTTCCACC
 751 GCCTGTCCAG GGTTGAGCCC TGGGATTTGA CGGCGGACTT GAAAAGCCAC
 801 CTACAGACGC TTTACGCCCA ATCATTCCGG ATAACGCTTG CATCCTCTGT
 851 CTTACCGCGG CTGCTGGCAC AGAGTTAGCC GATGCTTATT CCTCAGATAC
 901 CGTCATTGTT TCTTCTCCGA GAAAGAAGT TGACGACCCG TGGGCCTTCC
 951 ACCTCCACGC GGCATTGCTC CGTCAGGCTT TCGCCCATTG CGGAAAATTC
1001 CCCACTGCTG CCTCCGTAG GAGTCTGGGC CGTGTCTCAG TCCCAGTGTG
1051 GCTGATCATC CTCTCGGACC AGCTACTGAT CATCGCCTTG GTAAGCTATT
1101 GCCTCACCAA CTAGCTAATC AGACGCGAGC CCCTCCTTGG GCGGATTTCT
1151 CCTTTTGCTC CTCAGCCTAC GGGGTATTAG CAACCGTTTC CAGTTGTTGT
1201 TCCCCTCCCA AGGGCACGTT CTTACGCGTT ACTCACCCGT TCGCCACTGG
1251 AAACACCACT TCCCGTTCGA CTTGCATGTG TTAAGCATGC CGCCAGCGTT
1301 CATCCTGAGC CAGGATCGAA CTCTCCATGA GATTCATAGT TGCATTACTT
1351 ATAGCTTCCT TATTCGTAGA CAAAGCGGAT TCGGAATTGT CTTTCCTTCC
1401 AAGGATAACT TGTATCCATG CGCTTCAGAT TATTAGCCTG GAGTTCGCCA
1451 CCAGCAGTAT AGCCAACCCT ACCCTATCAC GTCAATCCCA CAAGCCTCTT
1501 ATCCATTCCC GTTCGATCGT GGCGGGGGGA GTAAGTCAAA ATAGAAAAAA
1551 CTCACATTGG GTTTAGGGAT AATCAGGCTC GAACTGATGA CTTCCACCAC
1601 GTCAAGGTGA CACTCTACCG CTGAGTTATA TCCCTTCCCC GTCCCCTCGA
1651 GAAAGAGAAT TACCGAATCC TAAGGCAAAG GGGCGAGAAA CTCAAGGCCA
1701 CCCTTCCTCC GGGCTTTCTT TCCACACTAT TATGGATAGT CAAATAATGG
1751 GAAAAATTGG ATTCAATTGT CAACCGGTCC TATCGAAAAT AGGATTGACT
1801 ATGGATTCGA GCCATAGCAC ATGGTTTCAT AAAATCTGTA CGATTTTCCC
1851 GATCTAAATC GAGCAGGTTT CCATGAAGAA gatcgacggt atcgataagc
1901 ttgcatgcct gcaggtCGAA TATAGCTCTT CTTTCTTATT TCAATGATAT
1951 TATTATTTCA AAGATAAGAG ATATTCAAAG ATAAGAGATA AGAAGAAGTC
2001 AAAATTTGAT TTTTTTTTTG GAAAAAAAAA ATCAAAAAGA TATAGTAACA
2051 TTAGCAAGAA GAGAAACAAG TTCTATTTCA CAATTTAAAC AAATACAAAA
2101 TCAAAATAGA ATACTCAATC ATGAATAAAT GCAAGAAAAT AACCTCTCCT
2151 TCTTTTTCTA TAATGTAAAC AAAAAAGTCT ATGTAAGTAA AATACTAGTA
2201 AATAAATAAA AAGAAAAAAA GAAAGGAGCA ATAGCACCCT CTTGATAGAA
2251 CAAGAAAATG ATTATTGCTC CTTTCTTTTC AAAACCTCCT ATAGACTAGG
2301 CCAGGATCgc tctagcTAGA CATTATTTGC CGACTACCTT GGTGATCTCG
2351 CCTTTCACGT AGTGGACAAA TTCTTCCAAC TGATCTGCGC GCGAGGCCAA
2401 GCGATCTTCT TCTTGTCCAA GATAAGCCTG TCTAGCTTCA AGTATGACGG
2451 GCTGATACTG GGCCGGCAGG CGCTCCATTG CCCAGTCGGC AGCGACATCC
2501 TTCGGCGCGA TTTTGCCGGT TACTGCGCTG TACCAAATGC GGGACAACGT
2551 AAGCACTACA TTTCGCTCAT CGCCAGCCCA GTCGGGCGGC GAGTTCCATA
2601 GCGTTAAGGT TTCATTTAGC GCCTCAAATA GATCCTGTTC AGGAACCGGA
2651 TCAAAGAGTT CCTCCGCCGC TGGACCTACC AAGGCAACGC TATGTTCTCT
2701 TGCTTTTGTC AGCAAGATAG CCAGATCAAT GTCGATCGTG GCTGGCTCGA
```

Rice Left targeting Sequence accdA pMSK35.seq Length: 4671

```
2751 AGATACCTGC AAGAATGTCA TTGCGCTGCC ATTCTCCAAA TTGCAGTTCG ⎫
2801 CGCTTAGCTG GATAACGCCA CGGAATGATG TCGTCGTGCA CAACAATGGT │
2851 GACTTCTACA GCGCGGAGAA TCTCGCTCTC TCCAGGGGAA GCCGAAGTTT │ aadA
2901 CCAAAAGGTC GTTGATCAAA GCTCGCCGCG TTGTTTCATC AAGCCTTACG │
2951 GTCACCGTAA CCAGCAAATC AATATCACTG TGTGGCTTCA GGCCGCCATC │
3001 CACTGCGGAG CCGTACAAAT GTACGGCCAG CAACGTCGGT TCGAGATGGC │
3051 GCTCGATGAC GCCAACTACC TCTGATAGTT GAGTCGATAC TTCGGCGATC │
3101 ACCGCTTCCC TCATGgATCC CTCCCTACAA CTGTATCCAa GCGCTTCgTA │
3151 TTCGCCCGGA GTTCGCTCCC AGAAATATAG CCATCCCTGC CCCCTCACGT │
3201 CAATCCCACG AGCCTCTTAT CCATTCTCAT TGAACGACGG CGGGGGAGC ⎭
3251 ttgggtaccg agctcgaatt cctgcagccc gatcTTACCA TTTCCGAAGG ⎫
3301 AACTGGGGCT ACATTTCTTT TCAATTTCCA TTCAAGAGTT TCTTATCTGT │
3351 TTCCACGCCC TTTTTGAGA CCTCGAAACA TGAAATGGAC AAATTCCTTC │
3401 TCTTAGGAAC ACATACAAGA AAAAGGATAA TGGTAGCCCT CCCATTAACT │
3451 ACTTCATTTC ATTTATGAAT TTCATAGTAA TAGAAATCCA TGTCCTACCG │
3501 AGACAGAATT TCGAACTTGC TATCCTCTTG CCTAATAGGC AAAGATTGAC │
3551 CTCTGTAGAA AGAATGATTC ATTCGGATCG ATATGAGGAC CCAACTACGT │
3601 TGCATTGCAG AATCCATGTT CCATATTTGA AGAGGGTTGA CCTCTGTGCT │
3651 TCTCTCATGG TACAATCCTC TTCCTGCTGA GCCCCTTTC TCCTCGGTCC │
3701 ACAGAGAAAA AATGGAGGAC TGGTGCCGAC AGTTCATCAC GGAAGAAAGA │
3751 ACTCACAGAG CCGGGATCGC TAACTAATAG AATAGTACTA CTAACTAATA │ Rice Right targeting sequence
3801 CTAATATATA GAAATAGATA TctagctagA AATAGAAACA ACTAATATAT │
3851 AGATAATCGA AATTGAAAAG AACTGTCTTT TCTGTATACT TTCCCCGTTC │
3901 TATTGCTACC GCGGGTCTTA TGCAATCGAT CGGATCATAT AGATATCCCT │
3951 TCAACACAAC ATAGGTCATC GAAGGATCT CGGACGACTC ACCAAAGCAG │
4001 GAAAGCCAGT TAGAAAATGG ATTCCTATTT GAAGAGTGCC TAACCGCATG │
4051 GATAAGCTCA CATTAACCCG TCAATTTTGG ATCCAATTCG GGATTTTTCT │
4101 TGGGAAGTTT CGGGAAGAAA TTGAATGGA ATAATATAGA TTCATACAGA │
4151 GGAAAAGGTT CTCTATTGAT GCAAACGCTG TACCTAGAGG ATAGGGATAG │
4201 AGGAAGAGGG .AAAAATCGAA ATGAAATAAA TAAAGAATAA AGCAAAAAAA │
4251 AAATAAGTCG AAGATAGAAG AGCCCAGATT CCAAATGAAG AAATGGAAAC │
4301 TCGAAAAGGA TCCTTCTGAT TCTCAAAGAA TGAGGGCAA GGGGATTGAT │
4351 ACCGAGAAAG ATTTCTTCTT ATTATAAGAC GTGATTTGAT CCGCATATGT │
4401 TTGGTAAAAG AACAATCTTC TCCTTTAATC ATAAATGGAA AGTGTTCAAT │
4451 TAGAACATGA AAACGTGACT CAATTGGTCT TAGTTAGTCT TCGGGACGGA │
4501 GTGGAAGAAA GGGCGAAGAC TCTCGAACGA GGAAAAGGAT CCCTTCGAAA │
4551 GAATTGAACG AGGAGCCGTA TTAGGTGAAA ATCTCATGTA CGATTCTGTA │
4601 GAGGGACAGG AAGGGTGACT TATCTGTCGA CTTTTCCACT ATCAACCCCA │
4651 AAAACCCAA CTCTGCCTTA C ⎭
```

Figure 33B pMSK49.seq Length: 5263

```
   1  GGGAACGGAT TCACCGCCGT ATGGCTGACC GGCGATTACT AGCGATTCCT
  51  GCTTCATGCA GGCGAGTTGC AGCCTGCAAT CCGAACTGAG GACGGGTTTT
 101  TGGAGTTAGC TCACCCTCGC GAGATCGCGA CCCTTTGTCC CGCCCATTGT
 151  AGCACGTGTG TCGCCCAGGG CATAAGGGGC ATGATGACTT GGCCTCATCC
 201  TCTCCTTCCT CCGGCTTAAC ACCGGCGGTC TGTTCAGGGT TCCAAACTCA
 251  TAGTGGCAAC TAAACACGAG GGTTGCGCTC GTTGCGAGAC TTAACCCAAC
 301  ACCTTACGGC ACGAGCTGAC GACAGCCATG CACCACCTGT GTCCGCGTTC
 351  CCGAGGGCAC CCCTCTCTTT CAAGAGGATT CGCGGCATGT CAAGCCCTGG
 401  TAAGGTTCTT CGCTTTGCAT CGAATTAAAC CACATGCTCC ACCGCTTGTG
 451  CGGGCCCCCG TCAATTCCTT TGAGTTTCAT TCTTGCGAAC GTACTCCCCA
 501  GGCGGGATAC TTAACGCGTT AGCTACAGCA CTGCACGGGT CGAGTCGCAC
 551  AGCACCTAGT ATCCATCGTT TACGGCTAGG ACTACTGGGG TCTCTAATCC
 601  CATTTGCTCC CCTAGCTTTC GTCTCTCAGT GTCAGTGTCG GCCCAGCAGA
 651  GTGCTTTCGC CGTTGGTGTT CTTTCCGATC TCAATGCATT TCACCGCTCC
 701  ACCGGAAATT CCCTCTGCCC CTACCGTACT CCAGCTTGGT AGTTTCCACC
 751  GCCTGTCCAG GGTTGAGCCC TGGGATTTGA CGGCGGACTT GAAAAGCCAC
 801  CTACAGACGC TTTACGCCCA ATCATTCCGG ATAACGCTTG CATCCTCTGT
 851  CTTACCGCGG CTGCTGGCAC AGAGTTAGCC GATGCTTATT CCTCAGATAC
 901  CGTCATTGTT TCTTCTCCGA GAAAAGAAGT TGACGACCCG TGGGCCTTCC
 951  ACCTCCACGC GGCATTGCTC CGTCAGGCTT TCGCCCATTG CGGAAAATTC
1001  CCCACTGCTG CCTCCCGTAG GAGTCTGGGC CGTGTCTCAG TCCCAGTGTG
1051  GCTGATCATC CTCTCGGACC AGCTACTGAT CATCGCCTTG GTAAGCTATT
1101  GCCTCACCAA CTAGCTAATC AGACGCGAGC CCCTCCTTGG GCGGATTTCT
1151  CCTTTTGCTC CTCAGCCTAC GGGGTATTAG CAACCGTTTC CAGTTGTTGT
1201  TCCCCTCCCA AGGGCAGGTT CTTACGCGTT ACTCACCCGT TCGCCACTGG
1251  AAACACCACT TCCCGTTCGA CTTGCATGTG TTAAGCATGC CGCCAGCGTT
1301  CATCCTGAGC CAGGATCGAA CTCTCCATGA GATTCATAGT TGCATTACTT
1351  ATAGCTTCCT TATTCCTAGA CAAAGCGGAT TCGGAATTGT CTTTCCTTCC
1401  AAGGATAACT TGTATCCATG CGCTTCAGAT TATTAGCCTG GAGTTCGCCA
1451  CCAGCAGTAT AGCCAACCCT ACCCTATCAC GTCAATCCCA CAAGCCTCTT
1501  ATCCATTCCC GTTCGATCGT GGCGGGGGGA GTAAGTCAAA ATAGAAAAAA
1551  CTCACATTGG GTTTAGGGAT AATCAGGCTC GAACTGATGA CTTCCACCAC
1601  GTCAAGGTGA CACTCTACCG CTGAGTTATA TCCCTTCCCC GTCCCCTCGA
1651  GAAAGAGAAT TACCGAATCC TAAGGCAAAG GGGCGAGAAA CTCAAGGCCA
1701  CCCTTCCTCC GGGCTTTCTT TCCACACTAT TATGGATAGT CAAATAATGG
1751  GAAAAATTGG ATTCAATTGT CAACCGGTCC TATCGAAAAT AGGATTGACT
1801  ATGGATTCGA GCCATAGCAC ATGGTTTCAT AAAATCTGTA CGATTTTCCC
1851  GATCTAAATC GAGCAGGTTT CCATGAAGAA gatcgacggt atcgataagc
1901  ttcATGAAT AAATGCAAGA AATAACCTC TCCTTCTTTT TCTATAATGT
1951  AAACAAAAAA GTCTATGTAA GTAAAATACT AGTAAATAAA TAAAAAGAAA
2001  AAAAGAAAGG AGCAATAGCA CCCTCTTGAT AGAACAAGAA AATGATTATT
2051  GCTCCTTTCT TTTCAAAACC TCCTATAGAC TAGGCCAGGA TCgctctaga
2101  gcCTTATTTG TATAGTTCAT CCATGCCATG TGTAATCCCA GCAGCTGTTA
2151  CAAACTCAAG AAGGACCATG TGGTCTCTCT TTTCGTTGGG ATCTTTCGAA
2201  AGGGCAGATT GTGTGGACAG GTAATGGTTG TCTGGTAAAA GGACAGGGCC
2251  ATCGCCAATT GGAGTATTTT GTTGATAATG GTCTGCTAGT TGAACGCTTC
2301  CATCTTCAAT GTTGTGTCTA ATTTGAAGT TAGCTTTGAT TCCATTCTTT
2351  TGTTTGTCTG CCGTGATGTA TACGTTGTGG GAGTTGTAGT TGTATTCCAA
2401  CTTGTGGCCG AGGATGTTTC CGTCCTCCTT GAAATCGATT CCCTTAAGCT
2451  CGATCCTGTT GACGAGGGTG TCTCCCTCAA ACTTGACTTC AGCACGTGTC
2501  TTGTAGTTCC CGTCGTCCTT GAAAGAGATG GTCCTCTCCT GCACGTATCC
2551  CTCAGGCATG GCGCTCTTGA AGAAGTCGTG CCGCTTCATA TGATCTGGGT
2601  ATCTTGAAAA GCATTGAACA CCATAAGAGA AAGTAGTGAC AAGTGTTGGC
2651  CAaGGAACAG GTAGTTTTCC AGTAGTGCAA ATAAATTTAA GGGTAAGTTT
2701  TCCGTATGTT GCATCACCTT CACCCTCTCC ACTGACAGAA AATTTGTGCC
```

Rice Left targeting Sequence

TpsbA

GFP

Figure 34B pMSK49.seq Length: 5263

```
2751  CATTAACATC ACCATCTAAT TCAACAAGAA TTGGGACAAC TCCAGTGAAA
2801  AGTTCTTCTC CTTTACTagc CATggcgacc tccaattttc cttcaactgc
2851  aagttcTTTG CCCACTACCT TGGTGATCTC GCCTTTCACG TAGTGGACAA
2901  ATTCTTCCAA CTGATCTGCG CGCGAGGCCA AGCGATCTTC TTCTTGTCCA
2951  AGATAAGCCT GTCTAGCTTC AAGTATGACG GGCTGATACT GGGCCGGCAG
3001  GCGCTCCATT GCCCAGTCGG CAGCGACATC CTTCGGCGCG ATTTTGCCGG
3051  TTACTGCGCT GTACCAAATG CGGGACAACG TAAGCACTAC ATTTCGCTCA
3101  TCGCCAGCCC AGTCGGGCGG CGAGTTCCAT AGCGTTAAGG TTTCATTTAG
3151  CGCCTCAAAT AGATCCTGTT CAGGAACCGG ATCAAAGAGT TCCTCCGCCG
3201  CAGGACCTAC CAAGGCAACG CTATGTTCTC TTGCTTTTGT CAGCAAGATA
3251  GCCAGATCAA TGTCGATCGT GGCTGGCTCG AAGATACCTG CAAGAATGTC
3301  ATTGCGCTGC CATTCTCCAA ATTGCAGTTC GCGCTTAGCT GGATAACGCC
3351  ACGGAATGAT GTCGTCGTGC ACAACAATGG TGACTTCTAC AGCGCGGAGA
3401  ATCTCGCTCT CTCCAGGGGA AGCCGAAGTT TCCAAAAGGT CGTTGATCAA
3451  AGCTCGCCGC GTTGTTTCAT CAAGCCTTAC GGTCACCGTA ACCAGCAAAT
3501  CAATATCACT GTGTGGCTTC AGGCCGCCAT CCACTGCGGA GCCGTACAAA
3551  TGTACGGCCA GCAACGTCGG TTCGAGATGG CGCTCGATGA CGCCAACTAC
3601  CTCTGATAGT TGAGTCGATA CTTCGGCGAT CACCGCTTCg ctaggcaagt
3651  cttcttcaga aatgagtttt tgttcgctag cCTGTCCACC AGTCATGCTt
3701  GCCATATGTA TATCTCCTTC TTAAAGTTAA ACAAAATTAT TTCTAGtGGG
3751  AAACCGTTGT GGTCTCCCTC CCAGAAATAT AGCCATCCCT GCCCCCTCAC
3801  GTCAATCCCA CGAGCCTCTT ATCCATTCTC ATTGAACGAC GGCGGGGGAG
3851  Cgagctcgaa ttcctgcagc ccgatcTTAC CATTTCCGAA GGAACTGGGG
3901  CTACATTTCT TTCAATTTC CATTCAAGAG TTTCTTATCT GTTTCCACGC
3951  CCTTTTTTGA GACCTCGAAA CATGAAATGG ACAAATTCCT TCTCTTAGGA
4001  ACACATACAA GAAAAAGGAT AATGGTAGCC CTCCCATTAA CTACTTCATT
4051  TCATTTATGA ATTTCATAGT AATAGAAATC CATGTCCTAC CGAGACAGAA
4101  TTTCGAACTT GCTATCCTCT TGCCTAATAG GCAAAGATTG ACCTCTGTAG
4151  AAAGAATGAT TCATTCGGAT CGATATGAGG ACCCAACTAC GTTGCATTGC
4201  AGAATCCATG TTCCATATTT GAAGAGGGTT GACCTCTGTG CTTCTCTCAT
4251  GGTACAATCC TCTTCCTGCT GAGCCCCCTT TCTCCTCGGT CCACAGAGAA
4301  AAAATGGAGG ACTGGTGCCG ACAGTTCATC ACGGAAGAAA GAACTCACAG
4351  AGCCGGGATC GCTAACTAAT AGAATAGTAC TACTAACTAA TACTAATATA
4401  TAGAAATAGA TATctagcta gAAATAGAAA CAACTAATAT ATAGATAATC
4451  GAAATTGAAA AGAACTGTCT TTTCTGTATA CTTTCCCCGT TCTATTGCTA
4501  CCGCGGGTCT TATGCAATCG ATCGGATCAT ATAGATATCC CTTCAACACA
4551  ACATAGGTCA TCGAAAGGAT CTCGGACGAC TCACCAAAGC ACGAAAGCCA
4601  GTTAGAAAAT GGATTCCTAT TTGAAGAGTG CCTAACCGCA TGGATAAGCT
4651  CACATTAACC CGTCAATTTT GGATCCAATT CGGGATTTTT CTTGGGAAGT
4701  TTCGGGAAGA AATTGGAATG GAATAATATA GATTCATACA GAGGAAAGG
4751  TTCTCTATTG ATGCAAACGC TGTACCTAGA GGATAGGGAT AGAGGAAGAG
4801  GGAAAAATCG AAATGAAATA AATAAAGAAT AAAGCAAAAA AAAAATAAGT
4851  CGAAGATAGA AGAGCCAGA TTCCAAATGA AGAAATGGAA ACTCGAAAAG
4901  GATCCTTCTG ATTCTCAAAG AATGAGGGGC AAGGGGATTG ATACCGAGAA
4951  AGATTTCTTC TTATTATAAG ACGTGATTTG ATCCGCATAT GTTTGGTAAA
5001  AGAACAATCT TCTCCTTTAA TCATAAATGG AAAGTGTTCA ATTAGAACAT
5051  GAAAACGTGA CTCAATTGGT CTTAGTTAGT CTTCGGGACG GAGTGGAAGA
5101  AAGGGCGAAG ACTCTCGAAC GAGGAAAAGG ATCCCTTCGA AAGAATTGAA
5151  CGAGGAGCCG TATTAGGTGA AAATCTCATG TACGATTCTG TAGAGGGACA
5201  GGAAGGGTGA CTTATCTGTC GACTTTTCCA CTATCAACCC CAAAAAACCC
5251  AACTCTGCCT TAC
```

| Gene | Product | Plasmid |
|---|---|---|
| *aadA16gfp* | FLARE16-S | pMSK51 (BS) |
| *aadA16gfp-S1* | FLARE16-S1 | pMSK56 (Nt-pRV111B) |
| *aadA16gfp-S2* | FLARE16-S2 | pMSK57 (Nt-pRV111B) |
| *aadA11gfp-S3* | FLARE11-S3 | pMSK49 (Os-pMSK49) |

Figure 35

TRANSLATION CONTROL ELEMENTS FOR HIGH-LEVEL PROTEIN EXPRESSION IN THE PLASTIDS OF HIGHER PLANTS AND METHODS OF USE THEREOF

This application claims priority from U.S. Provisional Applications 60/095,163, filed Aug. 3, 1998, 60/112,257, filed Dec. 15, 1998, 60/095,167 filed Aug. 3, 1998, 60/131, 611, filed Apr. 29, 1999 and 60/138,764, filed Jun. 11, 1999 under 35 U.S.C. §119(e). The entire disclosures of each of the foregoing are incorporated by reference herein.

Pursuant to 35 U.S.C. §202(c) it is acknowledged that the U.S. Government has certain rights in the invention described herein, which was made in part with funds from the National Science Foundation, Grant Number MCB-96-30763.

FIELD OF THE INVENTION

This invention relates to the fields of transgenic plants and molecular biology. More specifically, the invention provides vectors targeting the plastid genome which contain translation control elements facilitating high levels of protein expression in the plastids of higher plants. Both monocots and dicots are successfully transformed with the DNA constructs provided herein.

BACKGROUND OF THE INVENTION

Several publications are referenced in this application in order to more fully describe the state of the art to which this invention pertains. The disclosure of each of these publications is incorporated by reference herein.

The chloroplasts of higher plants accumulate individual components of the photosynthetic machinery as a relatively large fraction of total cellular protein. The best example is the enzyme ribulose-1,5-bisphosphate carboxylase-oxygenase (Rubisco) involved in $CO_2$ fixation which can make up 65% of the total leaf protein (Ellis, R. J. 1979). Because of the potentially attainable high protein levels, there is significant interest in exploring chloroplasts as an alternative system for protein expression. To date, protein levels expressed from transgenes in chloroplasts are below the levels of highly-expressed chloroplast genes. Highest levels reported thus far in leaves are as follows: 1% of neomycin phophotransferase (Carrer et al., 1993); 2.5% β-glucuronidase (Staub and Maliga, 1993) and 3–5% of *Bacillus thuringiensis* (Bt) crystal toxins (McBride et al., 1995). An alternative system, based on a nuclear-encoded, plastid-targeted T7 RNA polymerase may offer higher levels of protein expression (McBride t al., 1994), although this yield may come at a price.

In bacteria, the rate limiting step of protein synthesis is usually the initiation of translation, involving the binding of the initiator tRNA (formyl-methionyl-tRNA$_f$) and mRNA to the 70S ribosome, recognition of the initiator codon, and the precise phasing of the reading frame of the mRNA. Translation initiation depends on three initiation factors (IF1, IF2, IF3) and requires GTP. The 30S subunit is guided to the initiation codon by RNA—RNA base pairing between the 3' of the 16S rRNA and the mRNA ribosome binding site, or Shine-Dalgarno (SD) sequence, located about 10 nucleotides upstream of the translation initiation codon (Voorma, 1996). RNA—RNA interaction between the "downstream box" (DB), a 15 nt sequence downstream of the AUG translational initiation codon and complementary sequences in the 16S rRNA 3' sequence or anti-downstream box (ADB; nucleotide positions 1469–1483) may also facilitate loading of the mRNA onto the 30S ribosome subunit (Sprengart et al., 1996). In addition, specific protein-RNA interactions may also facilitate translation initiation (Voorma, 1996).

Key components of the prokaryotic translation machinery have been identified in plastids, including homologues of the bacterial IF1, IF2 and IF3 initiation factors and an S1-like ribosomal protein (Stern et al., 1997). Most plastid mRNAs (92%) contain a ribosome binding site or SD sequence: GGAGG, or its truncated tri- or tetranucleotide variant. This sequence is similar to the bacterial SD consensus 5'-UAAGGAGGUGA-3' (SEQ ID NO: 28; Voorma, 1996). High level expression of foreign genes of interest in the plastids of higher plants is extremely desirable. The present invention provides novel genetic translational control elements for use in plastid transformation vectors. Incorporation of these elements into such vectors results in protein expression levels comparable to those observed for highly expressed chloroplast genes in both monocots and dicots.

SUMMARY OF THE INVENTION

5' genetic regulatory regions contain promoters with distinct DNA sequence information which facilitates recognition by the RNA polymerase and translational control elements which facilitate translation. Both of these components act together to drive gene expression.

In accordance with the present invention, chimeric 5' regulatory regions have been constructed which incorporate translation control elements. Incorporation of these chimeric 5' regulatory regions into plastid transforming vectors followed by transformation of target plant cells gives rise to dramatically enhanced levels of protein expression. These chimeric 5' regulatory regions may be used to advantage to express foreign genes of interest in a wide range of plant tissues. It is an object of the present invention to provide DNA constructs and methods for stably transforming plastids of multicellular plants containing such promoters.

In one embodiment of the invention recombinant DNA constructs for expressing at least one heterologous protein in the plastids of higher plants are provided. The constructs comprise a 5' regulatory region which includes a promoter element, a leader sequence and a downstream box element operably linked to a coding region of said at least one heterologous protein. The chimeric regulatory region acts to enhance translational efficiency of an mRNA molecule encoded by said DNA construct. Vectors comprising the DNA constructs are also contemplated in the present invention. Exemplary DNA constructs of the invention include the following chimeric regulatory regions: PrrnLatpB+DBwt, PrrnLatpB–DB, PrrnLatpB+DBm, PrrnLclpP+DBwt, PrrnclpP–DB, PrrnLrbcL+DBwt, PrrnLrbcL–DB, PrrnLrbcL+DBm, PrrnLpsbB+DBwt, PrrnLpsbB–DB, PrrnLpsbA+DBwt, PrrnLpsbA–DB, PrrnLpsbA–DB(+GC), PrrnLT7g10+DB/Ec, PrrnLT7g10+DB/pt, and PrrnLT7g10–DB. Downstream box sequences preferred for use in the constructs of the invention have the following sequences: 5'TCCAGTCACTAGCCCTGCCTTCGGCA'3 (SEQ ID NO: 29) and 5'CCCAGTCATGAATCACAAAGTGG-TAA'3 (SEQ ID NO: 30).

The 5' regulatory segments of the invention have been successfully employed to drive the expression of the bar gene from *S. hydroscopicus* in the plastids of higher plants. Synthetic bar genes have also been generated and expressed using the DNA constructs of the present invention. These constructs have been engineered to maximize transgene containment in plastids by incorporating rare codons into the coding region that are not preferred for protein translation in microorganisms and fungi.

In yet another embodiment of the invention, at least one fusion protein is produced utilizing the DNA constructs of the invention. An exemplary fusion protein has a first and second coding region operably linked to the 5' regulatory regions described herein such that production of said fusion protein is regulated by said 5' regulatory region. In one embodiment the first coding region encodes a selectable marker gene and the second coding region encodes a fluorescent molecule to facilitate visualization of transformed plant cells. Vectors comprising a DNA construct encoding such a fusion protein are also within the scope of the present invention. An exemplary fusion protein consists an aadA coding region operably linked to a green fluorescent protein coding region. These moieties may be linked by peptide linkers such as ELVEGKLELVEGLKVA (SEQ ID NO: 104) and ELAVEGKLEVA(SEQ ID NO: 105).

Plasmids for transforming the plastids of higher plants, are also included in the present invention. Exemplary plasmids are selected from the group consisting of pHK30(B), pHK31(B), pHK60, pHK32(B), pHK33 (B), pHK34 (A), pHK35 (A), pHK64 (A), pHK36 (A), pHK37 (A), pHK38 (A), pHK39 (A), pHK40 (A), pHK41 (A), pHK42(A), pHK43(A), pMSK56, pMSK57, pMSK48, pMSK49, pMSK35, pMSK53 and pMSK54.

Transgenic plants, both monocots and dicots harboring the plasmids set forth above are also contemplated to be within the scope of the invention.

In yet another embodiment of the invention, methods are provided for producing transplastomic monocots. One method comprises a) obtaining embryogenic cells; b) exposing said cells to a heterologous DNA molecule under conditions whereby said DNA enters the plastids of said cells, said heterologous DNA molecule encoding at least one exogenous protein, said at least one exogenous protein encoding a selectable marker; c) applying a selection agent to said cells to facilitate sorting of untransformed plastids from transformed plastids, said cells containing transformed plastids surviving and dividing in the presence of said selection agent; d) transferring said surviving cells to selective media to promote plant regeneration and shoot growth; and e) rooting said shoots, thereby producing transplastomic monocot plants. The heterologous DNA molecule may be introduced into the plant cell via a process selected from the group consisting of biolistic bombardment, *Agrobacterium*-mediated transformation, microinjection and electroporation. In one embodiment of the above described method, protoplasts are obtained from the embryogenic cells and the heterologous DNA molecule is delivered to said protoplasts by exposure to polyethylene glycol. Suitable selection agents for the practice of the methods of the invention are streptomycin, and paromomycin. Monocot plants which may be transformed using the methods of the invention include but are not limited to maize, millet, sorghum, sugar cane, rice, wheat, barley, oat, rye, and turf grass.

In a preferred embodiment a method for producing transplastomic rice plants is provided. This method entails the following steps: a) obtaining embryogenic calli; b) inducing proliferation of calli on modified CIM medium; c) obtaining embryogenic cell suspensions of said proliferating calli in liquid AA medium; d) bombarding said embryogenic cells with microprojectiles coated with plasmid DNA; e) tranferring said bombarded cells to selective liquid AA medium; f) transferring said cells surviving in AA medium to selective RRM regeneration medium for a time period sufficient for green shoots to appear; and g) rooting said shoots in a selective MS salt medium.

Plasmids suitable for transforming rice as set forth above include pMSK35 and pMSK53, pMSK54 and pMSK49. Transplastomic rice plants so produced are also contemplated to be within the scope of the invention.

In yet a final embodiment of the invention methods for containing transgenes in transformed plants are provided. An emplary method includes the following steps: a) determining the codon usage in said plant to be transformed and in microbes found in association with said plant; and b) genetically engineering said transgene sequence via the introduction of rare microbial codons to abrogate expression of said transgene in said plant associated microbe. In an exemplary embodiment of the method described immediately above the transgene is a bar gene and said rare codons are arginine encoding codons selected from the group consisting of AGA and AGG, and transgene is not expressed in *E. coli*.

The following definitions will facilitate the understanding of the subject matter of the present invention:

Heteroplastomic: refers to the presence of a mixed population of different plastid genomes within a single plastid or in a population of plastids contained in plant cells or tissues.

Homoplastomic: refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome: the genome of a plastid.

Transplastome: a transformed plastid genome.

Transformation of plastids: stable integration of transforming DNA into the plastid genome that is transmitted to the seed progeny of plants containing the transformed plastids.

Selectable marker gene: the term "selectable marker gene" refers to a gene that upon expression confers a selective advantage to the plastids and a phenotype by which successfully transformed plastids or cells or tissues carrying the transformed plastid can be identified.

Transforming DNA: refers to homologous DNA, or heterologous DNA flanked by homologous DNA, which when introduced into plastids becomes part of the plastid genome by homologous recombination.

Operably linked: refers to two different regions or two separate genes spliced together in a construct such that both regions will function to promote gene expression and/or protein translation.

The detailed description as follows provides examples of preferred methods for making and using the DNA constructs of the present invention and for practicing the methods of the invention. Any molecular cloning and recombinant DNA techniques not specifically described are carried out by standard methods, as generally set forth, for example in Sambrook et al., "DNA Cloning, A Laboratory Manual," Cold Spring Harbor Laboratory, 1989.

BRIEF DESCRIPTION OF THE DRAWINGS

"The patent or application file contains at least one drawing executed in color. Copies of this patent or patent application publication with color drawing(s) will be provided by the Office upon request and payment of the necessary fee."

FIG. 2B. Complementarity of Prrn T7 phage gene 10 leader derivatives (T7g10, SEQ ID NO: 118; T7g10+DB/Ec, SEQ ID NO: 119; T7g10+DB/pt, SEQ ID NO: 120; T7g10−DB, SEQ ID NO: 121) with the *E. coli* (SEQ ID NO: 110) and plastid (SEQ ID NO: 109) ADB sequences. Nucleotides changed to reduce or alter mRNA-rRNA interaction are in lower case. The number of potential nucleotide pairs formed with the 26 nt ADB region is in parenthesis.

FIG. 3A. DNA sequence of the chimeric Prrn plastid promoter fragments with atpB and clpP translation control regions (PrrnLatpB+DBwt, SEQ ID NO: 1; PrrnLatpB−DB, SEQ ID NO: 2; PrrnLatpB+DBm, SEQ ID NO: 3; PmmLclpP+DBwt, SEQ ID NO: 4; PrrnLclpP−DB, SEQ ID NO: 5). The plasmid name that is the source of the promoter fragment is given in parenthesis. The Prrn promoter sequence is underlined; nucleotide at which transcription initiates in tobacco plastids is marked with filled circle; translational initiation codon (ATG) is in bold; SD is underlined with a wavy line; nucleotides of the 5′ and 3′ restriction sites and point mutations are in lower case.

FIG. 3B. DNA sequence of the chimeric Prrn plastid promoter fragments with rbcL and psbB translation control regions (PrrnLrbcL+DBwt, SEQ ID NO: 6; PrrnLrbcL−DB, SEQ ID NO: 7; PrrnLrbcL+DBm, SEQ ID NO: 8; PrrnLpsbB+DBwt, SEQ ID NO: 9; PrrnLpsbB−DB, SEQ ID NO: 10). For details see description of FIG. 3A.

FIG. 3C. DNA sequence of the chimeric Prrn plastid promoter fragments with psbA translation control regions (PrrnLpsbA+DBwt, SEQ ID NO: 11; PrrnLpsbA−DB, SEQ ID NO: 12; PrrnLpsbA−DB(+GC), SEQ ID NO: 13). For details see description of FIG. 3A.

FIG. 3D. DNA sequence of the chimeric Prrn plastid promoter fragments with the T7 phage gene 10 (PrrnLT7g10+DB/Ec; SEQ ID NO: 14) plastid (PrrnLT7g10+DB/pt; SEQ ID NO: 15) and synthetic DB (PrrnLT7g10−DB; SEQ ID NO: 16). For details see description of FIG. 3A.

The patent or application file contains at least one drawing executed in color. Copies of this patent or patent application publication with color drawing(s) will be provided by the Office upon request and payment of the necessary fee.

Figure 4A:
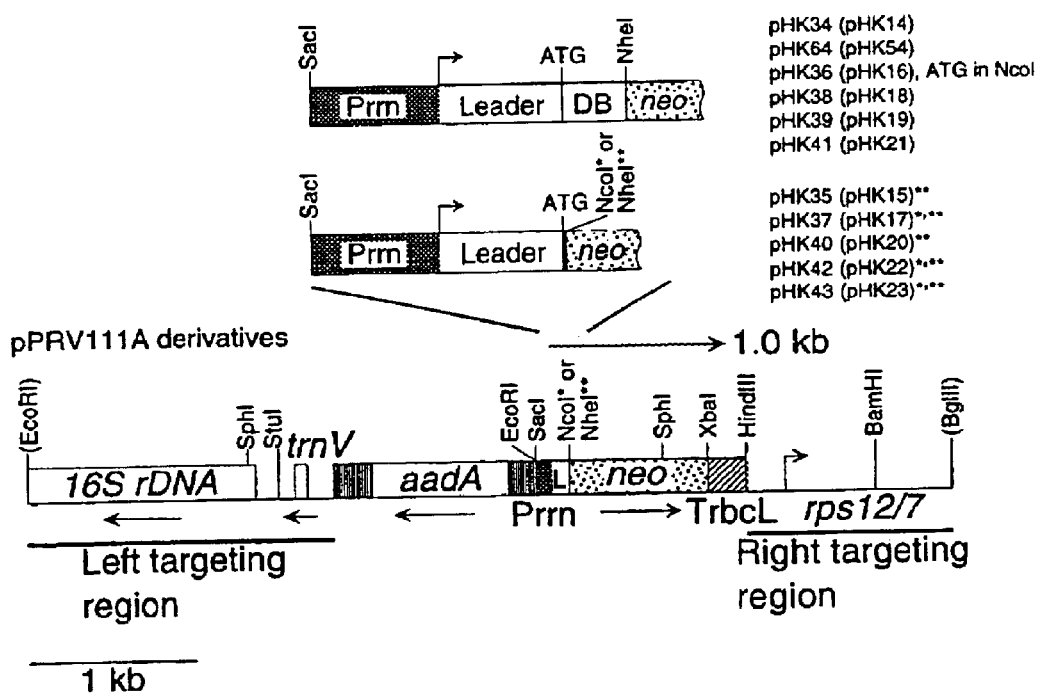

FIG. 4A. Plastid transformation vector pPRV111A with chimeric neo genes. Plasmid serial numbers, for example pHK34, designate pPRV111A plastid transformation vectors derivatives; adjacent plasmid numbers in parenthesis (e.g. pHK14) designate the source of the chimeric neo gene in pUC118 or pBSIIKS+ vectors. Arrows mark orientation of the selectable marker gene (aadA) and of the chimeric neo gene. Plastid targeting sequences are underlined in bold. Components of the chimeric neo genes are: Prrn, rRNA operon promoter fragment; L, leader sequence; DB, downstream box; NheI site which serves as a synthetic DB is marked by a heavy line; neo, neomycin phosphotransferase coding region; TrbcL, rbcL 3′-untranslated region. 16SrDNA, trnV, rps12/7 are plastid genes (Shinozaki et al., 1986). The restriction sites marked for: EcoRI, SphI, StuI, SacI, NheI, NcoI, XbaI, HindIII, BamHI and BglII. Restriction sites in brackets were eliminated during construction. The neo translation initiation in plasmid pHK36 is included in NcoI site (not marked). The presence and relative order of NheI (**) and NcoI (*) restriction sites in the plasmid pPRV111A−DB derivatives (pHK35, pHK37, pHK40, pHK42, pHK43) are marked by asterisks. The promoter sequences are shown in FIGS. 3B, C and D.

Figure 4B:
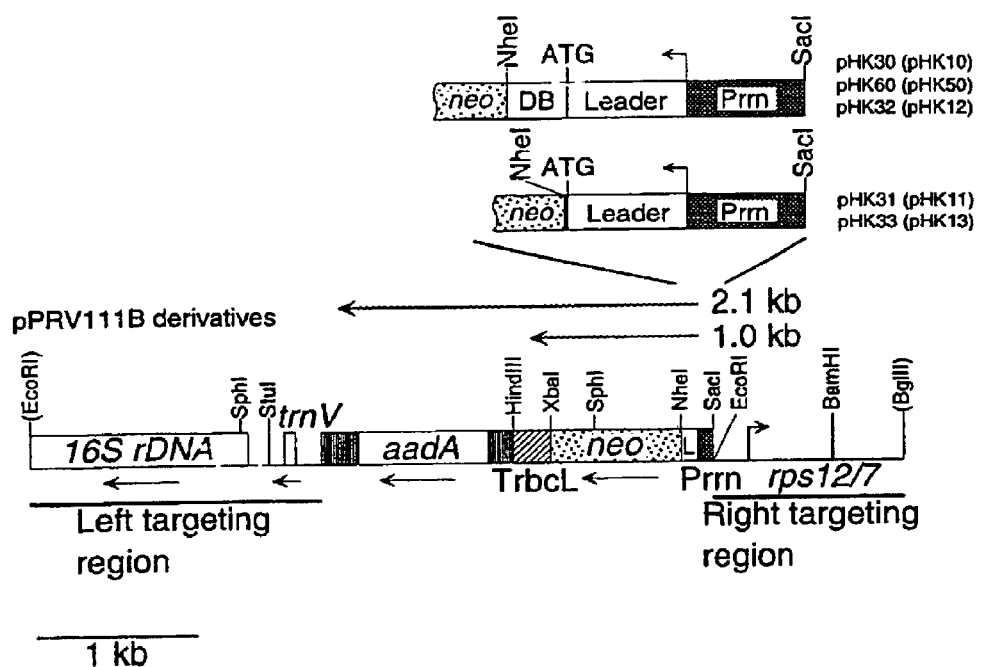

FIG. 4B. Plastid transformation vector pPRV111B with chimeric neo genes. See description of FIG. 4A. The promoter sequences are shown in FIG. 3A.

FIG. 5. Construction of Prrn promoter-plastid leader fragments by overlap extension PCR.

Figure 6:
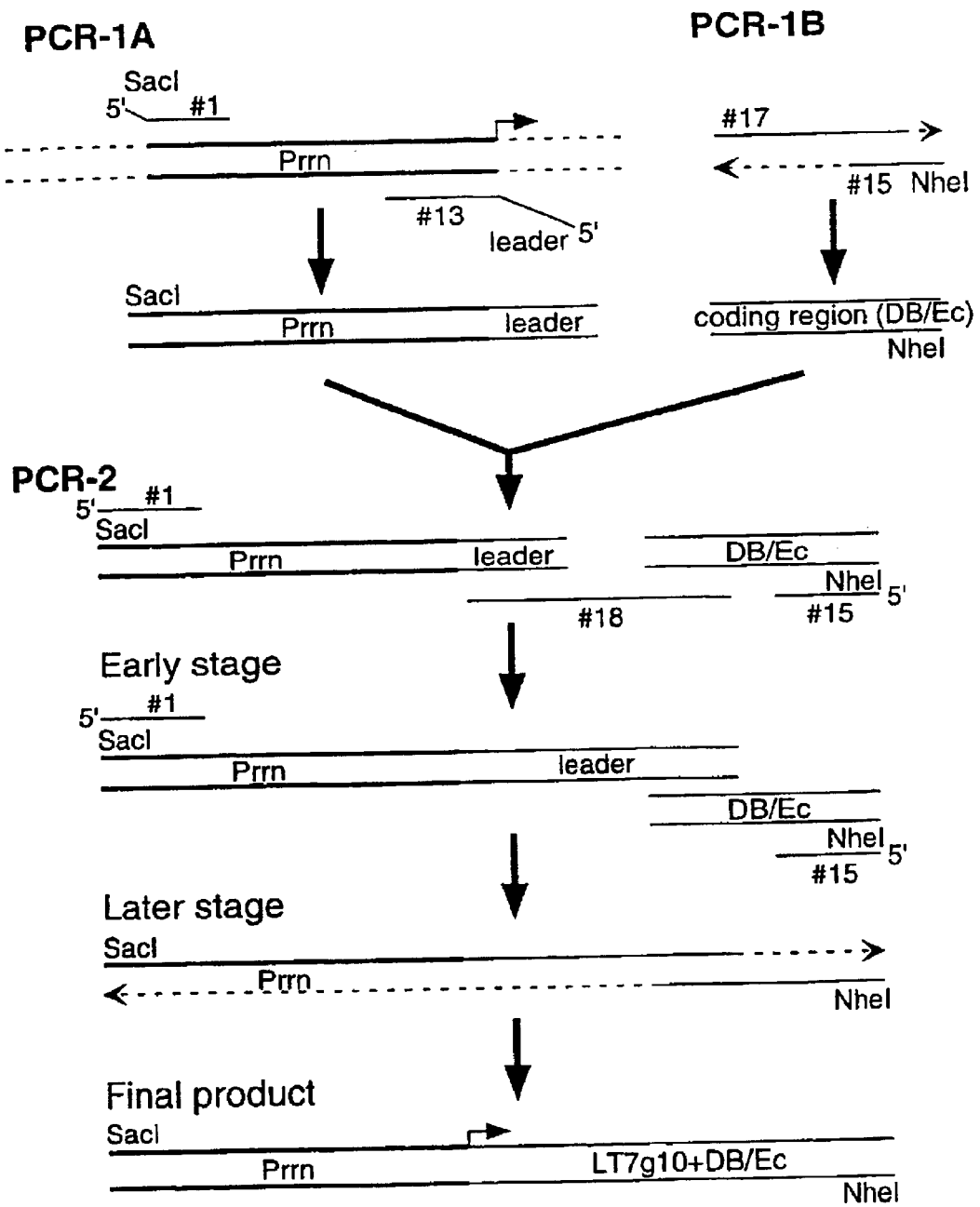

FIG. 6. Construction by the PCR of PrrnLT7g10+DB/Ec promoter (SacI-NheI fragment) in plasmid pHK18.

Figure 7:
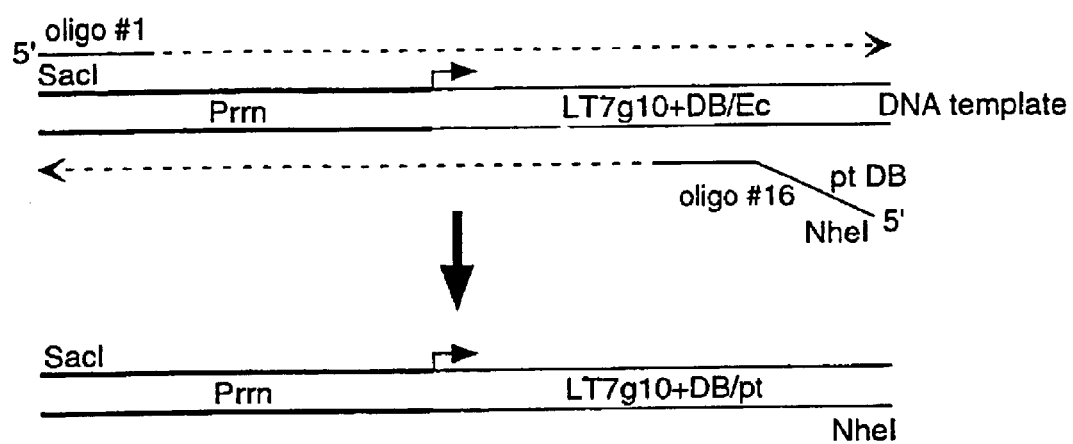

FIG. 7. Construction by PCR of the PrrnLT7g10+DB/pt promoter (SacI-NheI fragment) in plasmid pHK19.

Figure 8:
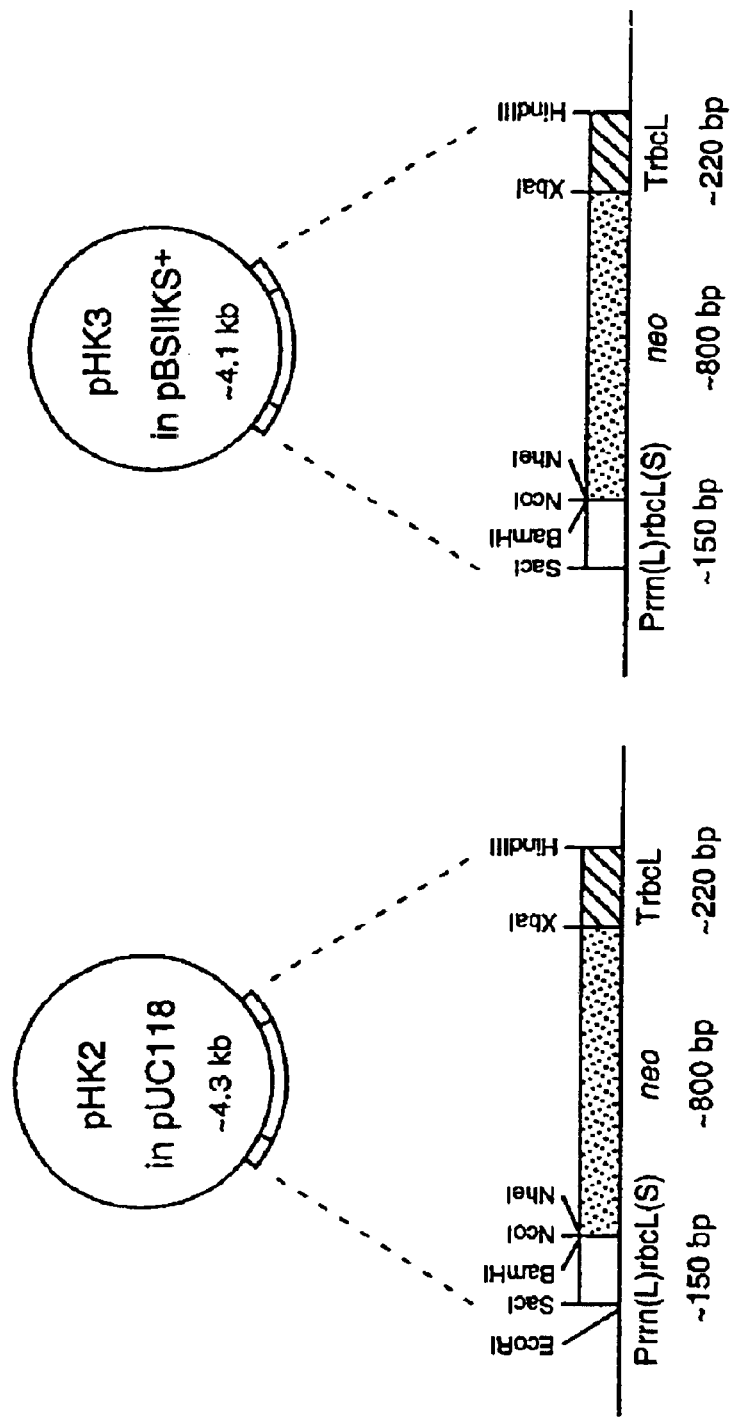

FIG. 8. Restriction map of plasmids pHK2 and pHK3 with the Prrn(L)rbcL(S)::neo::TrbcL gene. Restriction enzyme cleavage sites are marked for: BamHI, EcoRI, HindIII, NcoI, NheI, SacI, XbaI.

FIG. 9. DNA sequence of the Prrn(L)rbcL(S)::neo::TrbcL gene in plasmid pHK3 (SEQ ID NO: 17). Plasmid pHK2 carries an identical neo gene, except that there is an EcoRI site upstream of the SacI site.

Figure 10:
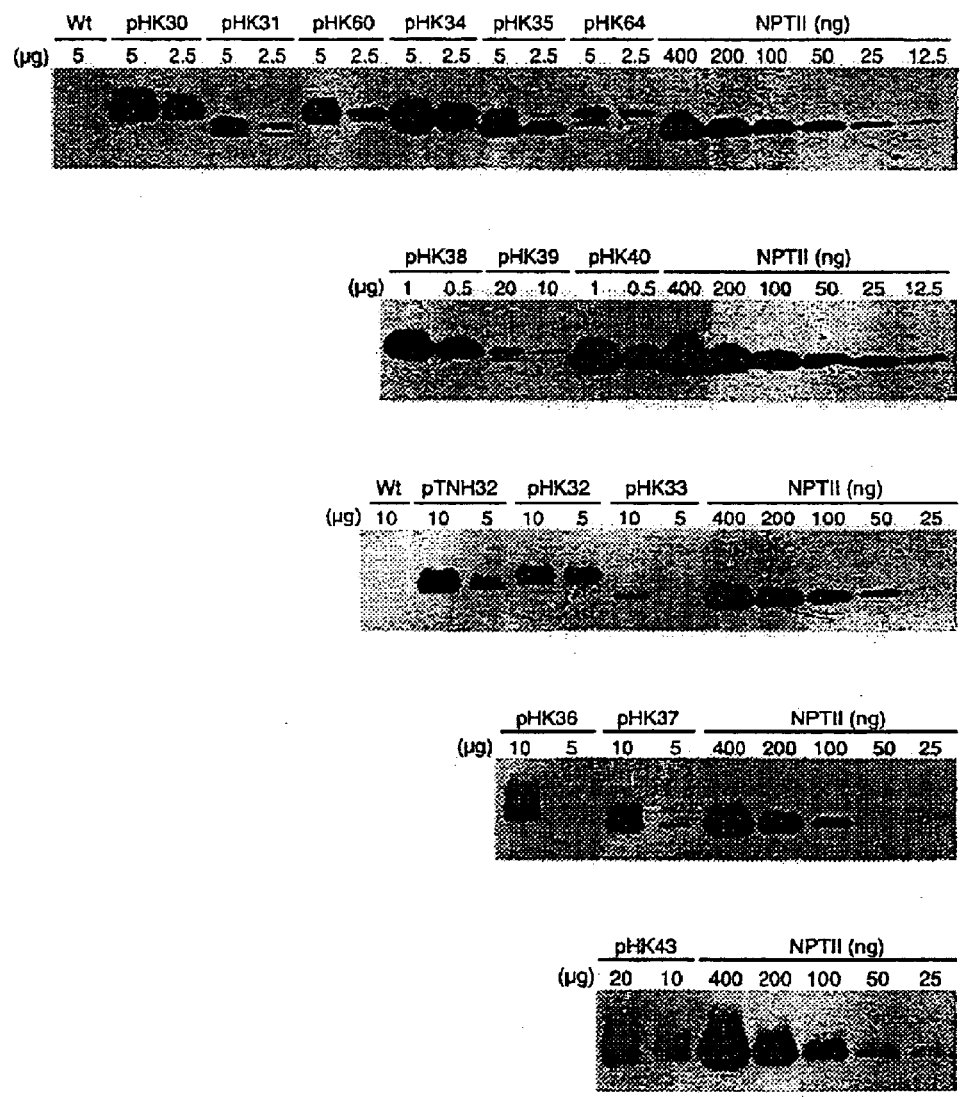

FIG. 10. NPTII accumulation in tobacco leaves detected by protein gel blot analysis. Amount of total soluble leaf protein ($\mu$g) loaded on SDS-PAGE gel is indicated above the lanes. Lanes are designated with plasmid used for plant transformation; $\mu$g protein loaded per lane is given below. NPTII standard and Nt-pTNH32 extracts were run as positive controls; extracts from wild-type non-transformed plants (wt) were used as negative controls.

Figure 11:
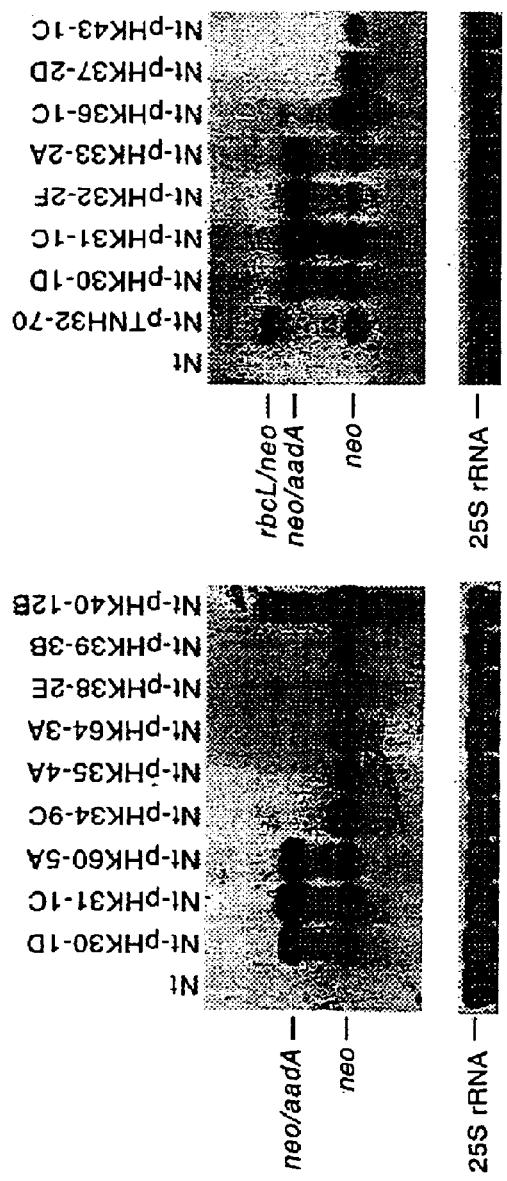

FIG. 11. The levels of neo mRNA in the transplastomic leaves. The blots were probed for neo (top) and cytoplasmic 25S rRNA as loading control (bottom). Positions of the monocistronic neo mRNA in vector pPRV111A (FIG. 4A), the monocistronic neo and dicistronic neo-aadA transcripts in vector pPRV111B (FIG. 4B) and the monocistronic neo and dicistronic rbcL-neo transcripts in pTNH32 transformed plants (Carrer et al., 1993) are marked. Lanes are designated with the transgenic plant serial number. 4 µg total cellular RNA was loaded per lane.

FIG. 12. Fraction of a codon encoding a particular amino acid and triplet frequency per 1000 codons in the mutagenized atpB and rbcL DB region (atpB wt: nucleotide sequence is nucleotides 1 through 42 of SEQ ID NO: 111, amino acid sequence is SEQ ID NO: 132; atpB m: nucleotide sequence is nucleotides 1 through 42 of SEQ ID NO: 112, amino acid sequence is SEQ ID NO: 132; rbcL wt: nucleotide sequence is nucleotides 1 through 42 of SEQ ID NO: 114, amino acid sequence is SEQ ID NO: 122; rbcL m: nucleotide sequence is nucleotides 1 through 42 of SEQ ID NO: 115, amino acid sequence is SEQ ID NO: 122; T7g10+DB/Ec: nucleotide sequence is SEQ ID NO: 123, amino acid sequence is SEQ ID NO: 124; T7g10+DB/pt: nucleotide sequence is SEQ ID NO: 125, amino acid sequence is SEQ ID NO: 126; T7g10–DB: nucleotide sequence is SEQ ID NO: 127, amino acid sequence is SEQ ID NO: 128). Altered nucleotides are in lower case.

Figure 13A:
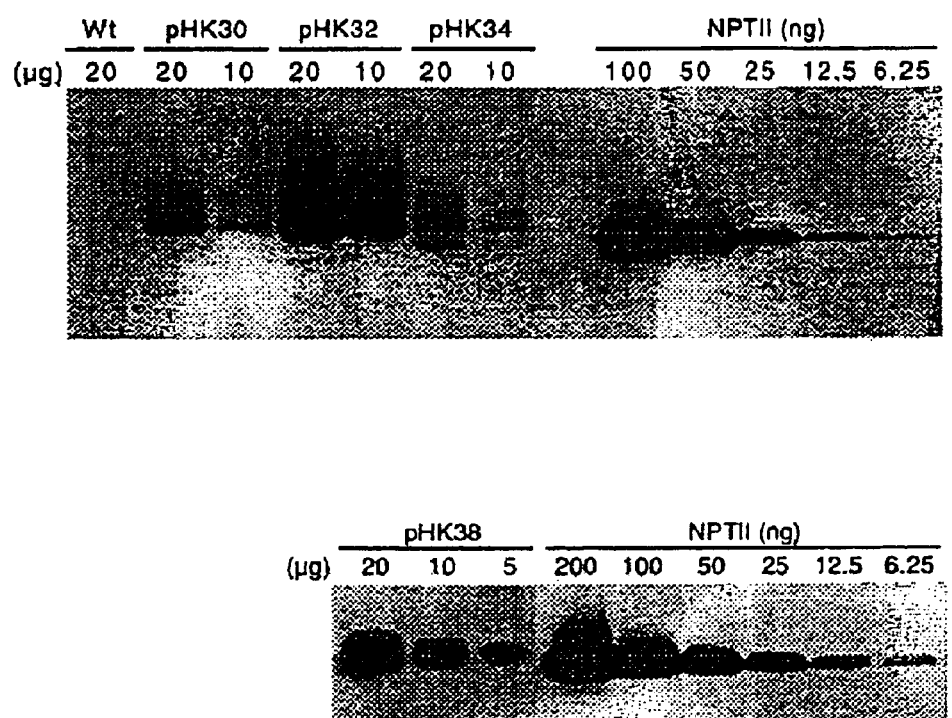

FIG. 13A. NPTII accumulation in tobacco roots detected by protein gel blot analysis. Lanes are designated with the plasmid used for plant transformation; µg protein loaded per lane is given below. NPTII standard was run as positive control; extracts from wild-type non-transformed plants (wt) were used as negative controls.

Figure 13B:
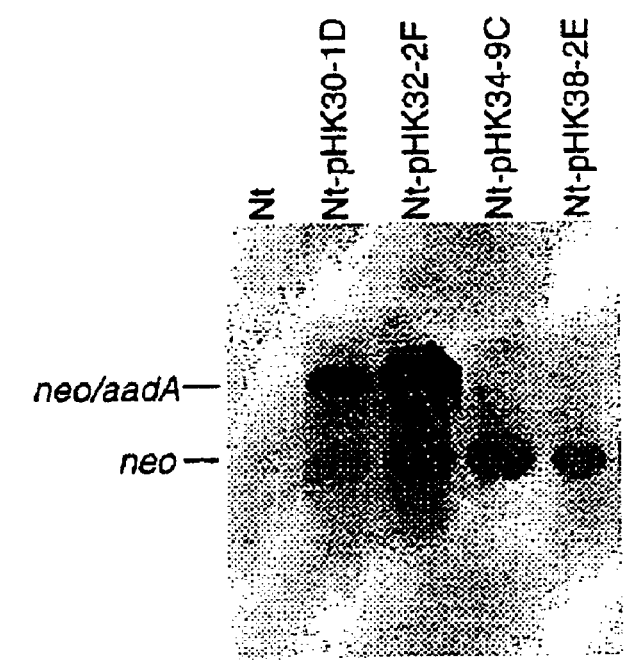

FIG. 13B. Steady-state levels of neo mRNA in tobacco roots. The neo probe detects a monocistronic mRNA in plants transformed with vector pPRV111A (FIG. 4A), and a monocistronic neo and a dicistronic neo-aadA transcript in plants transformed with vector pPRV111B (FIG. 4B). Lanes are designated with the transgenic plant serial number. 4 µg total cellular RNA was loaded per lane.

Figure 14:
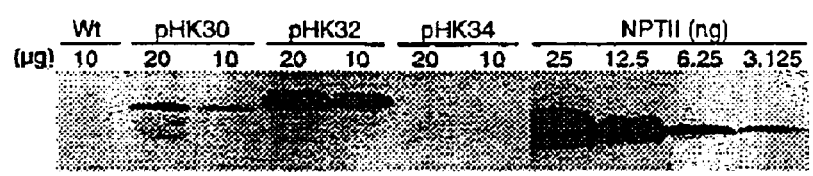

FIG. 14. Protein gel blot analysis to detect NPTII accumulation in tobacco seeds. Lanes are designated with plasmid used for plant transformation; µg protein loaded per lane is given below. NPTII standard was run as positive control; extracts from wild-type non-transformed plants (wt) were used as negative controls.

Figure 15A:
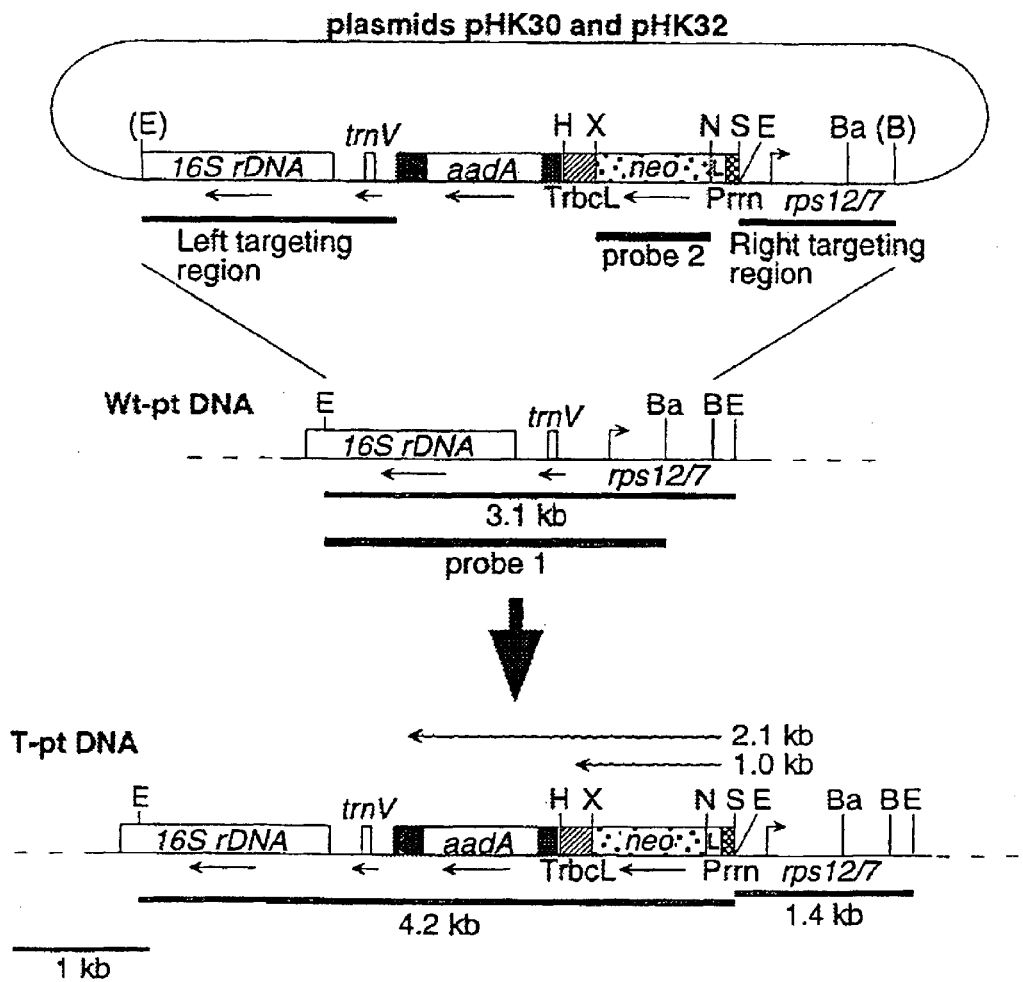

FIG. 15A. Diagram showing integration of the chimeric neo and aadA genes into the plastid genome by two homologous recombination events via the plastid targeting sequences (underlined). On top is shown a diagram of plasmids pHK30 and pHK32 are plastid transformation vector pPRV111B derivatives (Zoubenko et al., 1994). Horizontal arrows mark gene orientation. For description of chimeric neo genes, see FIG. 4B. 16SrDNA, trnV, rps12/7 are plastid genes (Shinozaki et al., 1986). The restriction sites marked for: EcoRI (E), SacI (S), NheI (N), XbaI (X), HindIII (H), BamHI (Ba) and BglII Restriction sites in brackets were eliminated during construction. In the middle the wild-type plastid DNA region (Wt-ptDNA) targeted for insertion is shown. Lines connecting plasmids and ptDNA mark sites of homologous recombination at the end of the vector plastid-targeting regions. The transformed plastid genome segment (T-ptDNA) map is shown on the bottom.

Figure 15B:
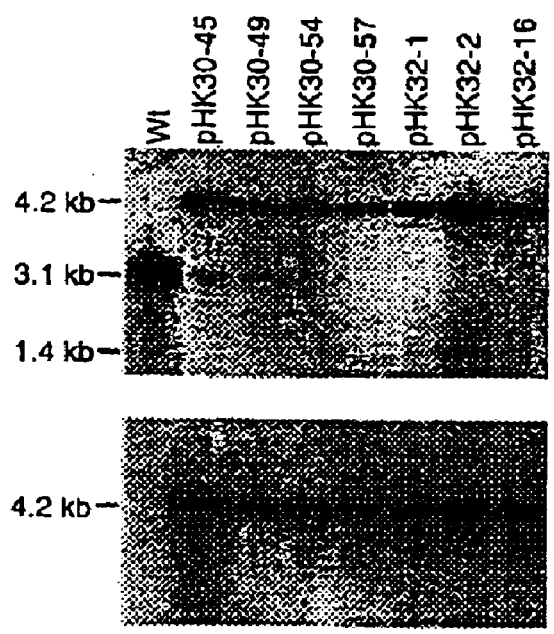

FIG. 15B. DNA gel blot analysis confirms of integration of the neo and aadA genes into the plastid genome. The blot on top was probed with the plastid targeting sequence (Probe 1 in FIG. 15A). It lights up 4.2-kb and 1.4-kb fragments in transplastomic lines, and a 3.1-kb fragment in wild-type (see FIG. 15A). Note that the 1.4-kb signal is week in most clones. The blot on the bottom was probed for neo sequences, which are present only in the transplastomic lines.

Figure 16A:
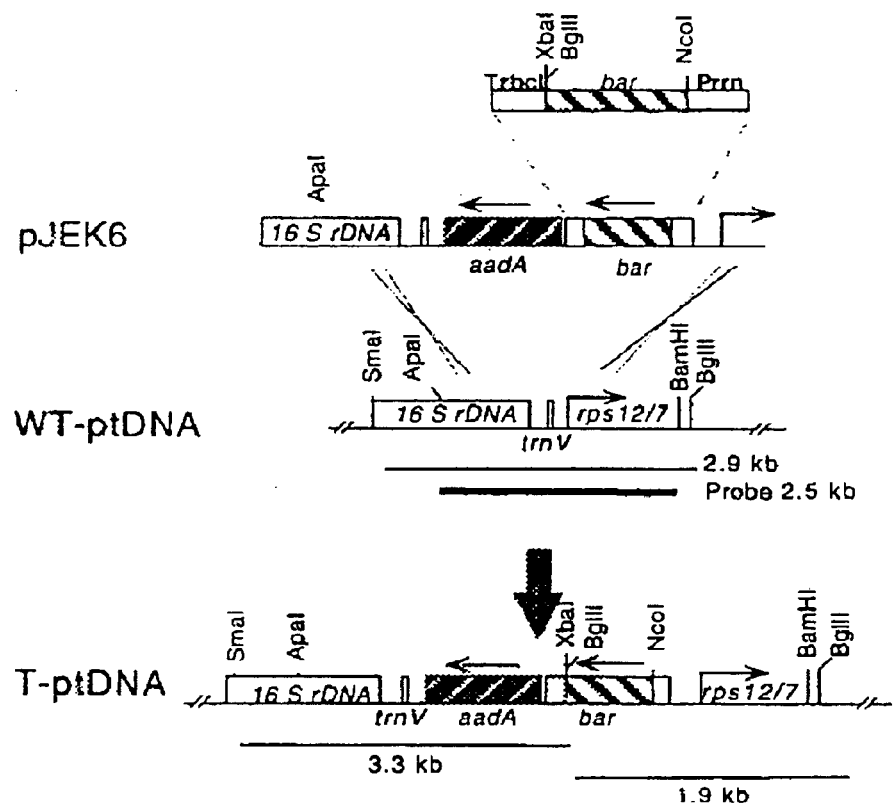

FIG. 16A. Diagram showing integration of the bar gene into the tobacco plastid genome. Map of the plastid targeting region in plasmid pJEK6 is shown on top. The targeted region of the wild-type plastid genome (wt-ptDNA) is shown in the middle. Integrated transgenes in the transplastome (T-ptDNA) are shown at the bottom. Map positions are shown for: the bar gene; aadA, the selectable spectinomycin resistance gene; 16SrDNA and rps12/7, plastid genes (Shinozaki et al., 1986). Arrows indicate direction of transcription. Map position of the probe (2.5 kb) is marked by a heavy line; the wild-type (2.9-kb) and transgenic (3.3-kb, 1.9-kb) fragments generated by SmaI and BglII digestion are marked by thin lines.

Figure 16B:
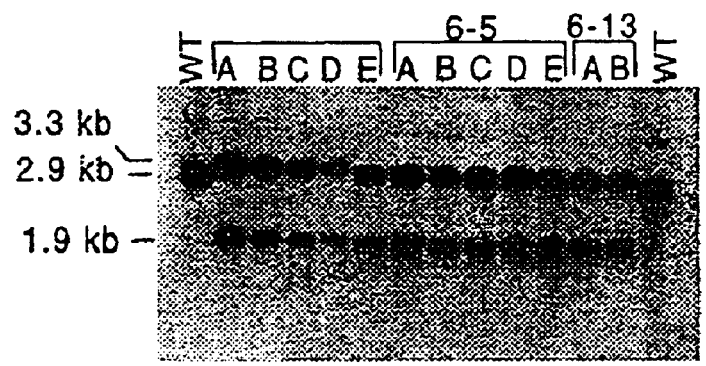

FIG. 16B. DNA gel blot confirms integration of bar into the tobacco plastid genome. Data are shown for transplastomic lines Nt-pJEK6-2A through E, Nt-pJEK6-5A through E and Nt-pJEK6-13A and B, and the wild-type parental line. SmaI-BglII digested total cellular DNA was probed with the 2.5-kb ApaI-BamHI plastid targeting sequence marked with heavy line in FIG. 16A.

Figure 17:
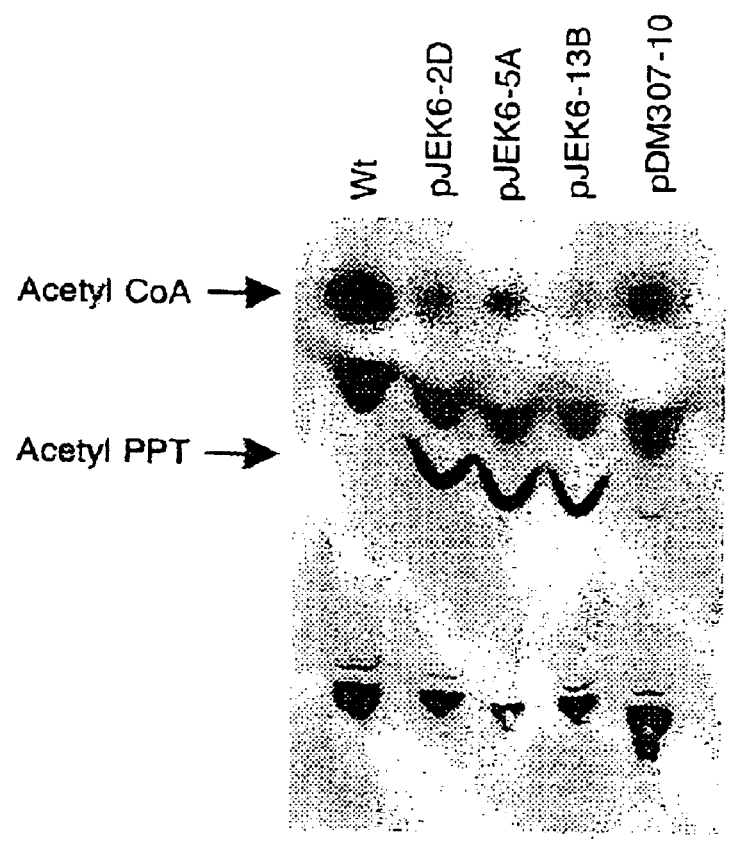

FIG. 17. PAT assay confirms bar expression in tobacco plastids. PAT activity was determined by conversion of PPT into acetyl-PPT using radiolabeled $^{14}$C-Acetyl-CoA. Data are shown for transplastomic lines Nt-pJEK6-2D, Nt-pJEK6-5A and Nt-pJEK6-13B, nuclear transformant Nt-pDM307-10 and wild-type (wt).

Figure 18A:

FIG. 18A. Transplastomic tobacco plants are herbicide resistant. Wild-type and pJEK6-transformed plants 13 days after Liberty spraying (5 ml, 2% solution).

Figure 18B:
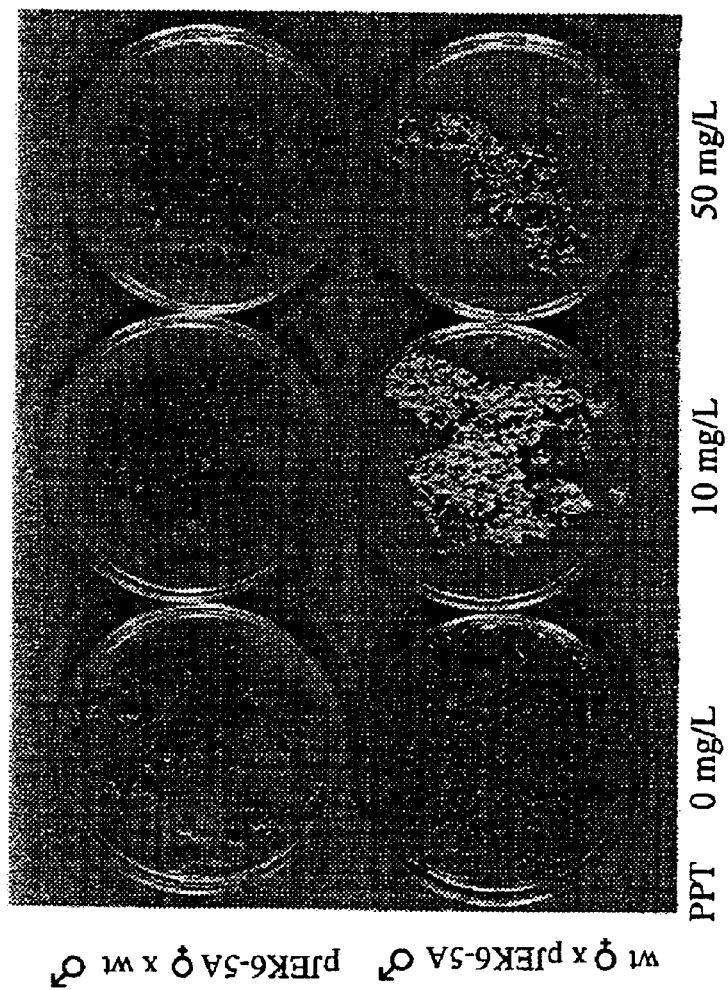

FIG. 18B. Maternal inheritance of PPT resistance in the seed progeny. Seeds from reciprocal crosses with Nt-pJEK6-5A plants germinated on 0, 10 and 50 mg/L PPT. wt×pJEK6-5A, transplastomic used as pollen parent; pJEK6-5A×wt, transplastomic line female parent. Resistant seedlings are green on PPT medium, sensitive seedlings are bleached.

FIG. 19. The engineered bacterial bar coding region DNA sequence in plasmid pJEK3 and pJEK6 (SEQ ID NO: 18) and encoded amino acid sequence (SEQ ID NO: 129). Nucleotides encoding the rbcL five N-terminal amino acids are in lower case. Nucleotides added at the 3' end during construction are also in lower case. NcoI, BglII and XbaI cloning sites are marked.

FIG. 20A. The synthetic bar gene DNA sequence (SEQ ID NO: 19) and the encoded amino acid sequence (SEQ ID NO: 130). The arginines encoded by AGA/AGG codons are in bold. Original nucleotides are in capital letters, altered bases are in lower case. Restriction sites used for cloning are marked.

FIG. 20B. The synthetic s2-bar gene DNA sequence (SEQ ID NO: 20) and the encoded amino acid sequence (SEQ ID NO: 130). The arginines encoded by AGA/AGG codons are in bold. Original nucleotides are in capital letters, altered bases are in lower case. Restriction sites used for cloning are marked.

Figure 21:
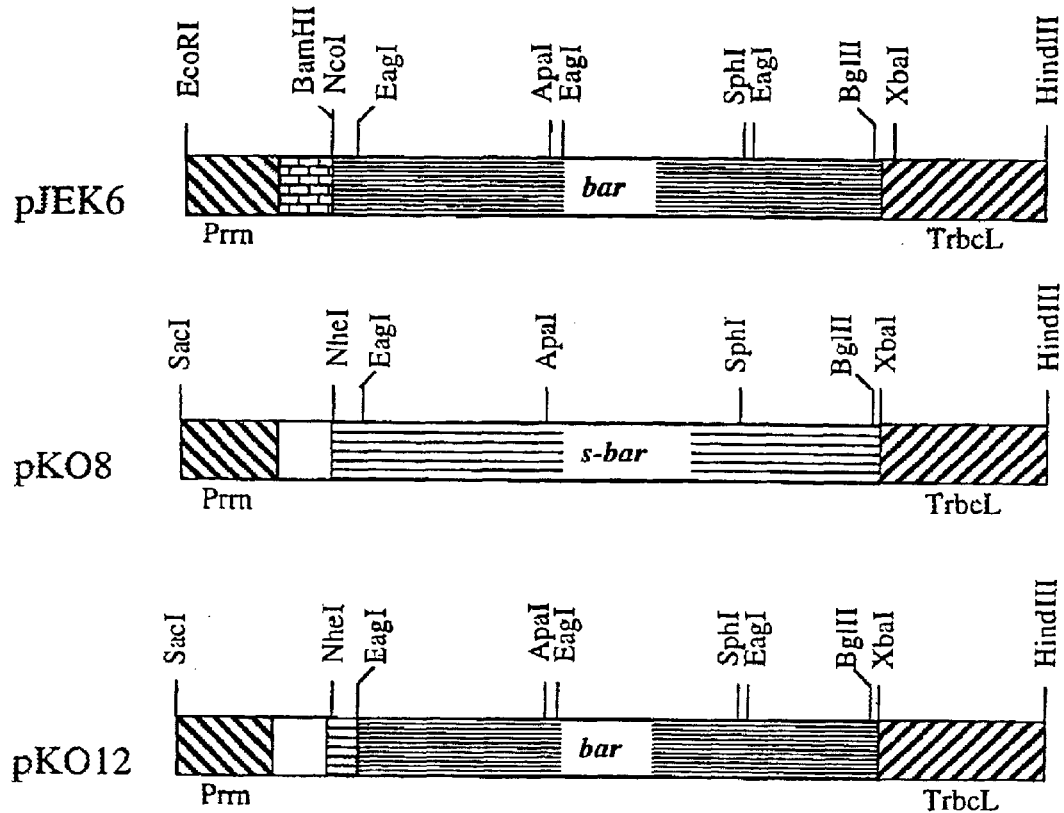

FIG. 21. Synthetic and bacterial bar genes. The bar coding region is expressed in the Prrn/TrbcL cassettes. Note that the Prrn promoters differ with respect to the translational control region.

Figure 22A:

FIG. 22A. PAT is expressed in E. coli from bar, but not from s-bar coding region. PAT activity was determined by conversion of PPT into acetyl-PPT using radiolabeled $^{14}$C-Acetyl-CoA. Data are shown for E. coli transformed with plasmids pJEK6 and pKO12 carrying the bar gene, and pKO8, carrying s-bar.

Figure 22B:

FIG. 22B. PAT assay confirms expression of bar and s-bar in tobacco plastids. PAT activity was determined by conversion of PPT into acetyl-PPT using radiolabeled $^{14}$C-Acetyl-CoA. Data are shown for transplastomic lines Nt-pJEK6-13B and Nt-pKO3-24a,B carrying bar and s-bar, respectively.

Figures 23A, 23B:
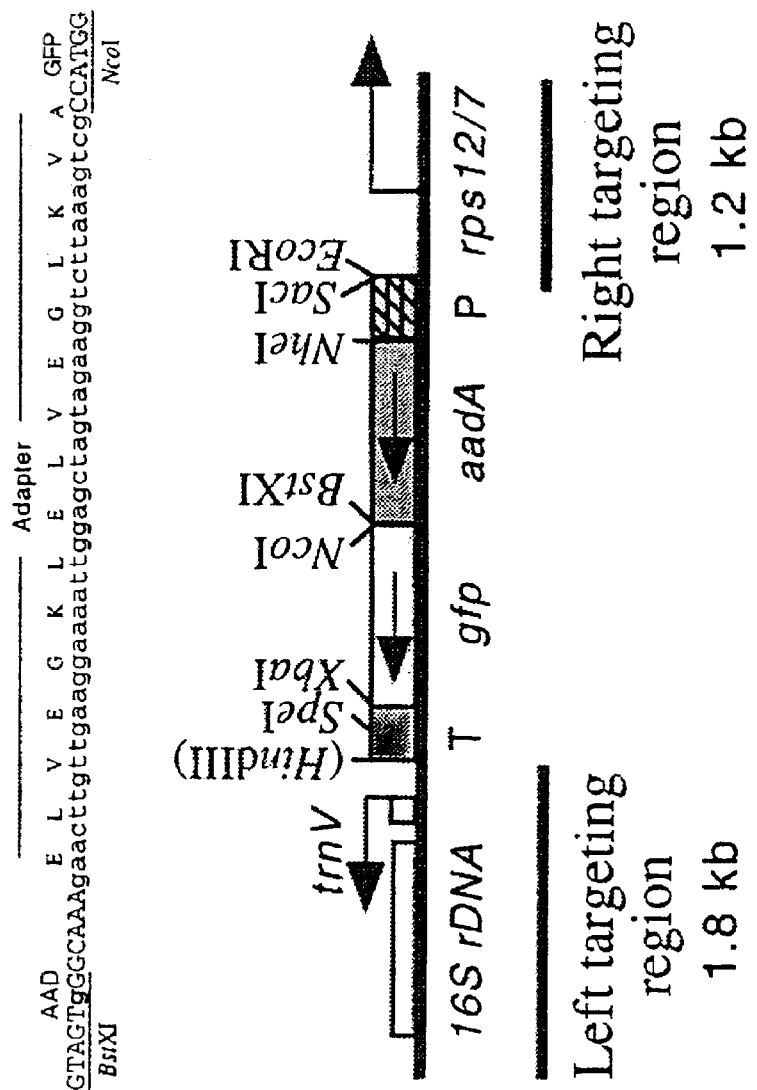

FIG. 23A. Plastid transformation vector with FLARE16-S as selectable marker targeting the plastid inverted repeat region. DNA (SEQ ID NO: 131) and protein (SEQ ID NO: 104) sequence at the aadA-gfp junction. Nucleotides derived from aadA and gfp are in capital, adapters sequences and the point mutation used to create the BstXI restriction site (bold) are in lower case.

FIG. 23B. Physical map of plastid transformation vector with FLARE16-S as selectable marker targeting the plastid inverted repeat region. Shown are: the promoter (P) and 3'UTR (T) of the aadA16pt-gfp coding region and its component parts (aadA and gfp coding regions); rrn16 and rps12/7 plastid genes; restriction endonuclease sites HindIII (removed), SpeI, XbaI, NcoI, BstXI, NheI, EcoRI. In plasmid pMSK56 aadA16pt-gfp is expressed from the Prrn:LatpBDB promoter and encodes FLARE16-S1. In plasmid pMSK57 aadA16pt-gfp is expressed from the Prrn.LrbcLDB promoter and encodes FLARE16-S2.

FIG. 24. Localization of FLARE16-S to tobacco plastids by laser scanning confocal microscopy in heteroplastomic tissue. Images were processed to detect FLARE16-S (green) and chlorophyll fluorescence (red) and both in a merged view. Sections are shown from plants expressing FLARE16-S1 (a,b) and FLARE16-S2 (3c–f). Note wild-type and transformed plastids in leaves (3a,c,d), chromoplasts of petals (3b), trichomes (3e) and non-green root plastids (f). White arrows mark transplastomic organelles. Bars represent 25 µm.

Figure 25:
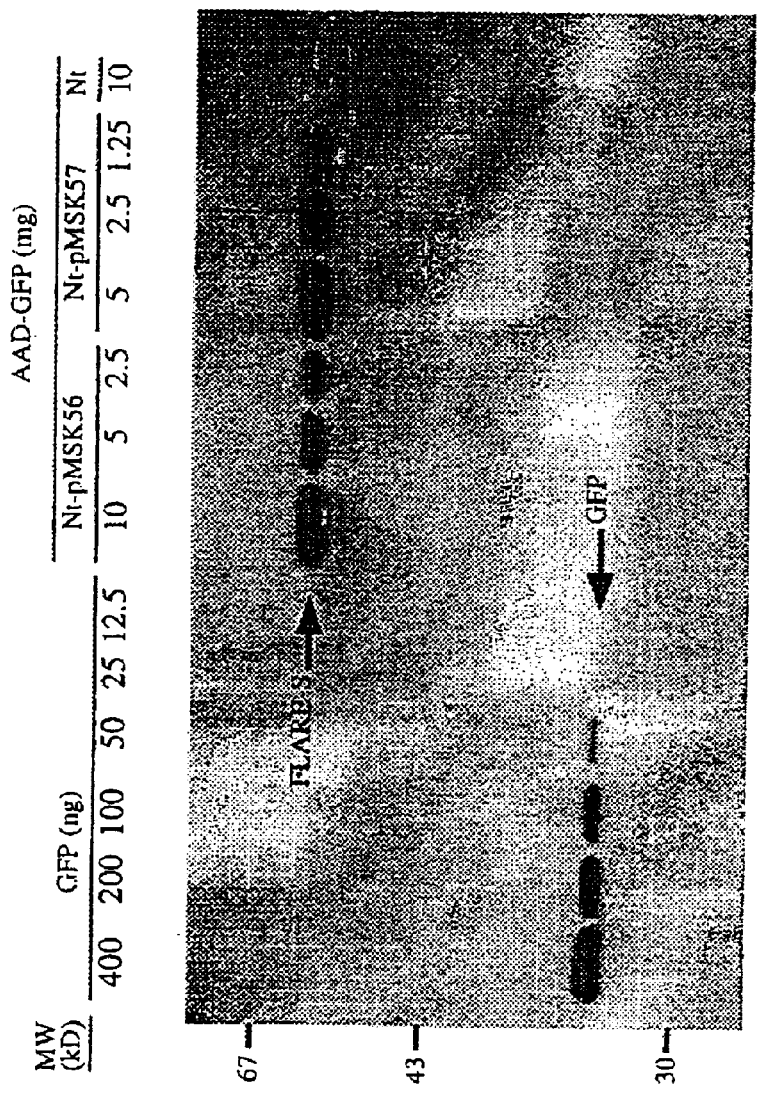

FIG. 25. Immunoblot analysis of FLARE16-S accumulation in chloroplasts. The amount of loaded protein (µg) is indicated above the lanes. Quantification of FLARE16-S1 (Nt-pMSK56 plants) and FLARE16-S2 (Nt-pMSK57 plants) is based on comparison with a purified GFP dilution series. Extract from a wild-type plant (Nt) was used as negative control.

Figure 26A:
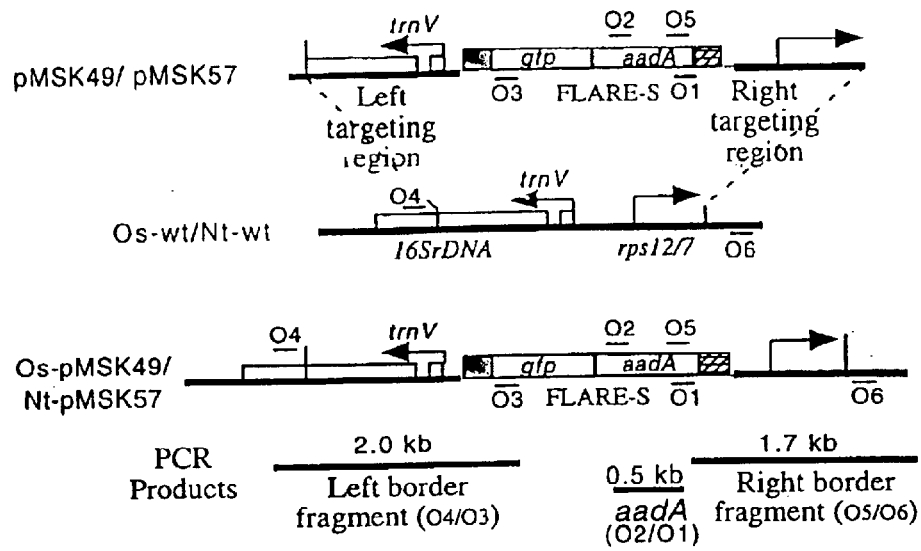

FIG. 26A. Amplification of border fragments confirms integration of FLARE-S genes into the plastid genome. Maps of the plastid targeting regions of the rice (pMSK49) and tobacco (pMSK57) vectors, the segment of the rice and tobacco plastid genomes targeted by the vectors (O-wt and Nt-wt), and the same regions after integration of FLARE-S genes. The ends of plastid targeting regions are connected with cognate sequences in the wild-type plastid genome. Plastid genes 16SrDNA, trnV and rps12/7 are marked only in the wild-type plastid genomes. The position of PCR primers (O1–O6) and the PCR fragments generated by them are also shown.

Figure 26B:
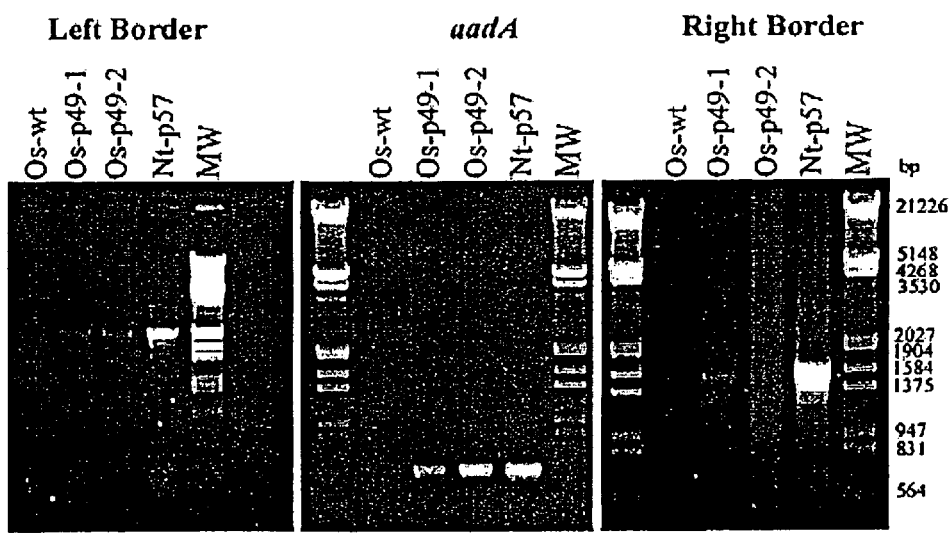

FIG. 26B. Amplification of border fragments confirms integration of FLARE-S genes into the plastid genome. Gels with PCR-amplified left and right border fragments, and with aadA fragment. Results are shown for rice (Os-pMSK49-1 and Os-pMSK49-2) and tobacco (Nt-pMSK57) transplastomic lines and wild-type (Os-wt) rice. The molecular weight markers is EcoRI- and HindIII-digested λ DNA.

Figure 27:
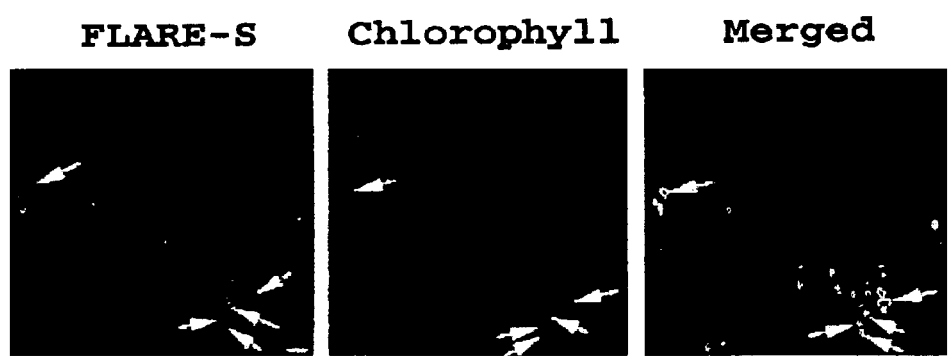

FIG. 27. Localization of FLARE11-S3 to rice chloroplasts in the Os-pMSK49-5 line by laser scanning confocal microscopy. Images were processed to detect FLARE11-S (green) and chlorophyll fluorescence (red) and both in a merged view. Arrows point to mixed populations of plastids in cells. Bar represents 25 µm.

FIG. 28. The sequence of FLARE16-S is shown (SEQ ID NO: 21).

FIG. 29. The sequence of FLARE16-S1 is shown (SEQ ID NO: 22).

FIG. 30. The sequence of FLARE16-S2 is shown (SEQ ID NO: 23).

FIG. 31. The sequence of FLARE11-S3 is shown (SEQ ID NO: 24).

FIG. 32. The sequence of FLARE11-S3 is shown (SEQ ID NO: 25).

FIGS. 33A and 33B. The sequence of pMSK35 is shown (SEQ ID NO: 26).

FIGS. 34A and 34B. The sequence of pMSK49 is shown (SEQ ID NO: 27).

FIG. 35. A table describing the FLARE constructs of the invention.

DETAILED DESCRIPTION OF THE INVENTION

Figure 1A:
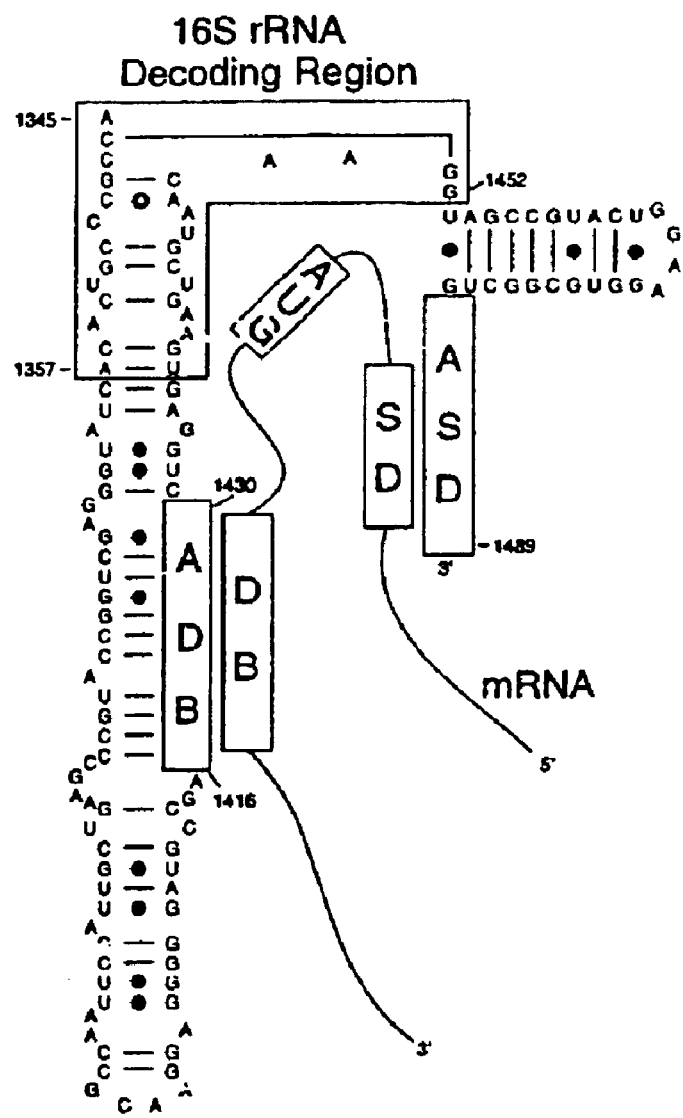
FIG. 1A. Plastid mRNAs and the small (16S) ribosomal RNA contain complementary sequences downstream of AUG implicating interactions between mRNA and 16S rRNA during translation initiation in plastids. Proposed model is based on data in *E. coli* (Sprengart et al., 1996); for sequence of 16S rRNA (SEQ ID NO: 108) see ref. (Shinozaki et al., 1986b). SD, Shine-Dalgarno sequence; ASD, anti SD region; DB, downstream box; ADB, anti DB region. Watson-Crick (line) and G-U (closed circle) pairing are marked.
Figure 1B:
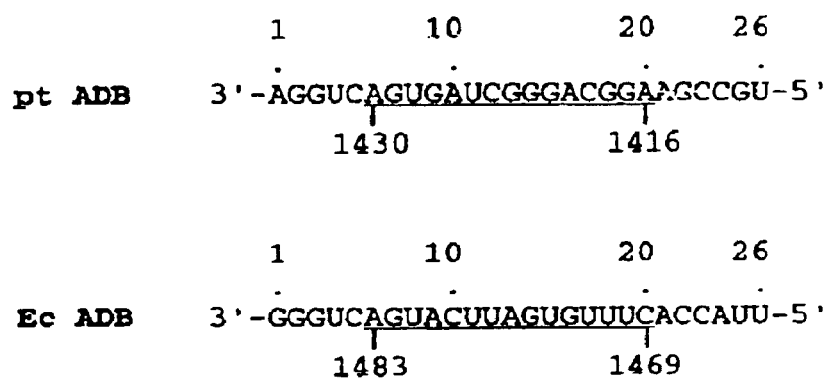
FIG. 1B. Sequence of the anti-downstream-box regions (ADB sequence underlined) of the 16S rRNA in plastids (pt; SEQ ID NO: 109; this application) and in *E. coli* (Ec; SEQ ID NO: 110; Sprengart et al., 1996). The *E. coli* ADB box contains sequences between nucleotides 1469–1483 of the 16S rRNA (Sprengart et al., 1996), corresponding to nucleotides 1416–1430 of the tobacco 16S rRNA (Dams et al., 1988; sequence between nucleotides 104173–104187 in Shinozaki et al., 1986).

DNA cassettes for high level protein expression in plastids are provided herein. Higher plant plastid mRNAs contain sequences within 50 nt downstream of AUG that are complementary to the 16S rRNA 3-region. These complementary sequences are approximately at the same position as DB sequences in *E. coli* mRNAs. See FIGS. 1A and 2A. Interestingly, the tentative plastid DB sequence significantly deviates from the *E. coli* DB consensus, since the tobacco plastid and *E. coli* 16S rRNA sequence in the anti-downstream-box (ADB) region is significantly different (FIG. 1B). The feasibility of improving protein expression by incorporating DB sequences in plastids was assessed by constructing a series of chimeric 5' regulatory regions consisting of the plastid rRNA operon $\sigma^{70}$-type promoter (Prrn-114; Svab and Maliga, 1993; Vera and Sugiura, 1995) and the leader sequence of plastid mRNAs with the native DB, mutagenized DB and synthetic DB sequences. The plastid mRNA leaders differ with respect to the presence and position of the SD sequence. Translation efficiency from the chimeric promoters was determined by expressing the bacterial neo gene in plastids. The neo (or kan) gene encodes neomycin phosphotransferase (NPTII) and confers resistance to kanamycin in bacteria and plastids (Carrer et al., 1993). We have found that NPTII from the chimeric neo transcripts accumulates in the range of 0.2% to 23% of the total soluble leaf protein, indicating the importance of translational control signals in the mRNA 5' region for high-level protein expression.

There is great interest in producing recombinant proteins in plants plastids which, thus far have been expressed from nuclear genes only (Arntzen, 1997; Conrad and Fiedler, 1998; Kusnadi et al., 1997). Protein levels produced from the PrrnLrbcL+DBwt and PrrnLT7g10 expression cassettes described here significantly exceed protein levels reported for nuclear genes. Accumulation of NPTII from nuclear genes is typically <<0.1% (Allen et al., 1996), the highest value being 0.4% of the total soluble protein (Houdt et al., 1997). We reported earlier accumulation of 1% NPTII from a plastid neo transgene (Carrer et al., 1993). Other examples for protein accumulation from plastid transgenes are 2.5% β-glucuronidase (GUS) (Staub and Maliga, 1993)) and 3–5% of the *Bacillus thuringiensis* (Bt) crystal toxins (McBride et al., 1995). As compared to this earlier report, we have achieved a significant increase in NPTII levels, up to 23% of total soluble protein.

FLARE-S, a protein obtained by fusing an antibiotic-inactivating enzyme with the *Aeguorea victoria* green fluorescence protein accumulated to 8% and 18% of total soluble protein from the PrrnLatpB+DBwt and PrrnLrbcL+DBwt cassettes provided herein. See Example 8. High-level protein accumulation from the cassettes of the present invention can be clearly attributed to engineering the translational control region (TCR) of the chimeric genes. These novel genetic elements may be used in different applications to drive expression of proteins with agronomic, industrial or pharmaceutical importance.

There is a strong demand for methods that control the flow of transgenes in field crops. Incorporation of the transgenes in the plastid genome rather than the nuclear genome results in natural transgene containment, since plastids are not transmitted via pollen in most crops (Maliga, 1993). Plastid transformation in crops has not been widely employed due to the lack of technology. Enhanced expression of selective markers should yield higher transformation efficiencies. The chimeric promoters of the present invention facilitate extension of plastid transformation to agronomically and industrially important crops. Indeed, high-level expression from the PrrnLatpB+DBwt cassette described here resulted in ~25-fold increase in the frequency of kanamycin-resistant transplastomic tobacco lines. More importantly, high levels of marker gene expression following plastid transformation have been obtained in rice, the first cereal species in which plastid transformation has been successful. The results are set forth in Example 8.

The following examples are provided to illustrate various embodiments of the present invention. They are not intended to limit the invention in any way.

The protocols set forth below are provided to facilitate the practice of the present invention.

Preparation of Chimeric 5' Cassettes for Elevated Expression of Heterologous Proteins in Plastids of Higher Plants Identification of a Potential Downstream Box in Plastid mRNAs The presence or absence of downstream box elements in mRNA molecules was determined for the following genes: psbB (Tanaka et al., 1987) and psbA (Sugita and Sugiura, 1984), photosystem II genes; rbcL, encoding the large subunit of ribulose-1,5-bisphosphate carboxylase/oxygenase (Shinozaki and Sugiura, 1982); atpB, encoding the ATPase β subunit (Orozco et al., 1990); and clpP, encoding the proteolytic subunit of the Clp ATP-dependent plastid protease (Hajdukiewicz et al., 1997). Interestingly, most or all of the PclpP-53 promoter is downstream of the transcription initiation site, therefore the PrrnLclpP constructs are assumed to contain two promoters: Prrn-114 and PclpP-53. Transcription initiation sites for these genes were described in references cited above; for nucleotide position of the genes in the plastid genome see Shinozaki et al., 1986.

Figure 2A:
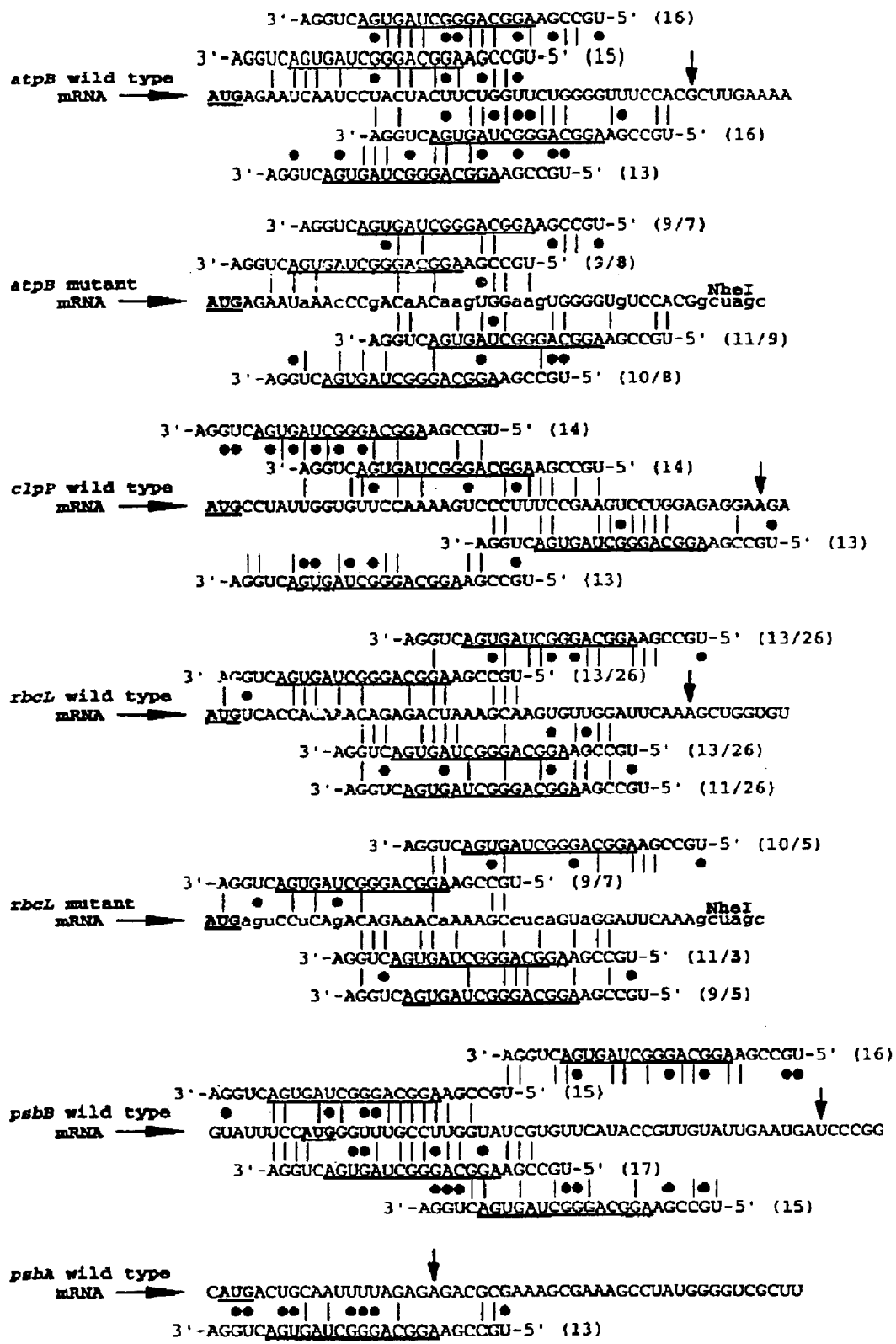
FIG. 2A. Base-pairing between plastid ADB (SEQ ID NO: 109) and wild type atpB (SEQ ID NO: 111), mutant atpB (SEQ ID NO: 112), clpP (SEQ ID NO: 113), wild type rbcL (SEQ ID NO: 114), mutant rbcL (SEQ ID NO: 115), psbB (SEQ ID NO: 116) and psbA (SEQ ID NO: 117) mRNAs (underlined). Multiple alternative DB-ADB interactions are shown. Nucleotides changed to reduce or alter mRNA-rRNA interaction are in lower case. The number of potential nucleotide pairs formed with the 26 nt ADB region is in parenthesis. The number of pairing events affected by mutagenesis is in bold.

Initially, it was assumed that the plastid ADB is similar in size and position as the *E. coli* ADB in the 16S rRNA. The *E. coli* ADB is localized on a conserved stem structure between nucleotides 1469 to 1483 (15 nt) that corresponds to nucleotides 1416 and 1430 of the plastid 16S rRNA (Dams et al., 1988; Sprengart et al., 1996). Although in both cases, the ADB is contained in the 16S rRNA penultimate stem, the actual ADB sequence is different in plastids and in *E. coli* (FIG. 1B). The N-terminal coding regions of plastid genes atpB, clpP, rbcL, petA, psaA, psbA, psbB, psbD and psbE were searched for potential DB sequences. The homology search was carried out with a 26 nucleotide sequence centered on the tentative DB region (FIG. 1B). The search revealed short stretches of imperfect homology with alternative solutions. Since the position of DB in the mRNA is quite flexible (Etchegaray and Inouye, 1999), we show four potential DB-ADB interactions for atpB and rbcL in FIG. 2A. Two plastid mRNAs were selected to test the role of DB in the translation of plastid mRNAs: 1) atpB mRNA lacks a SD sequence; and 2) rbcL mRNA contains a SD sequence at the prokaryotic consensus. In addition, the phage T7 gene 10 (T7g10) leader was included in the study. This leader has a well-characterized *E. coli* DB sequence (FIG. 2B; Sprengart et al., 1996). Additional plastid mRNAs with potential DB sequences shown in FIG. 2A are clpP, psbB and psbA.

Experimental Strategy to Test the Efficiency of Leader Sequences for Translation To compare the efficiency of translation from the 5'-UTR of the selected genes, the 5'-UTR was cloned downstream of the strong plastid rRNA operon $\sigma^{70}$-type promoter (Prrn-114) (Svab and Maliga, 1993; Allison et al., 1996), which initiates transcription from multiple adjacent nucleotides (−114, −113, −111; Sriraman et al., 1998). The promoter fragments were constructed as SacI-NheI or a SacI-NcoI fragments. Construction of the chimeric promoters using conventional molecular biological techniques is set forth in detail in the next section.

Two constructs were prepared for each 5'-UTR selected: one with (+DB) and one without (−DB) a native downstream box. It will be obvious from the forthcoming discussion, that the −DB constructs have a synthetic DB provided by the NheI restriction site. The promoters were cloned upstream of the coding region of a kanamycin resistance (neo) gene, which is available on an NheI-XbaI or NcoI-XbaI fragment. For the stabilization of the mRNA, the rbcL gene 3'-untranslated region was cloned downstream of neo as an XbaI-HindIII fragment. The chimeric neo genes can therefore be excised from the pUC118 or pBSIIKS+ plasmids as SacI-HindIII fragments. These source plasmids are listed in Table 1.

TABLE 1

Salient features of chimeric promoters[a.]

| Source of 5'-UTR (nucleotides from AUG) | SD | DB | Promoter fragment | pUC118(U) or pBSIIKS⁺ (B) | pPRV111A,B |
|---|---|---|---|---|---|
| atpB (−90/+42) | − | wt | SacI/NheI | pHK10 (U) | pHK30 (B) |
| atpB (−90/+6) | − | s | SacI/NneI | pHK11 (U) | pHK31 (B) |
| atpB (−90/+42) | − | m | SacI/NheI | pHK50 (B) | pHK60 (B) |
| clpP (−53/+48) | − | wt | SacI/NheI | pHK12 (U) | pHK32 (B) |
| clpP (−53/+6) | − | s | SacI/NheI | pHK13 (U) | pHK33 (B) |
| rbcL (−58/+42) | + | wt | SacI/NheI | pHK14 (B) | pHK34 (A) |
| rbcL (−58/+6) | + | s | SacI/NheI | pHK15 (U) | pHK35 (A) |
| rbcL (−58/+42) | + | m | SacI/NheI | pHK54 (B) | pHK64 (A) |
| psbB (−54/+45) | + | wt | SacI/NheI[d] | pHK16 (U) | pHK36 (A) |
| psbB (−54/+3) | + | s | SaCI/NCoI[d] | PHK17 (U) | pHK37 (A) |
| [b]T7g10+DB/Ec (−63/+24) | + | Ec | SacI/NheI | pHK18 (B) | pHK38 (A) |
| [b]T7g10+DB/pt (−63/+24) | + | pt | SacI/NheI | pHK19 (B) | pHK39 (A) |
| T7g10−DB (−63/+9) | + | s | SacI/NheI | pHK20 (B) | pHK40 (A) |
| psbA (−85/+21) | − | wt | SacI/NheI | pHK21 (U) | pHK41 (A) |
| psbA (−85/+3) | − | s | SacI/NcoI[e] | pHK22 (U) | pHK42 (A) |

TABLE 1-continued

Salient features of chimeric promoters[a]

| Source of 5'-UTR (nucleotides from AUG) | SD | Promoter DB fragment | pUC118(U) or pBSIIKS+ (B) | pPRV111A,B |
|---|---|---|---|---|
| [c]psbA(+GC) (−85/+3) | — | sSacI/ NcoI[e] | pHK23 (U) | pHK43 (A) |

[a]SD+, SD at prokaryotic consensus position; SD−, no SD at prokaryotic consensus position;
DB wt, wild-type;
m, mutants;
s, NheI site as synthetic DB.
[b]Ec or pt refers to construct with *E. coli* or plastid DB sequence.
[c]psbA(+GC) indicates addition of GC to the wild-type A at the mRNA 5'-end.
[d]In source gene psbB translation initiation codon is within NcoI site; therefor +DB construct pHK16 has this NcoI site upstream of the NheI site; see FIG. 9.
[e]Translation initiation codon is included in NcoI site; NheI site is directly downstream in kan coding region; see FIG. 8.

The Prrn promoter fragment is available in plasmid pPRV100A (Zoubenko et al., 1994). The promoters were designed to include sequences between −197 nt and −114 nt upstream of the mature 16S rRNA 5' end. Nucleotide −197 is the 5'-end of the Prrn promoter constructs utilized for these and other studies (Svab and Maliga. 1993; −1 is the first nucleotide upstream of the mature 16S rRNA). The G at the −114 position is one of three transcription initiation sites; the other two are the adjacent C (−113) and A (−111) nucleotides (Allison et al., 1996, Sriraman et al., 1998). The nucleotide at which Prrn transcription would initiate is marked by a filled circle in FIGS. 3A–D. In most constructs, this is a G (−114) as in the native promoter. Ir two constructs the G was replaced by an A, as in the psbA promoter which is the source of the leader sequence (pHK21, pHK22; see below).

Design of the 5' Leader from atpB

For the atpB gene, multiple mRNA 5'-ends were mapped in tobacco leaves including at least four primary transcripts indicating transcription from four promoters and a processed 5'-end 90 nucleotides upstream of the translation initiation codon (Orozco et al., 1990). The terminal nucleotide of the processed atpB 5'-end is a G. Therefore, the chimeric PrrnLatpB promoters were designed to initiate transcription at a G, anticipating that the leader sequence of the chimeric transcript will be a perfect reproduction of the processed atpB mRNA 5'-end. Out of the atpB coding region, 42 and 6 nucleotides are included in the +DBwt and −DB constructs, respectively. The 42 nucleotides include four potential DB sequences shown in FIG. 2A. Two point mutations in the leader sequence were designed to eliminate NheI (T to A) and EcoRI (G to A) restriction sites without affecting the predicted mRNA 5' secondary structure. In the −DB constructs, two codons (6 nucleotides) were retained from the native coding region upstream of the NheI restriction site (GCTAGC sequence) in which the stop codon is out-of-frame (FIG. 3A). Eleven silent point mutations were introduced in the DB region of the PrrnLatpB+DBm construct to either minimize the number of base pairs, or to change the nature of base pairing (for example G-C to G-U) (FIG. 2A; FIG. 3A).

Design of the 5' Leader from clpP

Two major mRNA 5'-ends of the clpP gene were mapped in tobacco leaves (Hajdukiewicz et al., 1997). The terminal nucleotide of the proximal primary transcript is a G. Therefore, the chimeric PrrnLclpP promoters were designed to initiate transcription at a G, anticipating that the leader sequence of the chimeric transcript will be a perfect reproduction of the leader transcribed from the Pclp-53 NEP promoter. Out of the clpP coding region, 48 and 6 nucleotides are retained in the +DBwt and −DB constructs, respectively. The 48 nucleotides include four potential DB sequences as shown in FIG. 2A. In the −DB constructs, two codons (6 nucleotides) were retained from the native coding region upstream of the NheI restriction site (GCTAGC sequence) in which the stop codon is out-of-frame.

Design of the 5' Leader from rbcL

One primary and one processed mRNA 5'-end were mapped in tobacco leaves for the rbcL gene (Shinozaki and Sugiura, 1982). The terminal nucleotide of the processed 5' end is a T. The chimeric PrrnLrbcL promoters were designed to initiate transcription at a G, one nucleotide downstream of the terminal T. Forty-two and 6 nucleotides out of the rbcL coding region are included in the +DB and −DB constructs, respectively. The 42 nucleotides include four potential DB sequences as shown in FIG. 2A. The one point mutation (G to A) in the leader sequence was designed to eliminate an EcoRI restriction site without affecting the predicted mRNA 5' secondary structure. In the −DB constructs, two codons (6 nucleotides) were retained from the native coding region upstream of the NheI restriction site (GCTAGC sequence) in which the stop codon is out-of-frame. Twelve silent point mutations were introduced into the DB region of the PrrnLrbcL+DBm construct to either minimize the number of base pairs, or to change the nature of base pairing (for example G-C to G-U) (FIG. 2A, FIG. 3B).

Design of the 5' Leader from psbB

One primary and one processed mRNA 5-end for the psbB gene were tentatively identified in tobacco leaves (Tanaka et al., 1987). The leader sequence was designed to initiate transcription from the G (−114) of the Prrn promoter, and include the intact secondary (stem) structure assumed to be involved in stabilizing the mRNA. Forty-five and 3 nucleotides out of the psbB coding region are included in the +DB and −DB constructs, respectively. The 45 nucleotides include four potential DS sequences shown in FIG. 2A. Since the ATG is naturally included in an NcoI site that is used to fuse the neo coding region with the psbB leader, no amino acid from the psbB coding region is added in the −DB construct.

Design of the 5' Leader from psbA

One mRNA 5'-end was mapped for the psbA gene in tobacco leaves (Sugita and Sugiura, 1984). The terminal nucleotide of the primary transcript is an A. Therefore, the chimeric PrrnLpsbA promoters were designed to initiate transcription at an A, anticipating that the leader sequence of the chimeric transcript will be a perfect reproduction of the leader transcribed from the psbA promoter. Twenty-one and 3 nucleotides out of the psbA coding region are included in the +DB and −DB constructs, respectively. The 21 nucleotides include the potential DB sequence as shown in FIG. 2A. Since the neo coding region was linked to the chimeric promoter via an NcoI site which includes the translation initiation codon (ATG), no amino acid from the psbA coding region is added in the −DB constructs. This is true of a second −DB promoter, in plasmid PHK23, in which transcription is designed to initiate from the Prrn G (−114) and C (−113) (FIG. 3C).

Design of the T7 Phage Gene 10 Leader

The T7 phage gene 10 leader (63 nucleotides) was shown to promote efficient translation initiation in *E. coli* (Olins et al., 1988). This leader is used in the *E. coli* pET expression vectors (Studier et al., 1990; Novagen Inc.). The terminal nucleotide at the 5'-end is a G. Therefore, the chimeric PrrnT7g10L promoters were designed to initiate transcription at a G, anticipating that the leader sequence of the chimeric transcript will be a reproduction of the T7 phage gene 10 mRNA, with the exception of a T to A mutation which was introduced to eliminate an XbaI site. Twenty-four and 9 nucleotides from the T7 phage gene 10 coding region are included in the +DB/Ec (with *E. coli* DB sequence) and −DB constructs, respectively. To compare the efficiency of *E. coli* and plastid DB sequences in plastids, a second +DB promoter was constructed with the tobacco DB sequence (PrrnT7g10L+DB/pt). The native T7g10 leader has an NheI site directly downstream of the translation initiation codon. This NheI site was removed by a T to A point mutation in the +DB constructs (FIG. 3D).

For introduction into the plastid genome, the chimeric neo genes were cloned into plastid transformation vector pPRV111A or pPRV111B. See U.S. Pat. No. 5,877,402, the disclosure of which is incorporated herein by reference. The pPRV111 vectors target insertions into the inverted repeat region of the tobacco plastid genome, and carry a selectable spectinomcyin (aadA) resistance gene. The sequences of the vectors have been deposited in GenBank (U12812, U12813). The chimeric neo gene in vector pPRV111B is in tandem with the aadA gene, whereas in vector pPRV111A the chimeric neo is oriented divergently. The general outline of the plastid transformation vector with the chimeric neo genes is shown in FIGS. 4A and 4B.

promoter fragment while 2) adding a SacI site upstream and a seam-less overlap with the specific downstream leader sequence. The reaction contains: 1) a primer (oligonucleotide) to add a SacI site at the 5'-end of the fragment; 2) a suitable template containing the Prrn promoter sequence in plasmid pPRV100A (Zoubenko et al., 1994); and 3) a primer to add on the overlap with the leader sequence at the 3' of the amplified product. The objective of the PCR-2 step is to create the chimeric promoter with DB sequence using: 1) the product of PCR-1 step as a primer; 2) a suitable DNA template containing the specific leader sequence; and 3) primer (oligonucleotide) to include NheI restriction site at the 3'-end of the amplification product. The product of the PCR-2 is the SacI-NheI chimeric Prrn promoter fragment with DB sequence. The objective of the PCR-3 step is to remove the DB sequence while introducing a suitable NheI or NcoI restriction site. The product of PCR-3 is the SacI-NheI or SacI-NcoI chimeric Prrn promoter fragment in which the DB sequence is replaced with the NheI site. The objective of the PCR-4 step is to replace the wild-type DB with a mutant DB. The product of PCR-4 is a SacI-NheI Prrn promoter fragment.

The primers (oligonucleotides) used for the construction of chimeric promoters are listed in Table 2. The chimeric promoters were obtained by overlap extension PCR using oligonucleotides and DNA templates schematically shown in FIG. 5.

TABLE 2

Oligonucleotides used for the construction of chimeric promoters.

```
#1:  5'-CCCGAGCTCGCTCCCCCGCCGTCGTTC-3' (SEQ ID NO: 31)
#2:  5'-CGAATTTAAAATAAATGTCCGCTTGCACGTCGATCGGTTAATTCTCCCAGAAATATAGCCATCC-3'
     (SEQ ID NO: 32)
#3:  5'-CCCGCTAGCCGTGGAAACCCCAGAACC-3' (SEQ ID NO: 33)
#4:  5'-CCCGCTAGCTCTCATAATAATAAAATAAATAAATATGTC-3' (SEQ ID NO: 34)
#5:  5'-TCACTTTGAGGTGGAAACGTAACTCCCAGAAATATAGCCATCC-3' (SEQ ID NO: 35)
#6:  5'-CCCGCTAGCTTCCTCTCCAGGACTTCG-3' (SEQ ID NO: 36)
#7:  5'-CCCGCTAGCAGGCATTAAATGAAAGAAAGAAC-3' (SEQ ID NO: 37)
#8:  5'-TAAGAATTTTCACAACAACAAGGTCTACTCGACTCCCAGAAATATAGCCATCC-3'
     (SEQ ID NO: 38)
#9:  5'-CCCGCTAGCTTTGAATCCAACACTTGCTTTAG-3' (SEQ ID NO: 39)
#10: 5'-CCCGCTAGCTGACATAAATCCCTCCCTAC-3' (SEQ ID NO: 40)
#11: 5'-CAAAGATAAATAGACACTACGTAACTTTATTGCATTGCTCCCAGAAATATAGCCATCC-3'
     (SEQ ID NO: 41)
#12: 5'-CCCGCTAGCATCATTCAATACAACGGTATGAACACG-3' (SEQ ID NO: 42)
#13: 5'-TTCTAGTGGGAAACCGTTGTGGTCTCCCTCCCAGAAATATAGCCATCC-3' (SEQ ID NO: 43)
#14: 5'-CCCGCTAGCCATATGTATATCTCCTTCTTAAAG-3' (SEQ ID NO: 44)
#15: 5'-CCCGCTAGCCTGTCCACCAGTCATGCTTGCCATA-3' (SEQ ID NO: 45)
#16: 5'-CCCGCTAGCCAAGGCAGGGCTAGTGATTGCCATATGTATATCTCCTTC-3' (SEQ ID NO: 46)
#17: 5'-TTTGTTTAACTTTAAGAAGGAGATATACATATGGCAAGCATGACTGGTGG-3'
     (SEQ ID NO: 47)
#18: 5'-CTCCTTCTTAAAGTTAAACAAAATTATTTCTAGTGGGAAACCGTTGT-3' (SEQ ID NO: 48)
#19: 5'-CAAAATAGAAAATGGAAGGCTTTTTGCTCCCAGAAATATAGCCATCCC-3' (SEQ ID NO: 49)
#20: 5'-CAAAATAGAAAATGGAAGGCTTTTTTCCCAGAAATATAGCCATCCC-3' (SEQ ID NO: 50)
#21: 5'-GGGCCATGGTAAAATCTTGGTTTATTTAATC-3' (SEQ ID NO: 51)
#22: 5'-GGGGCTAGCTCTCTCTAAAATTGCAGT-3' (SEQ ID NO: 52)
#23: 5'-GAATAGCCTCTCCACCCA-3' (SEQ ID NO: 53)
#24: 5'-CCCGCTAGCCGTGGACACCCCACTTCCACTTGTTGTCGGGTTTATTCTCAT-3'
     (SEQ ID NO: 54)
#25: 5'-CCCGCTAGCTTTGAATCCTACTGAGGCTTTTGTTTCTGTTTGAGGACTCAT-3'
     (SEQ ID NO: 55)
```

Construction of Chimeric Prnn Promoters with Plastid MRNA Leaders

The chimeric Prrn promoter/leader fragments were constructed as a SacI-NheI or SacI-NcoI fragments (Table 1, below) by overlap extension PCR(SOE-PCR), essentially as described in Lefebvre et al., (1995). Construction of the Prrn-plastid leader segments is schematically shown in FIG. 5. The objective of the PCR-1 step is to 1) amplify the Prrn Construction of Chimeric Prnn Promoter/atpB Leader Segments PrrnLatpB+DBwt in plasmid pHK10 (Product of PCR-2)
PrrnLatpB−DB in plasmid pHK11 (Product of PCR-3)
PrrnLatpB+DBm in plasmid pHK50 (Product of PCR-4)
PCR-1: Oligonucleotides #1, #2 as primers; plasmid pPRV100A (Zoubenko et al., 1994) DNA as template.

PCR-2: Product of PCR-1 step, Oligonucleotide #3 as primers; plasmid pIK79 (see below) DNA as template.
PCR-3: Oligonucleotide #1, #4 as primers; Product of PCR-2 step as template.
PCR-4: Oligonucleotide #1, #24 as primers; Product of PCR-2 step as template.
Plasmid pIK79 is a Bluescript BS+ phagemid derivative which carries a PvuII/XhoI tobacco plastid DNA fragment between nucleotides 55147–60484 containing the rbcL-atpB intergenic region with divergent promoters for these genes (Shinozaki et al., 1986).

Construction of Chimeric Prnn Promoter/clpP Leader Segments
PrrnLclpP+DBwt in plasmid pHK12 (Product of PCR-2)
PrrnLclpP–DB in plasmid pHK13 (Product of PCR-3)
PCR-1: Oligonucleotides #1, #5 as primers; plasmid pPRV100A (Zoubenko et al., 1994) DNA as template.
PCR-2: Product of PCR-1 step, Oligo #6 as primers; tobacco Sal8 ptDNA fragment (Shinozaki et al., 1986) as template.
PCR-3: Oligonucleotide #1, #7 as primers; Product of PCR-2 step as template.

Construction of Chimeric Prnn Promoter/rbcL Leader Segments
PrrnLrbcL+DBwt in plasmid pHK14 (Product of PCR-2)
PrrnLrbcL–DB in plasmid pHK15 (Product of PCR-3)
PrrnLrbcL+DBm in plasmid pHK54 (Product of PCR-4)
PCR-1: Oligonucleotides #1, #8 as primers; plasmid pPRV100A (Zoubenko et al., 1994) DNA as template.
PCR-2: Product of PCR-1 step, Oligonucleotide #9 as primers; plasmid pIK79 DNA (see description of pHK10 above) as template.
PCR-3: Oligonucleotide #1, #10 as primers; Product of PCR-2 step as template.
PCR-4: Oligonucleotide #1, #25 as primers; Product of PCR-2 step as template.

Construction of Chimeric Prnn Promoter/psbB Leader Segments
PrrnLpsbB+DBwt in plasmid pHK16 (Product of PCR-2)
PrrnLpsbB–DB in plasmid pHK17 (Promoter from pHK16, digested with SacI/NcoI)
PCR-1: Oligonucleotides #1, #11 as primers; plasmid pPRV100A (Zoubenko et al., 1994) DNA as template.
PCR-2: Product of PCR-1 step, Oligo #12 as primers; tobacco Sal8 ptDNA fragment (Shinozaki et al., 1986) as template.
PCR-3 was not necessary, since the psbB translation initiation codon is naturally included in an NcoI site. Therefore, the –DB derivative could be obtained by SacI/NcoI digestion of the PCR-2 step.

Construction of Chimeric Prnn Promoter/psbA Leader Segments
PrrnLpsbA+DBwt in plasmid pHK21 (Product of PCR-2)
PrrnLpshA–DB in plasmid pHK22 (Product of PCR-3)
PCR-1: Oligonucleotides #1, #20 as primers; plasmid pPRV100A (Zoubenko et al., 1994) DNA as template.
PCR-2: Product of PCR-1 step, Oligo #22 as primers; tobacco Sal3 ptDNA fragment (Shinozaki et al., 1986) as template.
PCR-3: Oligonucleotide #1, #21 as primers; Product of PCR-2 step as template.
PrrnLpsbA(GC)–DB in plasmid pHK23 (Product of PCR-2)
PCR-1: Oligonucleotides #1, #19 as primers; plasmid pPRV100A (Zoubenko et al., 1994) DNA as template.
PCR-2: Product of PCR-1 step, Oligo #21 as primers; tobacco Sal3 ptDNA fragment (Shinozaki et al., 1986) as template.

In all of the above, PCR amplification was carried out with AmpliTaq DNA polymerase (Perkin Elmer) or Pfu DNA polymerase (Stratagene) and "stepdown" PCR that utilizes gradually decreasing annealing temperatures was performed (Hecker and Roux, 1996). The exact amplification conditions for the chimeric Prrn::LatpB promoters are given below. The amplification conditions for the remaining chimeric Prrn—plastid leader promoters were calculated according to Hecker and Roux (1996), and differ only in the annealing temperatures. Description of PCR conditions for the construction of the chimeric Prrn promoters with plastid mRNA leaders is given below; for interpretation of individual steps see scheme in FIG. 5.

| PCR-1 Program: 50 picomoles of both primers per 100 $\mu$l | | |
|---|---|---|
| 1.1 Denature | 5 min. at 94° C. | |
| 2.1 Denature | 1 min. at 94° C. | |
| 2.2 Annealing | 0.5 min. at 72° C. | 3 cycles |
| 2.3 Extension | 0.5 min. at 72° C. | |
| 3.1 Denature | 1 min. at 94° C. | |
| 3.2 Annealing | 0.5 min. at 69° C. | 3 cycles |
| 3.3 Extension | 0.5 min. at 72° C. | |
| 4.1 Denature | 1 min. at 94° C. | |
| 4.2 Annealing | 0.5 min. at 66° C. | 3 cycles |
| 4.3 Extension | 0.5 min. at 72° C. | |
| 5.1 Denature | 1 min. at 94° C. | |
| 5.2 Annealing | 0.5 min. at 63° C. | 3 cycles |
| 5.3 Extension | 0.5 min. at 72° C. | |
| 6.1 Denature | 1 min. at 94° C. | |
| 6.2 Annealing | 0.5 min. at 60° C. | 3 cycles |
| 6.3 Extension | 0.5 min. at 72° C. | |
| 7.1 Denature | 1 min. at 94° C. | |
| 7.2 Annealing | 0.5 min. at 57° C. | 20 cycles |
| 7.3 Extension | 0.5 min. at 72° C. | |
| 8.1 Extension | 10 min. at 72° C. | |
| 8.2 | 1 min. at 30° C. | |

The PCR-2 program was essentially identical to the PCR1 program set forth above with the following modifications: 1) Primers in 100 $\mu$l were the products of 1st PCR reaction, 50 picomoles of the oligonucleotide primer were used; and 2) the annealing temperature in stepdown PCR was from 67° C. to 52° C. Accordingly, the following annealing temperatures were used: Step 2.2, 67° C.; Step 3.2, 64° C.; Step 4.2, 61° C.; Step 5.2, 58° C.; Step 6.2, 55° C.; Step 7.2, 52° C.

The PCR-3 and PCR-4 programs were essentially identical to the PCR1 program with the following modification: 1) The annealing temperature in stepdown PCR was from 69° C. to 44° C. Accordingly, the following annealing temperatures were used: Step 2.2, 69° C.; Step 3.2, 64° C.; Step 4.2, 59° C.; Step 5.2, 54° C.; Step 6.2, 49° C.; Step 7.2, 44° C. In cases where the yield of the final PCR reaction was too low for efficient cloning, final product was amplified using primers which were used to generate the ends. The final PCR products were digested with the appropriate restriction enzymes (SacI and NheI or SacI and NcoI) and cloned in plasmids pHK2 or pHK3 (see below).

Construction of Chimeric Promoters with T7 Phage Gene 10 mRNA Leader Segment

The chimeric Prrn promoter/T7gene10 leader (PrrnLT7g10) fragments were constructed as SacI-NheI fragments (Table 1, below).

PrrnLT7g10+DB/Ec promoter in plasmid pHK18

In the absence of a proper DNA template, the PrrnLT7g10+DB/Ec was constructed by employing a modified polymerase chain reaction (Uchida, 1992) in two PCR steps, as schematically shown in FIG. 6. The PCR-1A and PCR1B steps generate two fragments in two separate reactions (A and B). The objective of the PCR-1A step is to amplify Prrn promoter fragment while: 1) adding a SacI site upstream (Oligonucleotide #1 in Table 2); and 2) a seam-less overlap with the specific downstream leader sequence (Oligonucleotide #13 in Table 2) using plasmid pPRV100A (Zoubenko et al., 1994) as DNA template. The objective of the PCR-1B step is to amplify part of the T7g10 leader sequence using overlapping oligonucleotides #15 and #17 in Table 2. The NheI site is introduced in oligonucleotide #15. Both PCR-1A and PCR-1B reactions were carried out by stepdown PCR as described above for the construction of the chimeric Prrn promoters.

PCR-2 reaction generating this chimeric promoter contained:
a) The products of the PCR-1A and PCR-1B reactions as DNA templates;
b) Oligonucleotide #18 (0.5 picomole; Table 2) to generate overlapping fragments with products of the PCR-1A and PCR-1B reactions;
c) Oligonucleotides #1 and #15 (Table 2) for amplification of the final product, 50 picomoles each in 100 µl final volume.

Promoter was amplified by stepdown PCR, as described for the chimeric Prrn promoters above; the annealing temperatures were between 72° C. to 57° C.

PrrnLT7g10+DB/pt Promoter in Plasmid pHK19

The promoter fragment was obtained in one PCR step as shown in FIG. 7. The reaction contained:
a) The product of the PCR-2 reaction generating promoter PrrnLT7g10+DB/Ec in plasmid pHK18 as DNA template; and
b) Oligonucleotides #1 and #16 (Table 2), 50 picomoles each in 100 µl final volume.

Promoter was amplified by stepdown PCR, as described for the construction of chimeric Prrn promoters above; the annealing temperatures were between 72° C. to 52° C.

PrrnLT7g10–DB Promoter in Plasmid pHK20

The promoter fragment was obtained in one PCR step, which is similar to the PCR-3 step in FIG. 5. The reaction contained:
a) The product of the PCR-2 reaction generating promoter PrrnLT7g10+DB/Ec in plasmid pHK18 as DNA template; and
b) Oligonucleotides #1 and #14 (Table 2), 50 picomoles each in 100 µl final volume.

Promoter was amplified by stepdown PCR, as described for the chimeric Prrn promoters above; the annealing temperatures were between 72° C. to 52° C.

The final PCR products were digested with the SacI and NheI restriction enzymes and cloned in plasmid pHK3 to obtain plasmids PHK18, pHK19, pHK20.

Construction of Chimeric Neo Genes

Construction of the chimeric promoters was described in the preceding sections. For determining effects on levels of protein accumulation, the promoters were cloned upstream of a kanamycin-resistance encoding construct, consisting of the neo coding region and the 3'-UTR of the plastid rbcL gene. Such constructs are available in plasmids pHK2 and pHK3, which carry the same Prrn(L)rbcL(S)::neo::TrbcL gene as a SacI-HindIII fragment. Plasmid pHK2 is a pUC118 vector derivative; pHK3 is a pBSIIKS+ derivative. Plasmid maps with relevant restriction sites are shown in FIG. 8. DNA sequence of the neo gene in plasmids pHK2 and pHK3 is shown in FIG. 9. Note, that in plasmid pHK2 the neo gene has an EcoRI site upstream of the SacI site (FIG. 8). Prrn and TrbcL have been described by Staub and Maliga, 1994; the neo gene derives from plasmid pSCl (Chaudhuri and Maliga, 1996). The pUC118 and pBSIIKS+ plasmid derivatives which carry the various promoter constructs are listed in Table 1.

To determine the DNA sequence of the promoter fragments, the plasmids were purified with the QIAGEN Plasmid Purification Kit following the manufacturer's recommendations. DNA sequencing was carried out using a T7 DNA sequencing kit (version 2.0 DNA, Amersham Cat. No. US70770) and primer No. #23 in Table 2, which is complementary to the neo coding sequence. These promoter sequences are shown in FIGS. 3A–D.

Introduction of Chimeric Neo Genes into the Tobacco Plastid Genome

Suitable vectors are available for the introduction of foreign genes into the tobacco plastid genome. Such vectors are pPRV111A and pPRV111B, which carry a selectable spectinomycin-resistance (aadA) gene and target insertions into the repeated region of the plastid genome (Zoubenko et al., 1994). The chimeric neo genes were cloned into one of these plastid transformation vectors (Table 1) and introduced into the tobacco plastid genome by the biolistic process. From the transformed cells plants were regenerated by standard protocols (Svab and Maliga, 1993). A uniform population of transformed plastid genome copies was confirmed by Southern analysis.

For Southern analysis, total cellular DNA was prepared by the CTAB method (Saghai-Maroof et al., 1984). Two leaves of each transformed plant were homogenized and incubated at 60° C. for 30 minutes in a buffer containing 2% CTAB (tetradecyl-trimethyl-ammonium bromide), 1.4 M NaCl, 20 mM EDTA (pH 8.0), 1 mM Tris/HCl (pH 8.0) and 100 mM β-mercaptoethanol. After chloroform extraction, the DNA was precipitated with isopropyl alcohol and dissolved in water or in TE buffer (10 mM Tris, 1 mM EDTA, pH 8.0). DNA digested with an appropriate restriction enzyme was electrophoresed on 0.8% agarose gel and transferred to nylon membrane using PosiBlot Transfer apparatus (Stratagene). The blots were probed using Rapid Hybridization Buffer and plastid targeting sequences as a probe labeled with random is priming ($^{32}P$, Boehringer Mannheim Cat No. 1004760).

Plastid transformation was achieved with each of the plasmids listed in Table 1. Exceptions were plasmids pHK41 and pHK42. It appears that NPTII expression with the psbA leader derivatives was so high that the plants were not viable. It follows that these same leaders may be used to advantage when fused with weaker promoters.

Transplastomic lines are designated by Nt (N. tabacum, the species), the plasmid name (for example pHK30) and an individual line number and a letter identifying regenerated plants. For example, the Nt-pHK30-1D and Nt-pHK30-1C plants were both obtained by transformation with plasmid pHK30, are derived from the same transformation event and were regenerated from the same culture. Nt-pHK30-2 plants are derived from an independent transformation event. Normally, several transformed lines per construct were obtained. However, data are shown here only for one: Nt-pHK30-1D, Nt-pHK31-1C, Nt-pHK60-5A, Nt-pHK32-2F, Nt-pHK33-2A, Nt-pHK34-9C, Nt-pHK35-4A, Nt-pHK64-3A, Nt-pHK36-1C, Nt-pHK37-2D, Nt-pHK38-2E, Nt-pHK39-3B, Nt-pHK40-12B and Nt-pHK43-1C.

Testing mRNA Accumulation by RNA Gel Blot (Northern) Analysis

RNA gel blot analysis was performed to determine steady-state levels of chimeric mRNA in the transplastomic lines. Total leaf RNA was prepared from the leaves and roots of plants grown in sterile culture according to Stiekema et al (1988). RNA (4 µg per lane) was electrophoresed on 1% agarose gel and transferred to nylon membranes using the PosiBlot Transfer apparatus (Stratagene). The blots were probed using Rapid Hybridization Buffer Amersham) with a $^{32}$P-labeled neo probe (Pharmacia, Ready-To-Go Random Priming Kit). The neo probe was obtained by isolating the NheI/XbaI fragment from plasmid pHK2. The template for probing the tobacco cytoplasmic 25S rRNA was a fragment which was PCR amplified from total tobacco cellular DNA with primers 5'-TCACCTGCCGAATCAACTAGC-3' (SEQ ID NO: 56) and 5'-GACTTCCCTTGCCTACATTG-3' (SEQ ID NO: 57). RNA hybridization signals were quantified using a Molecular Dynamics PhosphorImager, and normalized to the 25S rRNA signal.

Testing NPTII Accumulation by Protein Gel Blot (Western) Analysis

Total soluble protein was extracted from the leaves, roots or seeds of transgenic tobacco plants grown in sterile culture. In case of leaves grown in sterile culture, about 200 mg leaf tissue was homogenized in 1 ml of buffer containing 50 mM Hepes/KOH (pH 7.5), 1 mM EDTA, 10 mM potassium acetate, 5 mM magnesium acetate, 1 mM dithiothreitol and 2 mM PMSF. The homogenate was centrifuged twice at 4+ C. to remove insoluble material. Protein concentration was determined using the Biorad Protein Assay reagent kit. Transgenic tobacco plants expressing neo in the plastid genome (Nt-pTNH32-70, Carrer et al., 1993) and wild type plants were used as positive and negative controls, respectively. Proteins were separated in SDS polyacrylamide gels (SDS-PAGE; 15% acrylamide, 6 M urea) and transferred to nitrocellulose membranes using a semi-dry transfer apparatus (Bio-Rad). After blocking non-specific binding sites, the membrane was incubated with 4,000-fold diluted polyclonal rabbit antiserum raised against NPTII (5Prime-3Prime Inc.). HRP-conjugated secondary antibody, diluted 20,000 fold, and ECL chemiluminescence were used for immunoblot detection on X-ray film. NPTII was quantified on the immunoblots by comparison of the experimental samples with a dilution series of commercial NPTII (5Prime-3Prime).

EXAMPLE 1

DB Sequences Enhance Protein Accumulation from rbcL Leader; Protein Accumulation from the atpB Translation Control Signals is High but DB-Independent The role of DB sequences in mRNA translation was tested using neo as the reporter gene. The neo gene encodes the bacterial enzyme neomycin phosphotransferase (NPTII) (Beck et al., 1982). The tested neo genes have the same promoter (Prrn) and transcription terminator (TrbcL), and differ only with respect to the translation control region (TCR) comprising the 5' untranslated region of the mRNA and the coding region N-terminus. Two constructs were prepared with the atpB and rbcL TCRs. One construct contained the wild-type TCR, including the processed 5' untranslated region and 42 nucleotides of the coding region N-terminus (PrrnLatpB+DBwt, plasmid pHK30, FIG. 4B; PrrnLrbcL+DBwt, plasmid pHK34, FIG. 4A). The second construct contained silent mutations in the 42-nucleotide segment of the atpB and rbcL N-terminal coding regions to either eliminate or alter mRNA and rRNA base pairing (PrrnLatpB+DBm plasmids pHK60; FIG. 2A and FIG. 4B; PrrnLrbcL+DBm, pHK64, FIG. 2A and FIG. 4A). The silent mutations altered the mRNA sequence without effecting the amino acid sequence. For example, 13 potential base pairs may form between the wild-type atpB mRNA and the ADB sequence shown at the bottom in FIG. 2A. The 11 silent mutations affect eight base-paring events for this particular ADB-DB interaction. After mutagenesis, there is a possibility for ten base pairing events, most of which are new. The chimeric neo genes were introduced into the tobacco plastid genome by homologous targeting using the biolistic approach (Svab and Maliga, 1993; Zoubenko et al., 1994). NPTII and neo mRNA levels were then assessed in the leaves of transplastomic plants. Since NPTII in wild-type DB-containing and mutant DB-containing plants has the exact same protein sequence, protein levels in the plants directly reflect the efficiency of mRNA translation. In case of the atpB TCR, mutagenesis of DB reduced protein accumulation to ~4% instead of ~7% (FIG. 10 and Table 3). In contrast, mutagenesis of rbcL DB had a dramatic effect, reducing NPTII accumulation 35-fold. Thus, DB-ADB interaction is very important for translation of the plastid rbcL mRNA, but is less important for translation of the atpB mRNA.

We also prepared a third construct set with the atpB and rbcL leaders, but without the native DB (PrrnLatpB–DB, plasmid pHK31, FIG. 4B; PrrnLrbcL–DB, plasmid pHK35, FIG. 4A). The neo coding region in these constructs is directly linked to the Prrn promoter via a synthetic NheI restriction site. The NheI restriction site (GCTAGC) is fully complementary to the ADB region (FIG. 2B), therefore it was hoped that it would function as a DB sequence. Utility of NheI site as an alternative DB could be best judged by NPTII accumulation from the rbcL leader, which is highly dependent on DB. High levels of NPTII from the NheI construct (4.7%) relative to the mutant DB (0.3%) indicate, that linking the coding region via an NheI site provides a suitable DB for expressing foreign polypeptides (FIG. 10, Table 3).

TABLE 3

Levels of NPTII and neo mRNA in tobacco leaves

|  | SD | DB | NPTII (%) | nea mRNA | NPTII/ neo mRNA |
|---|---|---|---|---|---|
| Nt-pTNH32-70 | + | – | 2.10 ± 0.33 | 41.5 | 5.06 |
| Nt-pHK30-1D | (+) | wt | 7.02 ± 0.82 | 70.05 ± 12.33 | 8.85 |
| Nt-pHK31-1C | (+) | s | 2.52 ± 0.79 | 100 | 2.52 |
| Nt-pHK60-5A | (+) | m | 4.03 ± 1.45 | 91.57 ± 12.76 | 4.40 |
| Nt-pHK32-2P | – | wt | 1.17 ± 0.05 | 49.33 ± 7.76 | 2.37 |
| Nt-pHK33-2A | – | s | 0.21 ± 0.05 | 49.55 ± 6.67 | 0.42 |
| Nt-pHK34-9C | + | wt | 10.83 ± 3.84 | 48.91 ± 22.65 | 22.14 |
| Nt-pHK35-4A | + | s | 4.68 ± 1.84 | 21.41 ± 7.88 | 21.86 |
| Nt-pHK64-3A | + | m | 0.31 ± 0.15 | 52.47 ± 4.29 | 0.59 |
| Nt-pHK36-1C | + | wt | 2.17 ± 70.97 | 68.8 | 3.15 |
| Nt-pHK37-2D | + | s | 2.35 ± 0.05 | 42.3 | 5.56 |
| Nt-pHK38-2E | + | Ec | 16.39 ± 3.42 | 47.59 ± 19.06 | 34.44 |
| Nt-pHK39-3B | + | pt | 0.16 ± 0.13 | 13.12 ± 1.27 | 1.22 |
| Nt-pHK40-12B | + | s | 23.00 ± 5.40 | 90.27 ± 31.83 | 25.48 |
| Nt-pHK43-1C | (+) | s | 0.65 ± 0.28 | 13.2 | 4.92 |

Discussion

In bacteria, mutagenesis or deletion of the DB reduces translation 2- to 34-fold, depending on the individual mRNA (Etchegaray and Inouye, 1999; Faxén et al., 1991; Ito et al., 1993; Mitta et al., 1997; Sprengart et al., 1996). Furthermore, reliance on the DB increases when the SD sequence is removed (Sprengart et al., 1996; Wu and Janssen, 1996). In our experiments, no variation was made in the atpB or rbcL 5'UTR, only sequences downstream of the AUG were altered. Mutagenesis of the atpB DB region reduced protein levels ~2-fold. Although the atpB mRNA does not have a SD directly upstream of AUG, we speculate that it probably has an alternate mechanism for translation initiation that reduces its dependence on the DB. Alternatively translation initiation may be facilitated by activator proteins as described for *Chlamydomonas* chloroplasts (Rochaix, 1996; Stern et al., 1997). The consequence of DB mutagenesis on rbcL translation was a dramatic 35-fold drop in NPTII levels. Accordingly, efficient rbcL translation is highly dependent on DB-ADB interactions. Genes in both prokaryotes and eukaryotes show biases in the usage of the 61 amino acid codons and have a tRNA population closely matched to the overall codon bias of the resident mRNA population. Incorporation of synonymous minor codons in the coding region may dramatically reduce translation (Makrides, 1996) and destabilize the mRNA (Deana et al., 1998). A well-characterized example for minor codons causing reduced expression in *E. coli* are the AGA/AGG arginine codons recognized by the same tRNA which are present at the frequency of 2.6 and 1.6 per thousand codons. Therefore, we have compared codon usage bias and frequency of triplets per 1000 nucleotides in the wild-type and mutagenized atpB and rbcL DB regions. Since we studied NPTII accumulation in leaves, the values shown in FIG. 12 were calculated for the highly expressed rbcL, psaA, psaB, psaC, psbA, psbB, psbC, psbD, psbE and psbF photosynthetic genes using the Genetics Computer Group (GCG; Madison Wis.) codon frequency program. Codon usage bias and triplet frequency is comparable in the wild-type and mutant DB regions of both atpB and rbcL. In addition, the mRNAs for the wild-type and mutant DB constructs accumulate at similar levels. Therefore, the dramatic change in NPTII acccumulation from the PrrnLrbcL+DBm promoter in the Nt-pHK64 line can not be attributed to incorporation of a rare codon in the mutant DB region.

We have shown here that sequences downstream of the translation initiation codon may dramatically affect mRNA translation. Therefore, silent mutations in the DB region of heterologous proteins may significantly improve expression in chloroplasts by increasing complementarity of the mRNA with the plastid rRNA penultimate stem structure.

There are significant differences in NPTII accumulation from neo transgenes with different leaders and the same synthetic DB (Table 3). This indicates that the 5'UTR is an important determinant of translation efficiency. Many data are available supporting the importance of 5'UTR as a target for translational control in higher plants (Hirose and Sugiura, 1996; Staub and Maliga, 1993; Staub and Maliga, 1994b) and the unicellular alga *Chlamydomonas* (Mayfield et al., 1994; Nickelsen et al., 1999; Sakamoto et al., 1993; Zerges et al., 1997). The data presented herein demonstrate that translation efficiency in plastids is determined by sequences both upstream and downstream of the AUG.

EXAMPLE 2

Study of Phage T7g10 Translation Control Sequences Indicates that the Efficient DB in Plastids has Loose Complementarity to ADB Since the actual ADB sequence is different in plastids and *E. coli*, we anticipated (Sprengart et al., 1996; Etchegaray & Inoyue, 1999) that replacement of the *E. coli* DB with a perfect plastid DB (100% DB-ADB complementarity) would enhance translation in plastids. We choose the phage T7g10 translational control region for the study since it has a well-characterized *E. coli* DB. Three Prrn promoter derivatives were constructed. Cassette PrrnLT7g10+DB/Ec consists of Prrn fused with the native T7g10 TCR containing the *E. coli* DB (plasmid pHK38; FIG. 2B, FIG. 4A). Cassette PrrnLT7g10+DB/pt consists of the Prrn promoter, T7g10 leader and the perfect tobacco DB (pHK39; FIG. 2B, FIG. 4A). Cassette PrrnLT7g10–DB has the Prrn promoter and T7g10 leader, but lacks the T7g10 DB sequence (pHK40; FIG. 2B, FIG. 4A). The neo coding region in these constructs is directly linked to the Prrn promoter via a synthetic NheI restriction site. The neo genes in the three expression cassettes were introduced into tobacco plastids by transformation (Svab and Maliga, 1993; Zoubenko et al., 1994) and the leaves of transplastomic tobacco were tested for NPTII accumulation and mRNA levels (FIGS. 10, 11; Table 3).

Surprisingly, NPTII levels from the heterologous T7g10 TCR were higher (Nt-pHK38; ~16%) than the levels obtained from the rbcL TCR (Nt-pHK34; ~11%). We expected that incorporation of the plastid DB with 100% complementarity would further enhance NPTII levels. Instead, we found that plants transformed with the construct having the perfect plastid DB (Nt-pHK39) contained NPTII levels 100-fold lower than the plants expressing NPTII from the *E. coli* TCR (Nt-pHK38; FIG. 10; Table 3). This result suggests that, unlike in *E. coli*, 100% complementarity reduces, rather than enhances translation efficiency. Indeed, none of the highly expressed plastid genes have a perfect DB sequence (FIG. 2A). RNA gel blots shown in FIG. 11 indicate that Nt-pHK39 plants with the perfect DB contain ~3-fold less neo mRNA. Therefore, a contributing factor to lower NPTII levels in these plants appears to be a faster mRNA turnover rate. Furthermore, NPTII expressed from the PrrnLT7g10 derivatives differ by the DB-encoded amino acids at the N-terminus. Therefore, differential protein turnover rates may be part of the reason for differences in NPTII accumulation. The highest yield of NPTII (23%) was obtained with the synthetic, NheI-containing DB cassette.

Discussion

This example utilizing the rbcL translation control regions reveals that sequences downstream of the translation initiation codon may dramatically affect mRNA translation. Therefore, silent mutations in the DB region of heterologous proteins may significantly improve expression in chloroplasts by increasing complementarity of the mRNA with the plastid rRNA penultimate stem structure. However, it appears that perfect complementarity is undesirable, as it may accelerate mRNA turnover and reduce the rate of translation. This finding highlights differences in the translation machinery of plastids and *E. coli*, in which perfect complementarity enhances translation (Etchegaray and Inouye, 1999; Sprengart et al., 1996). It is possible, however, that shifting the region of complementarity relative to AUG or targeting a slightly different region of the penultimate stem may facilitate highly efficient translation of mRNAs with a perfectly matched DB.

The T7g10 constructs have one or two relatively rare AGC serine codons (4.7 per 1000, FIG. 12), one of which is encoded in the NheI site. This codon is present in the Nt-pHK38 and Nt-pHK40 plants, which contain the highest levels of NPTII. Further improvement may be expected by replacing the AGC with an AGT serine codon.

EXAMPLE 3

The clpP, pabB and psbA TCRs have Distinct Expression Characteristics

NPTII accumulation was studied in transplastomic tobacco carrying the PrrnLclpP promoter derivatives. The PrrnLclpP+DBwt (Nt-pHK32-2F) and PrrnLclpP−DB (Nt-pHK33-2A) plants accumulate 1.2% and 0.2% NPTII in their leaves (FIG. 10; Table 3). We have found that overexpression of clpP 5'-UTR causes a mutant phenotype manifested as pale green leaf color and slower growth. This phenotype is normalized in older plants. We assume that the primary cause of this mutant phenotype is the lack of ClpP protein, the clpP gene product. This mutant phenotype is absent in plants transformed with other 5'UTRs. Therefore we believe, that the mutant phenotype is attributable to competition for a clpP-specific nuclear factor. The clpP gene has two introns. Preliminary RNA gel blot analysis reveals reduced levels of mature, monocistronic clpP mRNA (~30% of wild-type) and accumulation of intron I-containing clpP pre-mRNA in the pale-green leaves. Normalization of phenotype coincides with increase of translatable monocistronic clpP mRNA to wild type levels. Over-expression of clpP 5'UTR therefore may interfere with splicing of clpP pre-mRNA.

NPTII accumulation was also studied in transplastomic tobacco carrying the PrrnLpsbB promoter derivatives. The PrrnL psbB+DBwt (Nt-pHK36-1C) and PrrnL psbB−DB (Nt-pHK37-2D) plants accumulate 2.2% and 2.4% NPTII in their leaves (FIG. 10; Table 3). Thus, the synthetic DB sequence in case of the psbB TCR efficiently replaces the native DB sequence. Conversely, it may rely on an alternative mechanism for translation initiation.

The Prrn promoter constructs with the psbA leader were obtained as described. However, we have been able to introduce only one of them, PrrnLpsbA−DB(+GC) into tobacco plastids in line Nt-pHK43-1C. The Nt-pHK43-1C plants accumulate NPTII at a relatively low level (0.6%; FIG. 10, Table 3). It is conceivable that the lack of success in introducing the +DB construct is due to the dramatically elevated expression level of NPTII which is toxic to the plants.

Discussion

NPTII levels obtained from PrrnLclpP+DBwt (Nt-pHK32-2F) promoter are relatively low, only 1.2% of the total soluble protein. However, this promoter is desirable for driving expression of selectable marker genes, as the recovery of transplastomic clones is relatively efficient when the neo gene is expressed from this promoter, as shown in Example 4. Expression of neo from the PrrnLclpP+DBwt promoter does not cause a mutant phenotype in tissue culture. Thus, it is suitable to drive the expression of marker genes, so long as the marker gene is subsequently removed. It appears that competition for a nuclear-encoded factor required for processing the clpP introns gives rise to the reduced expression observed. This intron is absent in the clpP genes in the monocots rice (Hiratsuka et al., 1989) and maize (Maier et al., 1995). The PrrnLclpP+DBwt promoter therefore may be used to advantage in the transformation of monocots. Furthermore, the level of the trans-factor required for clpP intron processing is likely to be expressed at different levels in dicots. We anticipate therefore, that expression of the clpP TCR will have no undesirable consequences in other dicot species. It is also possible that the phenotypic consequences of expressing the clpP TCR in plastids is a property of the tobacco line, *N. tabacum* cv. Petit Havana utilized herein and is absent in other tobacco lines. This would make the clpP gene TCR a desirable expression tool in both monocots and dicots.

Both psbB leader derivatives accumulate NPTII at comparable levels (2.2% and 2.4%, respectively; Table 3). This 5 regulatory region is a good alternative to the most commonly used rbcL leader when protein accumulation is required in the ~2% range.

In the past, the psbA promoter and leader construct yielded relatively high levels of expression in leaves (2.5% GUS; Staub and Maliga, 1993). Yet these constructs did not contain psbA DB elements. The present invention describes the generation of chimeric promoters that are suitable to obtain high-level protein expression while elucidating the regulatory role played by DB sequences. Prrn is the strongest known promoter in plastids and consequently provides for high levels of NPTII translation. These elevated levels of NPTII can be toxic to the plant and therefore it is difficult to obtain transplastomic lines with the highest prospective levels of NPTII. An alternative approach involves operably linking the psbA leader to a relatively weak promoter. This approach may generate cassettes which are suitable for obtaining relatively high levels of protein accumulation from relatively low levels of mRNA.

EXAMPLE 4

NPTII Accumulation in Roots and Seeds

Posttranscriptional regulation is an important mechanism of plastid gene expression (Rochaix, 1996; Stem et al., 1997). Therefore, we expected that NPTII accumulation may be tissue-specific due to regulation of gene expression at the level of mRNA translation. Thus, NPTII accumulation was tested in roots and seeds.

Testing of NPTII accumulation in roots was carried out with a subset of transplastomic lines (Table 4). Roots for protein extraction were collected from plants grown in liquid MS salt medium (3% sucrose) in sterile cultures incubated on a shaker to facilitate aeration. Protein was extracted from the roots with the leaf protocol and tested for NPTII accumulation (FIG. 13 A). The highest level of NPTII, 0.75%, is found in the roots of plants expressing NPTII from the clpP TCR (PrrnLclpP+DBwt construct; pHK32). The second highest value, 0.3%, was found in the roots of plants transformed with plasmid pHK38 expressing NPTII from the T7g10 TCR (PrnnLT7g10+DB/Ec promoter). The level of NPTII was about the same, approximately 0.1%, in roots expressing the recombinant protein from the atpB and rbcL TCR in pHK30- and pHK34-transformed plants.

Since plastids in the roots are smaller than in leaves, we expected lower levels of NPTII accumulation in the roots than in the leaves. This was true for all the tested roots, except those of the Nt-pHK32 plants. Interestingly, NPTII from the clpP TCR accumulated at almost the same level in the roots (0.75%, Table 4) as in the leaves (approximately 1%, Table 3). This is likely attributable to high levels of the neo mRNA in the roots (FIG. 13B). Since the clpP leader includes the minimal PclpP-53 promoter (Sriraman et al., 1998a; NAR 26: 4874) we speculate, that the relatively high mRNA levels are due to activation of PclpP-53 in roots. High levels of expression make the clpP leader a desirable TCR for protein expression in roots.

The T7g10 leader (pHK38) was the most efficient in roots from which the most NPTII accumulated relative to the mRNA (Table 4). Although in the Nt-pHK38 plants, the neo mRNA was 7-times less than in the Nt-pHK32 plants, NPTII levels were almost as high (approximately 0.30% compared to 0.75%) as in the plastids with the clpP TCR (pHK32). High level NPTII accumulation from the T7g10 TCR in leaves (pHK38, pHK40; Table 3) and in roots (pHK38; Table 4) indicates the general utility of the phage T7g10 translation control region for protein expression in plastids.

Protein accumulation was also studied in seeds harvested from the transgenic plants (FIG. 14). Protein levels were 0.05% in plants transformed with pHK32 (clpP TCR), and approximately 0.01% in plants transformed with plasmid pHK30 (atpB TCR). No NPTII was detectable in plants in which neo was introduced in the rbcL TCR-construct (plasmid pHK34), indicating differential protein accumulation which is dependent on the choice of the TCR.

TABLE 4

Levels of NPTII and neo mRNA in tobacco roots

| Strain | NPTII (%) | neo mRNA (%) | NPTII/neo mRNA × $10^3$ |
|---|---|---|---|
| Nt-pHK30-1D | 0.14 ± 0.05 | 33.7 | 4.2 |
| Nt-pHK32-2F | 0.75 ± 0.35 | 100 | 7.5 |
| Nt-pHK34-9C | 0.12 ± 0.03 | 23.5 | 5.1 |
| Nt-pHK38-2E | 0.31 ± 0.04 | 13.4 | 23.1 |

EXAMPLE 5

High-level NPTII Expression Facilitates Efficient Recovery of Transplastomic Lines by Selection for Kanamycin Resistance The plastid genome of higher plants is a 120-kb to 160-kb double-stranded DNA which is present in 1,900 to 50,000 copies per leaf cell (Bendich, 1987). To obtain genetically stable transplastomic lines every one of the plastid genome copies (ptDNA) should be uniformly altered in a plant. Since integration of foreign DNA always occurs by homologous recombination, plastid transformation vectors contain segments of the plastid genome to target insertions at specific locations. Useful, non-selectable genes are cloned next to the selectable marker genes, which are then introduced into the plastid genome by linkage to the selectable marker gene (Maliga, 1993). Transforming DNA is introduced into plastids by the biolistic process (Svab et al., 1990; Svab and Maliga, 1993) or PEG treatment (Golds et al., 1993; O'Neil et al., 1993). Elimination of wild-type genome copies occurs during repeated cell divisions on a selective medium. The success of transformation depends on the success of selective amplification of the few initially transformed genome copies. Therefore the choice of the antibiotic used for the selective amplification of transformed genome copies and the mechanism by which the plant cells are protected from antibiotic action is a critical parameter to be considered for successful generation of homoplasmic plants.

The most commonly used antibiotic for the selection of transplastomic lines is spectinomycin, an inhibitor of protein synthesis on plastid ribosomes. Initially, plastid transformation in tobacco was carried out by selection for resistance based on mutations in the plastid 16S rRNA (Svab et al., 1990). Selection was inefficient, yielding about one transplastomic clone per 50 bombarded samples, probably because the 16S rRNA based mutation in recessive. Recovery of transplastomic lines was enhanced ~100-fold by selection for a dominant marker, spectinomycin resistance based on inactivation by aminoglycoside 3" adenyltransferase encoded in a chimeric aadA gene (Svab and Maliga, 1993): In addition to tobacco, selection for spectinomycin resistance (aadA) could be applied to recover transplastomic lines in Arabidopsis and potato. The aadA gene in plants confers resistance to both spectinomycin and streptomycin. Selection for streptomycin resistance was used for plastid transformation in rice, a species resistant to spectinomycin, after bombardment with a chimeric aadA gene. See Example 8.

The need for an alternative marker gene for plastid manipulation has led to testing kanamycin resistance as a selective marker. A chimeric neo (kan) gene, encoding neomycin phosphotransferase, was suitable to recover transplastomic tobacco lines. However, recovery of transplastomic lines was relatively inefficient, yielding only one transplastomic line in ~25 bombarded leaf samples. Furthermore, for every plastid transformation event ~25 to 50 kanamycin resistant lines were obtained in which integration of the plastid neo construct into the nuclear genome resulted in kanamycin resistance (Carrer et al., 1993). We report here that the efficiency of recovering transplastomic clones is significantly improved when transforming tobacco chloroplasts with a new neo gene expressed from a promoter with the atpB and clpP translation control region. The number of nuclear transformation events is reduced using the cassettes of the present invention. These improvements make the new neo gene a practical tool for plastid genome manipulations.

Discussion

The chimeric neo genes described in Examples 1–4 is were introduced into plastids by selection for the linked spectinomycin resistance (aadA) gene as their suitability for directly selecting transplastomic lines was unknown. The transplastomic lines listed in Table 3 were then tested for resistance to kanamycin by their ability to proliferate on a medium containing 50 mg/L kanamycin. The RMOP meduim used for testing induces formation of green callus and shoot regeneration in the absence of kanamycin. The tissue culture procedures utilized for this example are described in references Carrer et al., 1993 and Carrer and Maliga, 1995.

On the selctive kanamycin medium only scanty, white callus forms from wild-type leaf section. Formation of green callus and shoots from leaf section of plants transformed with pHK plasmids in Table 3 indicates that accumulation of NPTII confers kanamycin resistance. We set out to test if transplastomic clones can be directly selected by kanamycin resistance after bombardment with plasmids pHK30 and pHK32. The results are summarized in Table 5.

Bombardment of 25 tobacco leaves with plasmid pHK30 yielded 45 kanamycin resistant lines on a medium containing 50 mg/L kanamycin. Transplastomic neo lines are expected to be resistant to much higher levels, 500 mg/L of kanamycin (Carrer et al., 1993). In addition, in plasmid pHK30 the neo gene is physically linked to a spectinomycin resistance (aadA) gene. Spectinomycin resistance is manifested as kanamycin resistance: sensitive leaf sections form white callus and no shoots whereas resistant leaf sections form green callus and shoots on a selective medium (500 mg/L) RMOP medium. We assumed therefore, that all transplastomic lines should be resistant to both 500 mg/L of kanamycin and 500 mg/L spectinomycin (Carrer and Maliga, 1995). When applying this test we found that 22 of the 45 lines meet these criteria. Digestion of the plastid DNA with the EcoRI restriction enzyme and probing with the plastid targeting region should detect 3.1-kb fragment in the wild-type and a 4.2-kb and 1.2-kb fragment in transplastomic lines (FIG. 15A). DNA gel blot analysis of seven of the kanamycin-spectinomycin resistant lines confirmed integration of both transgenes into the plastid genome (FIG. 15B). Therefore, we assume that all 22 kanamycin-spectinomycin lines are transplastomic (Table 5).

Bombardment of 30 tobacco leaves with plasmid pHK32 yielded 28 kanamycin resistant lines on a medium containing 50 mg/L kanamycin. We have identified 11 double-resistant lines by testing these on a medium containing 500 mg/L of kanamycin and 500 mg/L spectinomycin. All six tested were transplastomic by DNA gel blot analysis (FIG. 15B), therefore we believe that all eleven are transplastomic (Table 5).

TABLE 5

SELECTION OF TRANSPLASTOMIC TOBACCO CLONES BY KANAMYCIN RESISTANCE

| Vector | No. leaves | Kan. Res. 50 mg/L | Kan. Res. 500 mg/L | Kan. Res. 500 mg/L Spec. Res. 500 mg/L | Transplastomic |
|---|---|---|---|---|---|
| pTNH32 | 29 | 59 | 7 | | 0 |
| | 50[a] | 52 | | | 2 |
| | 25[a] | 47 | 4 | | 1 |
| pHK30 | 25 | 45 | | 22 | 22 |
| pHK32 | 30 | 28 | | 11 | 11 |

([a]Carrer et al., 1993)

Discussion

Plastid transformation efficiency should be comparable, if we target the same region of the plastid genome for insertion, use similar size targeting sequences and the same method of DNA delivery. Therefore, lower transformation efficiencies obtained by selection for kanamycin resistance with the old chimeric neo genes was likely due to the lack of recovery of tranplastomic clones by selection. We have found that transformation with neo genes expressed from the PrrnLatpB+DBwt and PrrnLclpP+DBwt promoters is as efficient as with the aadA gene. This is a significant technical advance, and will facilitate plastid transformation in crops, in which the regenerable tissues contain non-green plastids. Most important targets are the non-green plastids of cereal crops. Kanamycin selection is widely used to obtain transgenic lines after transformation with chimeric neo genes in dicots. However, kanamycin is an undesirable selective agent in monocots such as cereal tissue cultures. However, NPTII also inactivates paromomycin, which may be used to recover nuclear gene transformants at an extremely high efficiency in cereals. See for example, PCT application WO99/05296.

EXAMPLE 6

Bacterial Bar Gene Expression in Tobacco Plastids Confers Resistance to the Herbicide Phosphinothricin Bialaphos, a non-selective herbicide, is a tripeptide composed of two L-alanine residues and an analog of glutamic acid known as phosphinothricin (PPT). While PPT is an inhibitor of glutamine synthetase in both plants and bacteria, the intact tripeptide has little or no inhibitory effect in vitro. Bialaphos is toxic for bacteria and plants, as intracellular peptidases remove the alanine residues and release active PPT. Bialaphos is produced by *Streptomyces hygroscopicus*. The bacterium is protected from phosphinothricin toxicity by phosphinothricin acetyltransferase (PAT), the bar gene product. This enzyme acetylates phosphinothricin or demethylphosphinothricin (Thompson et al., 1987). PPT resistant crops have been obtained by expressing the *S. hygroscopicus* bar gene in the plant nucleus. Herbicide resistant lines were obtained by direct selection for PPT resistance in culture after *Agrobacterium tumefaciens*-mediated DNA delivery in tobacco, potato, *Brassica napus* and *Brassica oleracea* (De Block et al., 1987, 1989). Biolistic DNA delivery of chimeric bar genes has been employed to obtain PPT resistant maize (Spencer et al., 1990), rice (Cao, et al, 1992) and *Arabidopsis thaliana* (Sawaskaki et al., 1994). Construction of transplastomic tobacco plants, in which PPT resistance is based on the expression of bar from *S. hygroscopicus* in plastids is described in the present example. The vectors utilized to express the bar gene contain an exemplary chimeric 5' regulatory region as set forth in the previous examples. The following material and methods facilitate the practice of this aspect of the present invention.

Construction of Plastid Bar Gene

A NcoI/XbaI bar gene fragment was generated by PCR amplification using plasmid of pDM302 (Cao et al., 1992) with the following primers:
P1,5'-AAACCATGG
CACCACAAACAGAGAGCCCAGAACGACGCCC-3' (SEQ ID NO: 58);
P2,5'-AAAATCTAGATCATCAGATCTCGGTGACG-3' (SEQ ID NO: 59).

The ends of the PCR fragment were blunt ended by treatment with the Klenow Fragment of DNA polymerase I. The fragment was then ligated into the EcoRV site of pBluescript II KS+ (Stratagene, La Jolla, Calif.) to create plasmid pJEK3. Sequence analysis of pJEK3 plasmid DNA revealed that the XbaI site we intended to create through PCR amplification of pDM302 is absent. See FIG. 19. The bar gene has the two translation termination codons followed by vector sequences. The last [20] 59 bp of pJEK3 are: CCCGTCACCGAGATCTGATGAtcgaat-tcctgcagcccgggggatccactagttctaga (bp's 552–610 of SEQ ID NO: 18). The bar sequences are in capital (stop codons underlined), the vector sequences are in lower case (XbaI site underlined). Since there is an XbaI site present in the vector 40 bp from the intended XbaI site, it was not necessary to repair this error. The NcoI-XbaI fragment from plasmid pJEK3 was ligated into NcoI-XbaI digested pGS104 plasmid (Serino and Maliga, 1997) to generate plasmid pJEK6. Plasmid pGS104 carries a Prrn-TrbcL expression cassette in a pPRV111B plastid transformation vector. A map of the plastid targeting region of plasmid pJEK6 is shown in FIG. 16A.

Plastid Transformation and Plant Regeneration

Tobacco (*Nicotiana tabacum* cv. Petit Havana) plants were grown aseptically on agar-solidified medium containing MS salts (Murashige and Skoog, 1962) and sucrose (30 g/l). Leaves were placed abaxial side up on RMOP media for bombardment. The RMOP medium consists of MS salts, N6-benzyladenine (1 mg/l), 1-naphthaleneacetic acid (0.1 mg/l), thymine (1 mg/l), inositol (100 mg/l), agar (6 g/l), pH 5.8, and sucrose (30 g/l). The DNA was introduced into chloroplasts on the surface of 1 µm tungsten particles using the DuPont PDS1000He Biolistic gun (Maliga 1995). Spectinomycin resistant clones were selected on RMOP medium containing 500 µg/ml spectinomycin dihydrochloride. Resistant shoots were regenerated on the same selective medium and rooted on MS agar medium (Svab and Maliga, 1993). The independently transformed lines are designated by the transforming plasmid (pJEK6) and a serial number, for example pJEK6-2, pJEK6-5. Plants regenerated from the same transformed line are distinguished by letters, for example pJEK6-2A, pJEK6-2B.

Southern Blot Analysis

Total cellular DNA was isolated from wild-type and transgenic spectinomycin resistant plants with CTAB (Saghai-Maroof et al., 1984). The DNA was digested with the Sma I and BglII restriction endonucleases, separated on a 0.7% agarose gel and blotted onto a Hybond-N nylon membrane (Amersham, Arlington Heights, Ill.) by a pressure blotter. The membrane was hybridized overnight with an ApaI/BamHI fragment labeled with ($\alpha$-$^{32}$P)dCTP using a dCTP DNA Labeling Beads Kit (Pharmacia Inc, Piscataway, N.J.). The membrane was washed 2 times with 0.1×SSPE, 0.2×SDS at 55° C. for 30 minutes. Film was exposed to the membrane for 30 minutes at room temperature.

PAT Assay

The PAT assay was performed as described by Spencer et. al. (1990). Leaf tissue (100 mg) from wild type tobacco (wt), transgenic Nt-pDM307-10 tobacco (a line transformed with the nuclear bar gene in plasmid pDM307; Cao et al., 1992), and plastid bar gene transformants was homogenized in 1 volume of extraction buffer (10 mM Na$_2$HPO$_4$, 10 mM NaCl). The supernatant was collected after spinning in a microfuge for 10 minutes. Protein (25 mg) was added to 1 mg/ml PPT and $^{14}$C-labeled Acetyl CoA. The reaction was incubated at 37° C. for 30 minutes and the entire reaction was spotted onto a TLC plate. Ascending chromatography was performed in a 3:2 mixture of 1-propanol and NH$_4$OH. Film was exposed to the TLC plate overnight at room temperature.

Herbicide Application

Wild type and transgenic plants were sprayed with 5 ml of a 2% solution of Liberty (AgrEvo, Wilmington, Del.) with an aerosol sprayer.

Results and Discussion

First the bacterial bar gene was converted into a plastid gene by cloning the bar coding region into a plastid expression cassette. This cassette consists of an engineered plastid rRNA operon promoter (Prrn) and TrbcL and the 3' UTR of the plastid rbcL gene for stabilization of the mRNA. The plastid bar gene was then cloned into the plastid transformation vector to yield plasmid pJEK6, and introduced into plastids on the surface of microscopic tungsten particles. The bar gene integrated into the plastid genome by two homologous recombination events via the plastid targeting sequences, as shown in FIG. 16A. Selection for the linked aadA (spectinomycin resistance) gene on spectinomycin-containing medium eventually yielded cells which carried a uniformly transformed plastid genome population, which were then regenerated into plants.

Integration of bar and aadA was verified by DNA gel blot analysis. Total cellular DNA of wild-type and transplastomic plants was digested with the SmaI and BglII restriction enzymes and probed with the 2.9-kb ApaI-BamHI plastid targeting fragment of N. tabacum (FIG. 16B). The two fragments that were expected for the transgenic plants, 3.3 kb and 1.9 kb, were present in each of the transplastomic samples shown in FIG. 16B. Absence of the 2.9 kb wild type fragment indicated, that by the time these plants have been regenerated, the wild-type plastid genome copies have been diluted out on the selective medium.

To determine if the plastid bar gene has been expressed, leaf extracts were assayed for phosphinothricin acetyltransferase (PAT) activity. Conversion of PPT into acetyl-PPT indicated PAT activity in each of the tested transplastomic lines. Data in FIG. 17 are shown for the transplastomic lines Nt-pJEK6-2D, Nt-pJEK6-5A and Nt-pJEK6-13B. Interestingly, PAT activity was significantly (>>10-fold) higher when bar was expressed in the plastids, as compared to the bar gene expressed from the cauliflower mosaic virus 35S promoter in the nucleus of the Nt-pDM307-10 plant.

PAT expression confers resistance to PPT in tissue culture and in the greenhouse. When wild type leaf sections are grown in tissue culture, 10 mg/L PPT completely blocks callus proliferation. This same PPT concentration is suitable for the selection of nuclear transformants after bombardment with the nuclear bar construct in plasmid pDM307. Leaf sections of plants expressing bar in plastids show resistance in the presence of up to 100 mg/L PPT in the culture medium. We have tested PPT resistance in the greenhouse, spraying wild-type and transplastomic plants with Liberty, a commercial formulation of PPT, at the recommended field dose of 2%. As shown in FIG. 18A, 13 days after the treatment, the wild type plants were dead while the transgenic plants thrived. Since then the sprayed plants have flowered and set seed. FIG. 18B shows maternal inheritance of PPT resistance. Lack of plastid pollen transmission results in a lack of herbicide resistance in progeny pollinated with transgenic pollen. The bacterial bar gene has a high G+C content (68.3%; Genbank Accession No. X17220), while plastid genes have a relatively high A+T content; for example the G+C content of the highly expressed psbA and rbcL genes is 42.7% and 43.7%, respectively (Genbank Accession No. Z00044). Differences in the G+C content are also reflected in the codon usage biases. Interestingly, data presented here indicate that expression of bar from *S. hygroscopicus* is sufficiently high to confer resistance to field levels of the non-selective herbicide PPT. Furthermore, the PAT enzyme levels obtained in the transplastomic lines are significantly higher than those observed in the nuclear transformant. Therefore, further improvement of the expression levels may be obtained by optimizing the codon usage for plastids as set forth in Example 7.

Advantages of incorporating bar in the plastid genome are containment of herbicide resistance due to the lack of pollen transmission in most crops. Furthermore, the lack of genetic segregation would simplify back-crossing for the introduction of herbicide resistance into additional breeding lines.

EXAMPLE 7

A Synthetic Bar Gene Improves Containment and Enhances Expression in Plastids

The bacterial bar gene was introduced into the tobacco plastid genome by transformation with plasmid pJEK6, as described above in Example 6. In plasmid pJEK6 bar is expressed in a cassette consisting of the Prrn(L)rbcL(S) promoter and TrbcL transcription terminator. This plasmid conferred PPT resistance to plants grown in the presence of PPT in the tissue culture medium, but direct selection for transformed lines was not possible. Although the PAT levels in homoplastomic leaves was high, the amount of PAT produced by the few pJEK6 bar copies during the early stage of plastid transformation was probably insufficient to protect the entire cell.

To improve bar expression in plastids a synthetic gene was created. The codon usage was modified to mimic that of the average tobacco photosynthetic plastid gene. Changing the codon usage lead to a lowered GC content characteristic of higher plant plastid genes. To assist with cloning, restriction enzyme recognition sequences were removed and added as necessary. Codon usage frequency in bacteria reflects relative tRNA abundance: frequent use of codons for rare tRNAs may significantly reduce translation efficiency. We hoped that differential codon usage in plastids and bacteria would reduce or prevent expression of the synthetic gene in bacteria, thereby reducing the danger of horizontal gene transfer to microorganisms. We also hoped that improved bar expression in our novel promoter cassettes will allow direct selection of plastid transformants on PPT-containing medium.

Materials and Methods for Example 7

Codon comparisons of photosynthetic (rbcL, psaA, psaB, psaC, psbA, psbB, psbC, psbD, psbE, psbF) plastid genes were compiled using GCG (Genetics Computer Group, Madison, Wis.). DNA mutations were then introduced into the bacterial bar gene making its codon usage more similar to plastid genes, while removing several restriction enzyme sites that could interfere with cloning. See FIG. 28. The synthetic bar gene (s-bar) was obtained by single-step assembly of the entire s-bar gene from 28 oligonucleotides (one 44 nt primer, one 30 nt primer and twenty-six 40 nt primers) using PCR (Stemmer et al., 1995). The top and bottom strands of the primers overlap with each other by 20 nucleotides. NcoI and NheI sites were added at the 5' end and a XbaI site was added at the 3' end through PCR amplification. To obtain the complete s-bar gene, a small aliquot of the assembly PCR product was amplified using primers 1A and 14B. Unchanged nucleotides are in upper case, altered nucleotides are in lower case in the primers listed below.

Primer 1A ccATGgctAGCCCAGAAaGAaGaCCGGC-CGAtATtaGaCG (SEQ ID NO: 60)
Primer 1B GCATaTCaGCtTCtGTaG-CACGtCtaATaTCGGCCGGtCt (SEQ ID NO: 61)
Primer 2A TGCtACaGAaGCtGAtATGCCaG-CaGTtTGtACaATCGTt (SEQ ID NO: 62)
Primer 2B CTTGTtTCtATaTAaTGGTTaACGATtG-TaCAaACtGCtG (SEQ ID NO: 63)
Primer 3A AACCAtTAtATaGAaACAAGtACaG-TaAACTTtaGaACtG (SEQ ID NO: 64)
Primer 3B tTCtTGaGGTTCtTGaGGtTCaGT-tCtaAAGTTtACtGTa (SEQ ID NO: 65)
Primer 4A AaCCtCAaGAACCtCAaGAaTGGACt-GAtCAtCTaGTCCG (SEQ ID NO: 66)
Primer 4B AaGGATAGCGCTCtCGtAGACGGACtA-GaTCaTCaGTCCA (SEQ ID NO: 67)
Primer 5A TCTaCGaGAGCGCTATCCtTGGCTtG-TaGCaGAaGTtGAC (SEQ ID NO: 68)
Primer 5B GCGATaCCaGCtACtTCaCCGTCaACt-TCtGCtACaAGCC (SEQ ID NO: 69)
Primer 6A GGtGAaGTaGCtGGtATCGCaTAt-GCGGGCCCtTGGAAGG (SEQ ID NO: 70)
Primer 6B CCAaTCaTAtGCaTTtCtTGCCTTC-CAaGGGCCCGCaTAt (SEQ ID NO: 71)
Primer 7A CAaGaAAtGCaTAtGAtTGGACaGCt-GAaTCaACtGTtTA (SEQ ID NO: 72)
Primer 7B GtTGaTGaCGtGGtGAaACGTAaACaGT-tGAtTCaGCtGT (SEQ ID NO: 73)
Primer 8A CGTtTCaCCaCGtCAtCAaCGtACaG-GACTtGGtTCtACt (SEQ ID NO: 74)
Primer 8B TTCAGtAGaTGtGTaTAtAGaGTaGAaC-CaAGtCCtGTaC (SEQ ID NO: 75)
Primer 9A CTaTAtACaCAtCTaCTGAAaTCttTG-GAGGCACAaGGtT (SEQ ID NO: 76)
Primer 9B aACAGCtACaACaCTCTTaAAaCCtTGT-GCCTCCAaaGAt (SEQ ID NO: 77)
Primer 10A TtAAGAGtGTtGTaGCTGTtATaGGat-TGCCtAAtGAtCC (SEQ ID NO: 78)
Primer 10B CtTCaTGCATGCGtACaCtTGGaTCaTT-aGGCAatCCtAT (SEQ ID NO: 79)
Primer 11A aAGtGTaCGCATGCAtGAaGCtCTaG-GATATGCtCCaaGa (SEQ ID NO: 80)
Primer 11B CCtGCaGCCCtCAaCATaCCtCttGGaG-CATATCCtAGaG (SEQ ID NO: 81)
Primer 12A GGtATGtTGaGGGCtGCaGGtTTCAAa-CAtGGaAACTGGC (SEQ ID NO: 82)
Primer 12B tTGCCAaAAACCtACaTCATGC-CAGTTtCCaTGtTTGAAa (SEQ ID NO: 83)
Primer 13A ATGAtGTaGGTTTtTGGCAaCT-tGAtTTCAGtCTaCCaGT (SEQ ID NO: 84)
Primer 13B GtAGaACtGGACGaGGaGGTACtGGtA-GaCTGAAaTCaAG (SEQ ID NO: 85)
Primer 14A ACCtCCtCGTCCaGTtCTaCCaGTtACt-GAGATCTGATGA (SEQ ID NO: 86)
Primer 14B tctagaTCATCAGATCTCaGTaACtG (SEQ ID NO: 87)

The amplified s-bar coding region was then cloned into a pBSIIKS+ plasmid (Stratagene, La Jolla, Calif.) and sequenced (FIG. 26A). The s-bar gene was cloned into cassettes with the chimeric PrrnLatpB+DBwt, PrrnLrbcL+DBwt and PrrnLT7g10+DB/Ec promoters. Table 6 sets forth the plasmids used in the practice of this example.

TABLE 6

Plasmids with bar genes.

| Plasmid | Promoter | bar | 3'UTR | Vector |
|---|---|---|---|---|
| pKO5 | | synthetic (s-bar) | | pBSIIKS+ |
| pKO3 | PrrnLatpB+DBwt | synthetic (s-bar) | TrbcL | pPRV111B |
| pKO8 | PrrnLrbcL+DBwt | synthetic (s-bar) | TrbcL | pPRV111A |
| pKO17 | PrrnLT7g10+DB/Ec | synthetic (s-bar) | TrbcL | pPRV111B |
| pKO12 | PrrnLrbcL+DBWt | bacterial (bar) | TrbcL | pPRV111A |

To provide a suitable cloning site at 3'-end of the bacterial bar gene, the EagI/BglII fragment of s-bar was replaced with the cognate fragment of the bacterial bar coding region. Such a bacterial bar gene is incorporated in plasmid pKO12 (FIG. 21). In plasmid pKO12 the first 22 nucleotides of the bacterial bar coding region are replaced with nucleotides from the s-bar.

Results

The engineered bacterial bar gene in pJEK6 is expressed both in *E. coli* and plants, as shown in the previous example. We were interested to test if modification of the codon affects expression of the s-bar gene in plastids and in *E. coli*. In *E. coli*, s-bar expression was determined by measuring PAT activity. Extracts were prepared from bacteria carrying plasmids pKO3 and pKO8 expressing s-bar from the PrrnLatpB+DBwt and PrrnLrbcL+DBwt promoters, respectively. The radioactive assay did not detect any activity, although extracts from bacteria transformed with plasmids pJEK6 and pKO12 carrying the bacterial bar genes gave strong signals (FIG. 22A). In plasmid pKO12 the first 22 nucleotides of the bacterial bar coding region are replaced with nucleotides from the s-bar. Therefore, lack of expression from the s-bar in *E. coli* is not due to changes within the first 22 nucleotides.

The s-bar was also introduced into plastids by transformation with vector pKO3. Extracts were prepared from pKO3- and pJEK6-transformed tobacco plants, which carry the s-bar and bar genes, respectively. Extracts from both types of plants contained significant PAT activity (FIG. 22B). Therefore, the synthetic bar is expressed in plastids but not in *E. coli*.

Changing the bar gene codon usage abrogated expression of the gene in *E. coli*. This is likely due to the introduction of the rare AGA and AGG arginine codons in the s-bar coding region. The triplet frequency per thousand nucleotides for AGA and AGG is the lowest in *E. coli*, reflecting low abundance of the tRNA required for translation of these codons. The minor arginine tRNA$^{Arg(AGG/AGA)}$ has been shown to be a limiting factor in the bacterial expression of several mammalian genes. The coexpression of ArgU (dnaY) gene that encodes for tRNA$^{Arg(AGG/AGA)}$ resulted in high level production of the target protein (Makrides 1996). The bacterial bar gene has 14 arginine codons, none of which are the rare AGA/AGG codons. The s-bar gene has five of them, three of which are located within the first 25 codons. Therefore, the likely explanation for the lack of s-bar expression in *E. coli* is introduction of the rare AGA and AGG arginine codons in the s-bar coding region.

There are proteins, which are toxic to *E. coli* but their expression is desirable in plastid to which it is not toxic. Engineering of these proteins in *E. coli* poses a problem, since the commonly used PEP plastid promoters are active in *E. coli*, thus the gene will be transcribed and the mRNA translated. Incorporation of minor codons in the coding region will prevent translation of these proteins in *E. coli*. Particularly useful in this regard is conversion of arginine codons to AGA/AGG. If no arginine is present in the N-terminal region, an N-terminal fusion may be designed containing multiple AGA/AGG codons to prevent translation of the mRNA.

Plants under field conditions are associated with microbes living in the soil, on the leaves and inside the plants. Gene flow from plastids to these microorganisms has not been shown. However, it would be an added safety measure to incorporate codons in plastid genes, which are rare in the target microorganisms, but are efficiently translated in plastids. Incorporation of AGA/AGG codons into the selective marker genes and the genes of interest will prevent transfer of genes from plants to microbes, which lack the capacity to efficiently translate the AGA/AGG codons. In case of specific plant-microbe associations, based on differences in codon usage preferences genes could be designed which would be expressed in plastids but not in microbes.

Attempts to directly select transplastomic clones after bombardment with the s-bar constructs so far has failed. The s-bar coding region in FIG. 20A contains frequent and rare codons in proportions characteristic of plastid genes. It is possible, that relatively rare codons in a specific context at a critical stage will prevent recovery of plastid transformation events. Examples for tissue-specific translation of mRNAs dependent on tRNA availability are known (Zhou et al., 1999). Therefore, we designed a second synthetic bar gene, S2-bar, containing only frequent codons (FIG. 20B). Plastid transformation with the s2-bar will enable direct selection of plastid transformation events by PPT resistance.

EXAMPLE 8

Fluorescent Antibiotic Resistance Marker for Facile Identification of Transplastomic Clones in Tobacco and Rice Plastid transformation in higher plants is accomplished through a gradual process, during which all the 300–10,000 plastid genome copies are uniformly altered. Antibiotic resistance genes incorporated in the plastid genome facilitate maintenance of transplastomes during this process. Given the high number of plastid genome copies in a cell, transformation unavoidably yields chimeric tissues, in which the transplastomic cells need to be identified and regenerated into plants. In chimeric tissue, antibiotic resistance is not cell autonomous: transplastomic and wild-type sectors both are green due to phenotypic masking by the transgenic cells. Novel genes encoding FLARE-S, a fluorescent antibiotic resistance enzyme conferring resistance to spectinomycin and streptomycin, which were obtained by translationally fusing aminoglycoside 3"-adenylyltransferase [AAD] with the *Aequorea victoria* green fluorescent protein (GFP) are provided in the present example. FLARE-S facilitates distinction of transplastomic and wild-type sectors in the chimeric tissue, thereby significantly reducing the time and effort required to obtain genetically stable transplastomic lines. The utility of FLARE-S to select for plastid transformation events was shown by tracking segregation of transplastomic and wild-type plastids in tobacco and rice plants after transformation with FLARE-S plastid vectors and selection for resistance to spectinomycin and streptomycin, respectively.

Plastid transformation vectors contain a selectable marker gene and passenger gene(s) flanked by homologous plastid targeting sequences (Zoubenko et al., 1994), and are introduced into plastids by biolistic DNA delivery (Svab et al., 1990; Svab and Maliga, 1993) or PEG treatment (Golds et al., 1993; Koop et al., 1996; O'Neill et al., 1993). The selectable marker genes may encode resistance to spectinomycin, streptomycin or kanamycin. Resistance to the drugs is conferred by the expression of chimeric aadA (Svab and Maliga, 1993) and neo (kan) (Carrer et al., 1993) genes in plastids. These drugs inhibit chlorophyll accumulation and shoot formation on plant regeneration media. The transplastomic lines are identified by the ability to form green shoots on bleached wild-type leaf sections. Obtaining a genetically stable transplastomic line involves cultivation of the cells on a selective medium, during which the cells divide at least 16 to 17 times (Moll et al., 1990). During this time wild type and transformed plastids and plastid genome copies gradually sort out. The extended period of genome and organellar sorting yields chimeric plants consisting of sectors of wild-type and transgenic cells (Maliga, 1993). In the chimeric tissue antibiotic resistance conferred by aadA or neo is not cell autonomous: transplastomic and wild-type sectors are both green due to phenotypic masking by the transgenic tissue. Chimerism necessitates a second cycle of plant regeneration on a selective medium. In the absence of a visual marker this is an inefficient process, involving antibiotic selection and identification of transplastomic plants by PCR or Southern probing. The feasibility of visual identification of transformed sectors greatly reduces the effort required to obtain homoplastomic clones.

The *Aequorea victoria* green fluorescent protein (GFP) is a visual marker, allowing direct imaging of the fluorescent gene product in living cells without the need for prolonged and lethal histochemical staining procedures. Its chromophore forms autocatalytically in the presence of oxygen and fluoresces green when absorbing blue or UV light (Prasher et al., 1992; Chalfie et al., 1994; Heim et al., 1994) (reviewed in ref. Prasher, 1995; Cubitt et al., 1995; Misteli and Spector, 1997). The gfp gene was modified for expression in the plant nucleus by removing a cryptic intron, introducing mutations to enhance brightness and to improve GFP solubility (Pang et al., 1996; Reichel et al., 1996; Rouwendal et al., 1997; Haseloff et al., 1997; Davis and Vierstra, 1998). GFP was used to monitor protein targeting to nucleus, cytoplasm and plastids from nuclear genes (Sheen et al., 1995; Chiu et al., 1996; Kŏhler et al., 1997), and to follow virus movement in plants (Baulcombe et al., 1995; Epel et al., 1996). GFP has also been used to detect transient gene expression in plastids (Hibberd et al., 1998).

The expression of GFP by directly incorporating the gfp gene in the plastid genome is described herein. Incorporation of a visual marker, the GFP protein, in the plastid transformation vectors of the present invention facilitates distinction of spontaneous antibiotic resistant mutants and plastid transformants (Svab et al., 1990). Furthermore, transplastomic sectors in the chimeric tissue can be visually identified, significantly reducing the time and effort required for obtaining genetically stable transplastomic lines. The utility of the GFP marker described here is further enhanced by its fusion with the enzyme aminoglycoside 3"-adenylyltransferase [AAD] conferring spectinomycin and streptomycin resistance to plants. Using a marker gene encoding a bifunctional protein, FLARE-S (fluorescent antibiotic resistance enzyme, spectinomycin and streptomycin), prevents physical separation of the two genes and simplifies engineering. Furthermore, fluorescent antibiotic resistance genes enables extension of plastid transformation to cereal crops, in which plastid transformation is not associated with a readily identifiable tissue culture phenotype.

The following protocols are provided to facilitate the practice of the present example.

Construction of tobacco plastid vectors. The aadA16gfp gene encodes FLARE16-S fusion protein, and can be excised as an NheI-XbaI fragment from plasmid pMSK51, a pBSKSII+ derivative (Genbank Accesssion No. Not yet assigned. The fusion protein was obtained by cloning gfp (from plasmid pCD3-326F) downstream of aadA (in plasmid pMSK38), digesting the resulting plasmid with BstXI (at the 3' end of the aadA coding region) and NcoI (including the gfp translation initiation codon) and linking the two coding regions by a BstXI-NcoI compatible adapter. The adapter was obtained by annealing oligonucleotides 5'-GTGGGCAAAGAACTTGTTGAAGGAAAATTGGA GCTAGTAGAAGGTCTTAAAGTCGC-3' (SEQ ID NO: 88) and 5'-CATGGCGACTTTAAGACCT TCTAC-TAGCTCCAATTT TCCTTCAACAAGTTCTTTGCC CACTACC-3' (SEQ ID NO: 89). The adapter connects AAD and GFP with a peptide of 16 amino acid residues (ELVEGKLELVEGLKVA; SEQ ID NO: 104).

The engineered aadA gene (Chinault et al., 1986) in plasmid pMSK38 (pBSIIKS+ derivative) has NcoI and NheI sites at the 5' end and BstXI and XbaI sites at the 3' end of the gene. The NcoI site includes the translation initiation codon; the NheI and BstXI sites are in the coding region close to the 5' and 3' ends, respectively; the XbaI site is downstream of stop codon. The mutations were introduced by PCR using oligonucleotides 5'-GGCCATGGGG GCTAGCGAAGCGGTGATCGCCGAAGTATCG-3' (SEQ ID NO: 90) and 5'-CGAATTCTAGACAT TATTTGCCCACTACCTTGGTGATCTC-3' (SEQ ID NO: 91).

The gfp gene in plasmid CD3-326F is the derivative of plasmid psmGFP, encoding the soluble modified version of GFP (accession number U70495) obtained under order number CD3-326 from the *Arabidopsis* Biological Resource Center, Columbus, Ohio (Davis and Vierstra, 1998). The gfp gene in plasmid CD3-326F is expressed in the PpsbA/TpsbA expression cassette. The gfp gene in plasmid CD3-326F was obtained through the following steps. The BamHI-SacI fragment from CD3-326 was cloned into pBSKS+ vector to yield plasmid CD3-326A. The SacI site downstream of the coding region was converted into an XbaI site by blunting and linker ligation (5'-GCTCTAGAGC; SEQ ID NO: 107; plasmid CD3-326B). An NcoI site was created to include the translation initiation codon and at the same time the internal NcoI site was removed by PCR amplification of the coding region N-terminus with primers 5'-CCGGATC CAAG-GAGATATAACACCATGGCTAGTAAAGGAG AAGAACTTTTC-3' (SEQ ID NO: 92) and 5'-GTGTTGGCCAAGGAACAGGTAGTTTTCC-3' (SEQ ID NO: 93). The PCR-amplified fragment was digested with BamHI and MscI restriction enzymes, and the resulting fragment was used to replace the BamHI-MscI fragment in plasmid CD3-326B to yield plasmid CD3-326C. The gfp coding region was excised from plasmid CD3-326C as an NcoI-XbaI fragment and cloned into a psbA cassette to yield plasmid CD3-326D. PpsbA and TpsbA are the psbA gene promoter and 3'-untranslated region derived from plasmids pJS25 (Staub and Maliga, 1993). TpsbA has been truncated by inserting a HindIII linker downstream of the modified BspHI site (Peter Hajdukiewcz, unpublished). The PpsbA::gfp::TpsbA gene was excised as an EcoRI-HindIII fragment and cloned into EcoRI and HindIII digested pPRV111A, to yield plasmid CD3-326F.

The aadA16gfp coding region from plasmid pMSK51 was introduced into two expression cassettes. In plasmid pMSK53 the aadA16gfp coding region is expressed in the PrrnLrbcL+DBwt/TpsbA cassette, and encodes the FLARE16-S2 protein (fluorescent antibiotic resistance enzyme, spectinomcyin). PrrnLrbcL+DBwt is described in the previous examples and derives from plasmid pHK14. The construct contains a chimeric promoter composed of the rrn operon promoter, the rbcL gene leader and downstream box sequence. TpsbA is the psbA gene 31 untranslated region, and functions to stabilize the chimeric mRNA. In plasmid pMSK54 the aadA26gfp coding region is expressed in the PrrnLatpB+DBwt/TpsbA cassette, and encodes the FLARE16-S1 protein. PrrnLatpB+DBwt derives from plasmid pHK10, and is a chimeric promoter composed of the rrn operon promoter, the atpB leader and downstream box sequence. See Examples 1–4.

The chimeric aadA16gfp genes were introduced into the tobacco plastid transformation vector pPRV111B (Zoubenko et al., 1994). The aadA gene was excised from plasmid pPRV111B with EcoRI and SpeI restriction enzymes, and replaced with the EcoRI-SpeI fragment from plasmids pMSK53 and pMSK54 to generate plasmids pMSK57 (aadA16gfp-S2) and pMSK56 (aadA16gfp-S1).

Construction of rice plastid vectors. Plasmid pMSK49 is a rice-specific plastid transformation vector which carries the aadA11gfp-S3 gene as the selective marker in the trnV/rps12/7 intergenic region (GenBank Accession Number: Not yet assigned). Plasmid pMSK49 carries the rice SmaI-SnaBI plastid fragment (restriction sites at nucleotides 122488 and 125 878 in the genome Hiratsuka et al., 1989) cloned into a pBSKSII+ (Stratagene) vector after blunting the SacI and KpnI restriction sites. The XbaI site present in the rice plastid DNA fragment (position at nucleotide 125032 in the genome (Hiratsuka et al., 1989) was removed by filling in and religation. Prior to cloning the selective marker the progenitor plasmid was digested with the BglII restriction enzyme giving rise to a deletion of 119 nucleotides between two proximal BglII sites (positions at 124367 and 124491). The aadA11gfp-S3 gene was then cloned in the blunted BglII sites.

The aadA gene in plasmid pMSK49 was obtained by modifying the aadA gene in plasmid pMSK38 (above) to obtain plasmid-pMSK39. The modification involved translationally fusing the aadA gene product at its N-terminus with an epitope of the human c-Myc protein (amino acids 410–419; EQKLISEEDL; SEQ ID NO: 106; Kolodziej and Young, 1991). The genetic engineering was performed by ligating an adapter obtained by annealing complementary oligonucleotides with appropriate overhangs into NcoI-NheI digested pMSK38 plasmid. The oligonucleotides were: 5'-CATGGGGGCTAGCGAACAAAAA CTCATT TCTGAAGAAGACTTGc-3' (SEQ ID NO: 94) and 5'-CTAGGCAAGTCTTCTTCAGAAATGAGTTTTTGT TCGCTAGCCCC-3' (SEQ ID NO: 95).

The aadA11gfp gene encoding FLARE11-S was obtained by linking AAD and GFP with the 11-mer peptide ELAVEGKLEVA (SEQ ID NO: 105). To clone aadA and gfp in the same polycloning site, gfp (EcoRI-HindIII fragment; from plasmid CD3-326F) was cloned downstream of aadA in plasmid pMSK39 to obtain plasmid pMSK41. The two genes were excised together as an NheI-HindIII fragment, and cloned into plasmid pMSK45 to replace a kanamycin-resistance gene yielding plasmid pMSK48. Plasmid pMSK45 is a derivative of plasmid pMSK35 which carries the PrrnLT7g10+DB/Ec promoter. The promoter consists of the plastid rRNA operon promoter and the leader sequence of the T7 phage gene 10 leader. In plasmid pMSK48, aadA is expressed from the PrrnLT7g10+DB/Ec promoter. The aadA and gfp genes were then translationally fused with an BstXI-NcoI adapter that links the AAD and GFP with an 11-mer peptide. The adapter was obtained by annealing oligonucleotides 5'-GTGGGCAAAGAACTTGCAGTT GAAGGAAAATTGGAGGTCGC-3' (SEQ ID NO: 96) and 5'-CATGGCGACCTCCAATTTTCCTTCAACTGCAAGT TCTTTGCCCACTACC-3' (SEQ ID NO: 97), which was ligated into BstXI/NcoI digested pMSK48 plasmid DNA to yield plasmid pMSK49. Plasmid pMSK49 has the rice plastid targeting sequences present in plasmid pMSK35.

Tobacco plastid transformation. Tobacco leaves from 4 to 6 weeks old plants were bombarded with DNA-coated tungsten particles using the Dupont PDS1000He Biolistic gun (1100 psi). Transplastomic clones were identified as green shoots regenerating on bleached leaf sections on RMOP medium containing 500 mg/L spectinomycin dihydrochloride (Svab abd Maliga, 1993). The spectinomycin resistant shoots were illuminated with UV light (Model B 100AP, UV Products, Upland, Calif., USA). Shoots emitting green light were transferred to spectinomycin free MS medium (Murashige and Skoog, 1962) (3% sucrose) on which fluorescent (transplastomic) and non-fluorescent (wild-type) sectors formed. Fluorescent sectors were excised, and transferred to selective (500 mg/L spectinomycin) shoot regeneration (RMOP) medium. Regenerated shoots were tested for uniform transformation by Southern analysis.

Rice plastid transformation. Callus formation from mature *Oryza sativa* cv. Taipei 309 seeds was induced on a modified CIM medium (Tompson et al., 1986), containing MS salts and vitamins (2 mg/L glycine, 0.5 mg/L nicotinic acid, 0.5 mg/L pyridoxine and 0.1 mg/L thiamine), 2 mg/L 2,4D, 1 mg/L kinetin and 300 mg/L casein enzymatic hydrolysate Type III (Sigma C-1026) and sucrose (30 g/L). Embryogenic suspensions from the proliferating embryogenic calli were obtained on the AA medium (Muller and Grafe, 1978). For plastid transformation by the biolistic process rice embryogenic cells were plated on a filter paper on non-selective modified CIM medium (Tompson et al., 1986). The bombarded cells were incubated for 48 hours, transferred to selective liquid AA medium (Muller and Grafe, 1978) (one to two weeks), and then to solid modified RRM regeneration medium (Zhang and Wu, 1988) containing MS salts and vitamins, 100 mg/L myo-inositol, 4 mg/L BAP, 0.5 mg/L IAA, 0.5 mg/L NAA, 30 g/L sucrose and 40 g/L maltose and 100 mg/L streptomycin sulfate on which green shoots appeared in two to three weeks. The shoots were rooted on a selective MS salt medium (Murashige and Skoog, 1962) containing 30 g/L sucrose and 100 mg/L streptomycin sulfate. Leaf samples for PCR analysis and confocal microscopy were taken from plants on selective medium.

PCR amplification of border fragments. Total cellular DNA was extracted according to Mettler (Mettler, 1987). The PCR analysis was carried out with a 9:1 mixture of AmpliTaq (Stratagene) and Vent (New England Biolabs) DNA polymerases in the Vent buffer following the manufacturer's recommendations. The left border fragment was amplified with primers O3 (5'-ATGGATGAACTATACAAATAAG-3'; SEQ ID NO: 98) and O4 (5'-GCTCCTATAGTGTGACG-3'; SEQ ID NO: 99). The right border fragment was amplified with primers O5 (5'-ACTACCTCTGATAGTTGAGTCG-3'; SEQ ID NO: 100) and O6 (5'-AGAGGTTAATCGTACTCTGG-3'; SEQ ID NO: 101). The aadA part of FLARE-S genes was amplified with primers O1 (5'-GGCTCCGCAGTGGATGGCGGCCTG-3'; SEQ ID NO: 102) and O2 (5'-GGGCTGATACTGGGCCGGCAGG-3'; SEQ ID NO: 103). Primer positions are shown in FIG. 5A. Note that the same primers can be used in transplastomic tobacco and rice plants expressing FLARE-S.

Detection of FLARE-S by fluorescence. FLARE-S expressing sectors in the leaves were visualized by an Olympus SZX stereo microscope equipped for GFP detection with a CCD camera system. Subcellular localization of GFP was verified by laser-scanning confocal microscopy (Sarastro 2000 Confocal Image System, Molecular Dynamics, Sunnyvale, Calif.). This system includes an argon mixed gas laser with lines at 488 and 568 nm and detector channels. The channels are adjusted for fluorescein and rhodamine images. GFP fluorescence was detected in the FITC channel (488–514 nm). Chlorophyll fluorescence was detected in the TRITC channel (560–580 nm). The images produced by GFP and chlorophyll fluorescence were viewed on a computer screen attached to the microscope and processed using the Adobe PhotoShop software.

Immunoblot analysis. Leaves (0.5 g) collected from plants in sterile culture were frozen in liquid nitrogen and ground to a fine powder in a mortar with a pestle. For protein extraction the powder was transferred to a centrifuge tube containing 1 ml buffer [50 mM Hepes/KOH (pH 7.5), 1 mM EDTA, 10 mM potassium acetate, 5 mM magnesium acetate, 1 mM dithiothreitol and 2 mM PMSF] and mixed by flicking. The insoluble material was removed by centrifugation at 4° C. for 5 min at 11,600 g. Protein concentration in the supernatant was determined using the Biorad protein assay reagent kit. Proteins (20 µl per lane) were separated in 12% SDS-PAGE (Laemmli, 1970). Proteins separated by SDS-PAGE were transferred to a Protran nitrocellulose membrane (Schleicher and Schuell) using a semi-dry electroblotting apparatus (Bio-Rad). The membrane was incubated with Living Colors Peptide Antibody (Clontech) diluted 1 to 200. FLARE-S was visualized using ECL chemilluminescence immunoblot detection on X-ray film. FLARE-S on the blots was quantified by comparison with a dilution series of commercially available purified wild-type GFP (Clontech).

Results and Discussion

Tobacco Plastid Vectors with Flare-S an the Selectable Marker.

Two FLARE-S fusion proteins were tested in E. coli. In one, the AAD and GFP were linked by an 11-mer (ELAVEGKLEVA; SEQ ID NO: 105), in the second by a 16-mer (ELVEGKLELVEGLKVA; SEQ ID NO: 104) linker. For transformation in tobacco, the aadA16gfp coding region (16-mer linker) was expressed in two cassettes known to mediate high levels of protein accumulation in plastids. Both utilize the strongest known plastid promoter driving the expression of the ribosomal RNA operon (Prrn), and the 3'-UTR of the highly expressed psbA gene (TpsbA) for the stabilization of the chimeric mRNAs. The PrrnLatpB+wtDB (plasmid pMSK56) and PrrnLrbcL+DBwt (plasmid pMSK57) promoters utilize the atpB or rbcL gene leader sequences and the coding region N-termini with the downstream box (DB) sequence, respectively. Due to inclusion of the DB sequence in the chimeric genes, the proteins encoded by the two genes are slightly different, having 14 amino acids of the ATP-ase β subunit (atpB gene products) or ribulose 1,5-bisphosphate carboxylase/oxygenase (rbcL gene product) translationally fused with FLARE16-S (FLARE16-S1 and FLARE16-S2, respectively). To obtain a plastid transformation vector with the fluorescent spectinomycin resistance genes, the chimeric genes were cloned into the trnV/rps12/7 plastid intergenic region in plastid vector pPRV111B. Plasmids pMSK56 and pMSK57 (FIG. 23) express FLARE16-S1 and FLARE16-S2, respectively, as markers.

Identification of transplastomic tobacco clones by fluorescence. Transformation was carried out by biolistic delivery of pMSK56 and pMSK57 plasmid DNA into chloroplast. The bombarded leaves were transferred onto selective (500 mg/L spectinomycin) shoot regeneration medium. Wild-type leaves on this medium bleach and form white callus. Cells with transformed plastids regenerate green shoots. The leaves on the selective medium were regularly inspected with a hand-held long-wave UV lamp for FLARE-S fluorescence.

No fluorescence could be detected in young shoots (3 to 5 mm in size) developing on pMSK56-bombarded leaves. However, formation of bright sectors in the leaves was observed, when these small shoots were transferred onto non-selective plant maintenance medium. In contrast, cultures bombarded with plasmid pMSK57 yielded small fluorescent shoots at an early stage. These fluorescent shoots, and some of the non-fluorescent ones, developed into plants with bright sectors on non-selective plant maintenance medium. Therefore, FLARE16-S2 is useful for early detection of plastid transformation events. FLARE16-S2 fluorescence in young shoots on a selective medium should be due to relatively high levels of FLARE16-S2. Higher levels of FLARE16-S2 are also indicated by the brighter sectors in variegated leaves expressing FLARE16-S2 as compared to FLARE16-S1.

The size of sectors was different in individual shoots. FLARE-S expression in different leaf layers was also obvious. With the traditional selection for spectinomycin resistance, the transplastomic and wild-type sectors are not visible. Regeneration of plants with uniformly transformed plastid genomes was greatly facilitated by the fluorescing sectors expressing FLARE-S, which could be readily identified in UV light, dissected, and transferred for a second cycle of plant regeneration on spectinomycin-containing (500 mg/L) selective medium.

Given the high levels of FLARE-S accumulation we were interested to find out, if FLARE-S is toxic to plants. We expected that toxicity should be manifested as lower transformation efficiencies. Bombardment of 30 tobacco leaves with plasmids pMSK56 and pMSK57 yielded 71 and 89 spectinomycin resistant clones, respectively. Out of these, 61 and 77 lines were verified as transplastomic by fluorescence. Plastid transformation in a subset of these was confirmed by confocal laser scanning microscopy (7 clones each; see below) and Southern analysis (4 clones). The frequency of plastid transformation events with the FLARE-S-expressing genes was slightly higher (~2 instead of ~1 per bombardment) than reported earlier with a chimeric aadA gene at the same insertion site (Svab and Maliga, 1993). Therefore, we assume that accumulation of FLARE-S at high levels is not detrimental. Lack of toxicity is also supported by the apparently normal phenotype of the plants in the greenhouse (not shown).

Localization of FLARE-S to tobacco plastids by confocal microscopy. Due to phenotypic masking, transplastomic and wild type sectors in a chimeric leaf are both green on a selective medium. However, we have found that in chimeric leaf sectors in the same cell some plastids express FLARE-S while others do not, when observed by confocal microscopy (FIG. 24). FLARE-S and chlorophyll fluorescence were detected separately in the fluorescein and rhodamine channels, respectively. The two images were then overlaid confirming that FLARE-S fluorescence derives from chloroplasts.

Expression of FLARE-S was also studied in non-green plastid types including the chromoplasts in petals and the non-green plastids in root cells (FIGS. 24b,f). These studies were carried out in plants, which were homoplastomic for the transgenomes. Homoplastomic state was important, since in non-green tissues chlorophyll could not be used for confirmation of the organelles as plastids. Since FLARE-S expression could be readily detected in chloroplasts as well as non-green plastids, the plastid rRNA operon promoter is apparently active in all plastid types.

FLARE-S accumulation in tobacco leaves. Accumulation of FLARE-S in homoplastomic leaves was tested using the commercially available GFP antibody, recognizing the GFP portion (239 amino acid residues) of FLARE16-S (520 amino acids). FLARE16-S1 (532 amino acids) was ~8%, whereas FLARE16-S2 (532 amino acids) was ~18% of total soluble leaf protein (FIG. 25). To calculate FLARE16-S concentrations, a GFP dilution series was used as a reference, and the values were than increased by 2.6 to correct for the larger size of the FLARE16-S1 and -S2 proteins.

Tracking plastid transformation in rice by FLARE-S expression. In rice, plant regeneration is from non-green embryogenic cells. Encouraged by FLARE-S expression in non-green tobacco plastids, we attempted to transform the non-green plastids of embryogenic rice tissue-culture cells. Plastid transformation was carried out using a rice-specific vector expressing FLARE11-S3 and targeting insertion of the aadA11gfp-S3 gene in the trnV/rps12/7 intergenic region. The location of the insertion site and the size of plastid targeting sequences in the rice vector are similar to the tobacco vectors shown in FIG. 23.

Plastid transformation in rice was carried out by bombardment of embryogenic rice suspension culture cells using gold particles coated with plasmid pMSK49 DNA. Rice cells, as most cereals, are naturally resistant to spectinomycin (Fromm et al., 1987). FLARE-S, however, confers resistance to streptomycin as well (Svab and Maliga, 1993). Therefore, selection for transplastomic lines was carried out on selective streptomycin medium (100 mg/L). Streptomycin at this concentration inhibits the growth of embryogenic rice cells. After bombardment, the rice cells were first solid plant regeneration medium, on which the surviving resistant cells regenerated green shoots (12 in 25 bombarded plates). These shoots were rooted, and grown into plants. PCR amplification of border fragments in DNA isolated from the leaves of these plants confirmed integration of aadA11gfp-S3 sequences in the plastid genome (FIG. 26). The left and right border fragments can not be amplified if the gene is integrated into the nuclear genome, as one of the primers (O4 or O6) of the pairs is outside the plastid targeting regions.

FLARE11-S3 expression in the leaves of two of the PCR-positive plants was tested by confocal laser-scanning microscopy. In rice, as in tobacco, the FLARE-S marker confirmed segregation of transplastomic and wild-type plastids (FIG. 27). In rice only a small fraction of chloroplasts expressed FLARE-S. Since individual cells marked with arrows in FIG. 27 contained a mixed population of wild-type and transgenic chloroplasts, FLARE-S in these cells could be expressed only from the plastid genome. Integration of aadA11gfp-S3 into the nuclear genome downstream of plastid-targeting transit peptide would result in uniform expression of FLARE-S in each of the chloroplasts within the cell.

The sequences of the selectable marker genes of the invention are provided in FIGS. 28–34. FIG. 35 depicts a table describing the selectable marker genes disclosed in the present example.

Direct visual identification of transplastomic sectors requires high level expression of FLARE-S in plastids. High GFP expression levels in *Arabidopsis* were toxic, interfering with plant regeneration. Toxicity of wild-type (insoluble) GFP was linked to GFP accumulation in the nucleus and cytoplasm, and could be eliminated by targeting it to the endoplasmic reticulum (Haseloff et al., 1997). GFP aggregates were also cytotoxic to *E. coli* cells (Crameri et al., 1996). To enhance fluorescence intensity and to avoid cytotoxicity, soluble versions of the codon-modified GFP were obtained (Davis and Vierstra, 1998). We have utilized the gene for a soluble-modified GFP described by Davis and Vierstra (Davis and Vierstra, 1998) to create variants of FLARE-S, a fusion protein, which does not have an apparent cytotoxic effect. The frequency of plastid transformation, if affected at all, is increased rather then decreased. In tobacco, we normally obtain one transplastomic clone per bombarded leaf sample (Svab and Maliga, 1993), whereas with the FLARE-S genes on average we could recover two clones per sample. Plant regeneration from highly fluorescent tissue was readily obtained, and the regenerated plants have a phenotype indistinguishable from the wild type.

Plastid transformation in rice requires expression of the selective marker in non-green plastids. The rRNA operon has two promoters, one for the eubacterial-type (PEP) and one for the phage-type (NEP) plastid RNA polymerase. The promoter driving FLARE-S expression is recognized only by the eubacterial-type plastid RNA polymerase. Previously, it was assumed that the eubacterial-type promoter is active only in chloroplasts (Maliga, 1998). Accumulation of FLARE-S in roots and petals indicates that PEP is also active in non-green plastids.

Plastid transformation is a process that unavoidably yields chimeric plants, since cells of higher plants contain a large number (300 to 50000) of plastid genome copies (Bendich, 1987), out of which initially only a few are transformed. High level expression of FLARE-S in plastids provides the means for visual identification of transplastomic sectors, even if they are present in a chimeric tissue. GFP and AAD could be expressed from two different genes in a plastid transformation vector. However, transformation with a marker gene encoding a bifunctional protein prevents separation of the two genes and simplifies engineering. The fluorescent selective marker will significantly reduce the work required to obtain genetically stable plastid transformants in tobacco, a species in which plastid transformation is routine. The bottleneck of applying plastid transformation in crop improvement is the lack of technology. In tobacco, chimeric clones with transformed plastids are readily identified by shoot regeneration (Svab et al., 1990). In *Arabidopsis*, clones with transformed plastids are identified by greening (Sikdar et al., 1998). We have shown here that FLARE-S is a suitable marker to select for transplastomes in embryogenic rice cells, which lack the visually identifiable tissue culture phenotypes exploited in tobacco and *Arabidopsis*. Data presented here are the first example for stable integration of foreign DNA into the rice plastid genome. These rice plants are heteroplastomic. Uniformly transformed rice plants will be obtained by further selection on streptomycin medium and screening the embryogenic cells for FLARE-S expression. Thus, the FLARE-S marker system will enable extension of plastid transformation to cereal crops.

The Utility of the New Chimeric Promoters

The $\sigma^{70}$-type plastid ribosomal RNA operon promoter, Prrn, is the strongest known plastid promoter expressed in all tissue types. The ultimate product of this promoter in the plastid is RNA not protein. Therefore, a series of chimeric promoters were constructed to facilitate protein accumulation from Prrn, using expression of the neomycin phosphotransferase (NPTII) enzyme as the reference protein.

1) The expression cassettes have distinct tissue-specific expression profiles. Some of the expression cassettes described here will facilitate relatively high levels of protein expression in all tissues, including leaves, roots and seeds. Other cassettes have different expression profiles: for example will facilitate moderate levels of protein accumulation in the leaves while lead to relatively high levels of protein accumulation in the roots. Accumulation of a protein at levels of 10% to 50% of total soluble protein is considered high-level protein expression; low-levels of protein expression would be in the range of $\leq 0.1$ total soluble cellular protein.

2) Efficiency of the selectable marker gene depends on the rate at which the gene product accumulates during the early stage of transformation. Since initially present only in a few copies per cell, high levels of expression from a few copies will provide protection from toxic substances early on, facilitating efficient recovery of transformed lines. The expression cassettes will be useful to drive the expression of the genes conferring resistance to the antibiotics streptomycin, spectinomycin and hygromycin, and the herbicides phosphinotrycin and glyphosate. In such applications addition of amino acids at the N-terminus is acceptable, as long as it does not interfere with the expression of the selectable marker genes. NPTII is such an enzyme. In cases like NPTII, an N-terminal fusion and thereby the mRNA "Downstream Box" sequences give an additional at least two to four-fold increase in protein levels. The –DB construct which relied on an NheI site, and involved addition of one (N-terminal) amino acid of the source gene coding region is convenient, but is not necessary. When translational fusion is not feasible due to inactivation of proteins, seamless in-frame constructs may be created by PCR methods outlined in the application.

3) A second major area on which application of the chimeric promoters is extremely useful is protein expression for pharmaceutical, industrial or agronomic purposes. The examples include, but are not restricted to, production of vaccines, healthcare products like human hemoglobin, industrial or household enzymes.

REFERENCES

Allen, G. C., Hall, G. J., Michalowski, S., Newman, W., Spiker, S., Weissinger, A. K. and Thompson, W. F. (1996) High-level transgene expression in plant cells: effects of a strong scaffold attachment region from tobacco. Plant Cell, 8, 899–913.

Allison L A, Simon L D, Maliga P (1996) Deletion of rpoB reveals a second distinct transcription system in plastids of higher plants. EMBO J. 15: 2802–2809

Arntzen, C. J. (1997) High-tech herbal medicine: plant-based vaccines [news]. Nature Biotechnology, 15, 221–222.

Baulcombe, D. C. Chapman, S. and Cruz, S. S. 1995. Jellyfish green fluorescent protein as a reporter for virus infections. Plant J. 7: 1045–1053.

Beck, E., Ludwig, G., Auerswald, E. A., Reiss, B. and Schaller, H. (1982) Nucleotide sequence and exact localization of the neomycin phosphotransferase gene from transposon Tn5. Gene, 19, 327–336.

Bendich, A. J. 1987. Why do chloroplasts and mitochondria contain so many copies of their genome? Bio-essays 6: 279–282.

Bonham-Smith, P. C. and Bourque, D. P. (1989) Translation of chloroplast-encoded mRNA: potential initiation and termination signals. Nucleic Acids Res. 17, 2057–2080.

Cao, J., Duan, X., McElroy, D., and Wu, R. (1992) Regeneration of herbicide resistant transgenic rice plants following microprojectile-mediated transformation of suspension culture cells. Plant Cell Report 11:586–591.

Carrer, H. and Maliga, P. (1995) Targeted insertion of foreign genes into the tobacco plastid genome without physical linkage to the selectable marker gene. Biotechnology, 13, 791–794.

Carrer, H., Hockenberry, T. N., Svab, Z. and Maliga, P. (1993) Kanamycin resistance as a selectable marker for plastid transformation in tobacco. Mol. Gen. Genet., 241, 49–56.

Chalfie, M., Tu, Y., Euskirchen, G., Ward, W. W. and Prasher, D. C. 1994. Green fluorescent protein as a marker for gene expression. Science 263: 802–805.

Chaudhuri, S. and Maliga, P. (1996) Sequences directing C to U editing of the plastid psbL mRNA are located within a 22 nucleotide segment spanning the editing site. EMBO J., 15, 5958–5964.

Chinault, A. C., Blakesley, V. A., Roessler, E., Willis, D. G., Smith, C. A., Cook, R. G., and Fenwick, R. G. 1986. Characterization of transferable plasmids for *Shigella flexneri* 2a that confer resistance trimethoprim, streptomycin and sulfonamides. Plasmid 15: 119–131.

Chiu, W- L., Niwa, Y., Zeng, W., Hirano, T., Kobayashi, H. and Sheen, J. 1996. Engineered gfp as a vital reporter in plants. Curr. Biol. 6: 325–330.

Conrad, U. and Fiedler, U. (1998) Compartment-specific accumulation of recombinant immunoglobulins in plant cells: an essential tool for antibody production and immunomodulation of physiological functions and pathogen activity. Plant Mol. Biol., 38, 101–109.

Corriveau, J. L., and Coleman, A. W. (1988) Rapid screening method to detect potential biparental inheritance of plastid DNA and the results for over 200 angiosperm species. Amer. J. Bot. 75:1443–1458.

Crameri, A., Whitehorn, E. A., Tate, E. and Stemmer, W. P. C. 1996. Improved green fluorescent protein by molecular evolution by DNA shuffling. Nature Biotech. 14: 315–319.

Cubitt, A. B., Heim, R., Adams, S. R., Boyd, A. E., Gross, L. A. and Tsien, R. Y. 1995. Understanding, improving and using green fluorescent proteins. Trends Biochem. Sci. 20: 448–455.

Dams, E., Hendriks, L., Van de Peer, Y., Neefs, J. M., Smits, G., Vandenbempt, I. and De Wachter, R. (1988) Compilation of small ribosomal subunit RNA sequences. Nucleic Acids Res., 16 Suppl, r87–173.

Daniell, H., Datta, R., Varma, S., Gray, S., and Lee, S. B. (1998) Containement of herbicide resistance through genetic engineering of the chloroplast genome. Nat. Biotech. 16:345–348.

Davis, S. J., and Vierstra, R. D. 1998. Soluble, highly fluorescent variants of green fluorescent protein (GFP) for use in higher plants. Plant Mol. Biol. 0.36: 521–528.

De Block, M., Botterman, J., Vandewiele, M., Dockx, J., Thoen, C., Gossele, V., Rao, Movva, N., Thompson, C., Van Montagu, M., and Leemans, J. (1987). Engineering herbicide resistance in plants by expression of a detoxifying enzyme. EMBO J. 6:2513–2518.

De Block, M., De Brouwer, D., Tenning, P. (1989). Transformation of *Brassica napus* and *Brassica oleracea* using *Agrobacterium tumefaciens* and the expression of the bar and neo genes in the transgenic plants. Plant Physiol. 91:694–701.

Deana, A., Ehrlich, R. and Reiss, C. (1998) Silent mutations in the *Escherichia coli* ompA leader peptide region strongly affect transcription and translation in vivo. Nucleic Acids Res., 26, 4778–4782.

Ellis, R. J. (1979) The most abundant protein in the world. Trends Biochem. Sci., 4, 241–244.

Epel, B. L., Padgett, H. S., Heinlein, M., and Beachy, R. 1996. Plant virus movement protein dynamics probed with GFP-protein fusion. Gene 173: 75–79.

Etchegaray, J. P. and Inouye, M. (1999) Translational enhancement by an element downstream of the initiation codon in *Escherichia coli*. J. Biol. Chem., 274, 10079–10085.

Faxin, M., Plumbridge, J. and Isaksson, L. A. (1991) Codon choice and potential complementarity between mRNA downstream of the initiation codon and bases 1471–1480 in 16S ribosomal RNA affects expression of glnS. Nucleic Acids Res., 19, 5247–5251.

Fromm, H., Edelman, M., Aviv, D. and Galun, E. 1987. The molecular basis of rRNA-dependent spectinomycin resistance in *Nicotiana* chloroplasts. EMBO J. 11: 3233–3237.

Gallo-Meagher, M., and Irvine, J. E. (1996) Herbicide resistant transgenic sugarcane plants containing the bar gene. Crop Sci. 36:1367–1374.

Golds, T., Maliga, P., and Koop, H. U. 1993. Stable plastid transformation in PEG-treated protoplasts of *Nicotiana tabaccum*. Biotechnology 11: 95–97.

Gray, A. J., and Raybould, A. F. (1988) Reducing transgene escape routes. Nature 392:653–654.

Hajdukiewicz, P., Allison, L. A., Maliga, P. (1997) The two plastid RNA polymerases encoded by the nuclear and plastid compartments transcribe distinct groups of genes in tobacco plastids. EMBO J. 16, 4041–4048.

Haseloff, J., Siemering, K. R., Prasher, D. C., and Hodge, S. 1997. Removal of a cryptic intron and subcellular localization of green fluorescent protein are required to mark transgenic *Arabidopsis* plants brightly. Proc. Natl. Acad. Sci. USA 94: 2122–2127.

Hecker, K. H. and Roux, K. H. (1996) High and low annealing temperatures increase both specificity and yield in touchdown and stepdown PCR. Biotechniques, 20, 478–485.

Heim, R., Prasher, D. C. and Tsien, R. Y. 1994. Wavelength mutations and posttranslational autooxidation of green fluorescent protein. Proc. Natl. Acad. Sci. USA 91: 12501–12504.

Hibberd, J. M., Linley, P. J., Khan, M. S., and Gray, J. C. 1998. Transient expression of green fluorescent protein in various plastid types following micro-projectile bombardment. Plant J. 16: 627–632.

Hiratsuka, J., Shimada, H., Whittier, R., Ishibashi, T., Sakamoto, M., Mori, M., Kondo, C., Honji, Y., Sun, C- R., Meng, D- Y., Li, U- Q., Kanno, A., Nishizawa, Y., Hirai, A., Shinozaki, K., and Sugiura, M. 1989. The complete sequence of the rice (Oryza sativa) chloroplast genome: Intermolecular recombination between distict tRNA genes accounts for a major plastid DNA inversion during the evolution of the cereals. Mol. Gen. Genet. 217: 185–194.

Hirose, T. and Sugiura, M. (1996) Cis-acting elements and trans-acting factors for accurate translation of chloroplast psbA mRNAs: development of an in vitro translation system from tobacco chloroplasts. EMBO J., 15, 1687–1695.

Houdt, H. V., Ingelbrecht, I., Montagu, M. V. and Depicker, A. (1997) Post-transcriptional silencing of a neomycin phosphotransferase II transgene correlates with the accumulation of unproductive RNAs and with increased cytosine methylation of 3' flanking positions. Plant J., 12, 379–392.

Ito, K., Kawakami, K. and Nakamura, Y. (1993) Multiple control of Escherichia coli lysyl-tRNA synthetase expression involves a transcriptional repressor and a translational enhancer element. Proc. Natl. Acad. Sci. USA, 90, 302–306.

Kane, J. F. (1995) Effects of rare codon clusters on high-level expression of heterologous proteins in Escherichia coli. Current Opinion In Biotechnology, 6, 494–500.

Khan, M. S. and Maliga, P. (1999) Fluorescent antibiotic resistance marker to track plastid transformation in higher plants. Nature Biotechnology, in press.

Kling, J. (1996) Could transgenic-supercrops one day breed superweeds? Science 274:180–181.

Kvhler, R. H., Cao, J., Zipfel, W. R., Webb, W. W., and Hanson, M. R. 1997. Exchange of protein molecules through connections between higher plant plastids. Science 276: 2039–2042.

Kolodziej, P. A., and Young, R. A. 1991. Epitope tagging and protein surveillance. Methods Enzymol. 194: 508–519.

Koop, H. U., Steinm|ller, K., Wagner, H., Rvssler, C., Eibl, C., and Sacher, L. 1996. Integration of foreign sequences into the tobacco plastome via PEG-mediated protoplast transformation. Planta 199: 193–101.

Kusnadi, A., Nikolov, Z. and Howard, J. (1997) Production of recombinant proteins in transgenic plants: practical considerations. Biotechnology and Bioengineering, 56, 473–484.

Laemmli, U. K. 1970. Cleavage of structural proteins during the assembly of the head of the bacteriophage T4. Nature 227: 680–685.

Lefebvre, B., Formstecher, P. and Lefebvre, P. (1995) Improvement of the gene splicing overlap method (SOE) method. BioTechniques 19: 186–187

Maier, R. M., Neckermann, K., Igloi, G. L. and Kvssel, H. (1995) Complete sequence of the maize chloroplast genome: gene content, hotspots of divergence and fine tuning of genetic information by transcript editing. J. Mol. Biol., 251, 614–628.

Makrides, S. C. (1996) Strategies for achieving high-level expression of genes in Escherichia coli. Microbiological Reviews, 60, 512–538.

Maliga P (1995). Biolistic transformation of tobacco cells with nuclear drug resistance genes. In Maliga P, Klessig D, Cashmore A, Gruissem W, Varner J (eds), Methods in Plant Molecular Biology-A Laboratory Manual. Cold Spring Harbor Laboratory Press, Cold Spring Harbor, N.Y., pp. 37–52.

Maliga, P. (1993) Towards plastid transformation in flowering plants. Trends in Biotechnology 11:101–107.

Maliga, P. 1998. Two plastid RNA polymerases of higher plants: an evolving story. Trends Plant Sci. 3: 4–6.

Mayfield, S. P., Cohen, A., Danon, A. and Yohn, C. B. (1994) Translation of the psbA mRNA of Chlamydomonas reinhardtii requires a structured RNA element contained within the 5' untranslated region. J. Cell Biol., 127, 1537–1545.

McBride, K. E., Scaaf, D. J., Daley, M. and Stalker, D. (1994) Controlled expression of plastid transgenes in plants based on a nuclear-encoded and plastid-targeted T7 RNA polymerase. Proc. Natl. Acad. Sci. USA 91, 7301–7305.

McBride, K. E., Svab, Z., Schaaf, D. J., Hogan, P. S., Stalker, D. M. and Maliga, P. (1995) Amplification of a chimeric Bacillus gene in chloroplasts leads to an extraordinary level of an insecticidal protein in tobacco. Biotechnology (N Y), 13, 362–365.

Medgyesy, P., Pay, A., and Marton, L. (1986) Transmission of paternal chloroplasts in Nicotiana. Mol. Gen. Genet. 204:195–198.

Mettler, I. J. 1987. A simple and rapid method for minipreparation of DNA from tissue-cultured plant cells. Plant Mol. Biol. Rep. 5: 346–349.

Mikkelsen, T. R., Andersen, B., and Jorgensen, R. B. (1996). The risk of crop transgene spread. Nature 380:31.

Misteli, T., and Spector, D. L. 1997. Applications of the green fluorescent protein in cell biology and biotechnology. Nature Biotech. 15: 961–964.

Mitta, M., Fang, L. and Inouye, M. (1997) Deletion analysis of cspA of Escherichia coli: requirement of the AT-rich UP element for cspA transcription and the downstream box in the coding region for its cold shock induction. Mol Microbiol, 26, 321–335.

Moll, B., Posby, L., and Maliga, P. 1990. Streptomycin and lincomycin resistance are selective plastid markers in cultured Nicotiana cells. Mol. Gen. Genet. 221: 245–250.

Muller, A. J., and Grafe, R. 1978. Isolation and characterization of cell lines of Nicotiana tobacum lacking nitrate reductase. Mol. Gen. Genet. 161: 67–76.

Murashige, T. and Skoog, F. (1962) A revised medium for the growth and bioassay with tobacco tissue culture. Physiologia Plantarum, 15, 473–497.

Nickelsen, J., Fleischmann, M., Boudreau, E., Rahire, M. and Rochaix, J. D. (1999) Identification of cis-acting RNA leader elements required for chloroplast psbD gene expression in Chlamydomonas. The Plant Cell, 11, 957–970.

Olins, P. O., Devine, C. S., Rangwala, S. H., Kavka, K. S. (1988) The T7 phage gene 10 leader RNA, a ribosome-binding site that dramatically enhances the expression of foreign genes in Escherichia coli. Gene 73: 227–235.

O'Neill, C., Horvath, G. V., Horvath, E., Dix, P. J., and Medgyesy, P. 1993. Chloroplast transformation in plants:

polyethylene glycol (PEG) treatment of protoplasts is an alternative to biolistic delivery system. Plant J. 3: 729–738.

Orozco, E. M., Chen, L. J. and Eilers, R. J. (1990) The divergently transcribed rbcL and atpB genes of tobacco plastid DNA are separated by nineteen base pairs. Curr. Genet., 17, 65–71.

Pang, S- Z., DeBoer, D. L., Wan, Y., Ye, G., Layton, J. G., Neher, M. K., Armstrong, C. L., Fry, J. E., Hinchee, M. A. W., and Fromm, M. E. 1996. An improved green fluorescent protein gene as avital marker in plants. Plant Physiol. 112: 893–900.

Prasher, D. C. 1995. Using GFP to see the light. Trends Genet. 11: 320–323.

Prasher, D. C., Eckenrode, V. K., Ward, W. W., Predergast, F. G. and Cormier, M. J. 1992. Primary structure of the Aequorea victoria green-fluorescent protein. Gene 111: 229–233.

Reichel, C., Mathur, J., Eckes, P., Langenkemper, K., Koncz, C., Schell, J., Reiss, B., and Maas, C. 1996. Enhanced green fluorescence by the expression of an Aequorea victoria green fluorescent protein mutant in mono- and dicotyledonous plant cells. Proc. Natl. Acad. Sci. USA 93: 5888–5893.

Rochaix, J. D. (1996) Post-transcriptional regulation of chloroplast gene expression in Chlamydomonas reinhardtii. Plant Mol. Biol., 32, 327–341.

Rouwendal., G. J. A., Mendes, O., Wolbert, E. J. H., and de Boer, A. D., 1997. Enhanced expression in tobacco of the gene encoding green fluorescent protein by modification of its codon usage. Plant Mol. Biol. 33: 989–999.

Saghai-Maroof, M. A., Soliman, K. M., Jorgensen, R. A., and Allard, R. W. (1984) Ribosomal DNA spacer-length polymorphisms in barley: mendelian inheritance, chromosomal location, and population dynamics. Proc. Natl. Acad. Sci. USA 81: 8014–8018.

Sakamoto, W., Kindle, K. L. and Stern, D. B. (1993) In vivo analysis of Chlamydomonas chloroplast petD gene expression using stable transformation of beta-glucuronidase translational fusions. Proc. Natl. Acad. Sci. USA, 90, 497–501.

Sawasaki, T., Seki, M., Anzai, H., Irifune, K., and Morikawa, H. (1994). Stable transformation of Arabidopsis with the bar gene using particle bombardment. Transgenic Res. 3:279–286.

Serino, G., and Maliga, P. (1997) A negative selection scheme based on the expression of cytosine deaminase in plastids. Plant J. 12:697–701.

Sheen, J., Hwang, S., Niwa, Y., Kobayashi, H., and Galbraith, D. W. 1995. Green fluorescent protein as a new vital marker in plant cells. Plant J. 8: 777–784.

Shimada, H., and Sugiura, M. (1991) Fine structural features of the chloroplast genome: comparison of the sequenced chloroplast genomes. Nucleic Acids Res. 19:983–995.

Shinozaki, K. and Sugiura, M. (1982) The nucleotide sequence of the tobacco chloroplast gene for the large subunit of ribulose-1,5-bisphosphate carboxylase/oxygenase. Gene 20: 91–102.

Shinozaki, K., Deno, H., Wakasugi, T. and Sugiura, M. (1986a) Tobacco chloroplast gene coding for subunit I of proton-translocating ATPase: comparison with the wheat subunit I and E. coli subunit b. Curr. Genet., 10, 421–423.

Shinozaki, K., Ohme, M., Tanaka, M., Wakasugi, T., Hayashida, N., Matsabayashi, T., Zaita, N., Chungwongse, J., Obokata, J., Yamaguchi-Shinozaki, K., Deno, H., Kamogashira, T., Yamada, K., Kasuda, J., Takaiwa, F., Kato, A., Todoh, N., Shimada, H. and Sugiura, M. (1986b) The complete sequence of the tobacco chloroplast genome: its gene organization and expression. EMBO J., 5, 2043–2049.

Sikdar, S. R., Serino, G., Chaudhuri, S., and Maliga, P. 1998. Plastid transformation in Arabidopsis thaliana. Plant Cell Rep. 18: 20–24.

Spencer, T. M., Gordon-Kamm, W. J., Daines, R. J., Start, W. C., and Lemaux, P. G. (1990). Bialaphos selection of stable transformants from maize cell culture. Theor. Appl. Genet. 79:625–631.

Sprengart, M. L., Fuchs, E. and Porter, A. G. (1996) The downstream box: an efficient and independent translation initiation signal in Escherichia coli. EMBO J., 15, 665–674.

Sriraman, P., Silhavy, D. and Maliga, P. (1998a) The phage-type PclpP-53 plastid promoter comprises sequences downstream of the transcription initiation site. Nucleic Acids Res., 26, 4874–4879.

Sriraman, P., Silhavy, D. and Maliga, P. (1998b) Transcription from heterologous rRNA operon promoters in chloroplasts reveals requirement for specific activating factors. Plant Physiol., 117, 1495–1499.

Sriraman, P., Silhavy, D., Maliga, P. (1998b) Transcription from heterologous ribosomal RNA operon promoters in chloroplasts reveals requirement for specific activating factors. Plant Physiol. 117: 1495–1499.

Staub, J., Maliga, P. (1993) Accumulation of D1 polypeptide in tobacco plastids is regulated via the untranslated region of the psbA mRNA. EMBO J. 12:601–606 Staub, J. M. and Maliga, P. (1994) Translation of psbA mRNA is regulated by light via the 5'-untranslated region in tobacco plastids. Plant J., 6, 547–553.

Stemmer, W. P., Crameri, A., Ha, K. D., Brennan, T. M. and Heyneker, H. L. (1995) Single-step assembly of a gene and entire plasmid from large numbers of oligodeoxyribonucleotides. Gene, 164, 49–53.

Stern, D. B., Higgs, D. C. And Yang, J. (1997) Transcription and translation in chloroplasts. Trends Plant Sci. 2, 308–315.

Stiekema W J, Heidekamp F, Dirkse W G, van Beckum J, deHaan P, ten Bosch C, Louwerse JD (1988) Molecular cloning and analysis of four potato tuber mRNAs. Plant Mol Biol 11: 255–269

Strauch, E., Wohlleben, W., and P|hler, A. (1988) Cloning of phosphinothricin acetyltransferase gene from Streptomyces viridochromogenes T|4494 and its expression in Streptomyces lividans and Escherichia coli. Gene 63:65–74.

Studier, F. W., Rosenberg, A. H., Dunn, J. J. and Dubendorff, J. W. (1990) Use of T7 RNA polymerase to direct expression of cloned genes. Methods Enzymol. 185: 60–89.

Sugita, M. and Sugiura, M. (1984) Nucleotide sequence and transcription of the gene for the 32,000 dalton thylakoid membrane protein from Nicotiana tabacum. Mol. Gen. Genet. 195: 308–313.

Svab, Z., Hajdukiewicz, P., and Maliga, P. 1990. Stable transformation of plastids in higher plants. Proc. Natl. Acad. Sci. USA 87: 8526–8530.

Svab, Z., and Maliga, P. (1993). High-frequency plastid transformation in tobacco by selection for a chimeric aadA gene. Proc. Natl. Acad. Sci. USA 90:913–917.

Tachibana. K., Watanabe. T., Sekizawa, T., and Takematsu, T. (1986) Action mechanism of bialaphos II Accumulation of ammonia in plants treated with bialaphos. J. Pest. Sci. 11:33–37.

Tanaka, M., Obokata, J., Chunwongse, J., Shinozaki, K., Sugiura, M. (1987) Rapid splicing and stepwise processing of a transcript from the psbB operon in tobacco chloroplasts: Determination of the intron sites in petb and petD. Mol. Gen. Genet. 209: 427–431.

Thompson, C. J., Movva, N. R, Tizard, R., Crameri, R., Davies, J. E., Lauwereys, M., Botterman, J. (1987) Characterization of the herbicide-resistance gene bar from *Streptomyces hygroscopicus*. EMBO J. 6:2519–2523.

Timmons, A. M., Charters, Y. M., Crawford, J. W., Burn, D., Scott, S. E., Subbels, S. J., Wilson, N. J., Robertson, A., O'Brian, E. T., Squire, G. R., and Wilkinson, M. J. (1996) Risks from transgenic crops. Nature 380:487.

Tompson, J. A., Abdullah, R., and Cocking, E. C. 1986. Protoplast culture of rice using media solidified with agarose. Plant Science 47: 123–133.

Uchida, K (1992) Recombination and amplification of multiple portions of genomic DNA by a modified polymerase chain reaction. Anal. Biochem. 202: 159–161.

Varshavsky, A. (1996) The N-end rule: Functions, mysteries, uses. Proc. Natl. Acad. Sci USA 93, 121423–12149.

Vera, A., and Sugiura M (1995). Chloroplast rRNA transcription from structurally different tandem promoters: an additional novel-type promoter. Curr. Genet. 27, 280–284.

Voorma, H. O. (1996) Control of translation in prokaryotes. In: Translational Control, Hershey, J. W. B., Methews, M. B. and Sonenberg, N., eds. pp. 759–777, Cold Spring Harbor Laboratory Press, Plainview, N. Y.

Wehrmann, A., Vliet, V. A., Opsomer, C., Bottermanm J., and Schulz, A. (1996) The bar and pat gene products make them equally applicable for plant engineers. Nat. Biotechnol. 14:1274–1278.

Wohlleben, W., Arnold, W., Broer, I., Hillemann, D., Strauch, E. and P|hler, A. (1988) Nucleotide sequence of the phosphinothricin N-acetyltransferase gene from *Streptomyces* T1949 and its expression in *Nicotiana tabacum*. Gene 70:25–37.

Wu, C. J. and Janssen, G. R. (1996) Translation of vph mRNA in *Streptomyces lividans* and *Escherichia coli* after removal of the 5' untranslated leader. Mol Microbiol, 22, 339–355.

Zerges, W., Girard-Bascou, J. and Rochaix, J. D. (1997) Translation of the chloroplast psbC mRNA is controlled by interactions between its 5' leader and the nuclear loci TBC1 and TBC3 in *Chlamydomonas* reinhardtii. Mol. Cell. Biol., 17, 3440–3448.

Zhang, W., and Wu, R. 1988. Efficient regeneration of transgenic plants from rice protoplasts and correctly regulated expression of the foreign gene in the plants. Theor. Appl. Gene. 76: 835–840.

Zhou, J., Liu, W. J., Peng, S. W., Sun, X. Y. and Frazer, I. (1999) *Papillomavirus* capsid protein expression level depends on the match between codon usage and tRNA availability. Journal Of Virology, 73, 4972–4982.

Zoubenko, O. V., Allison, L. A., Svab, Z. and Maliga, P. 1994. Efficient targeting of foreign genes into the tobacco plastid genome. Nuceic Acids Res. 22: 3819–3824.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A recombinant DNA construct for expressing at least one heterologous protein in the plastids of higher plants, wherein said construct comprises a chimeric 5' regulatory region operably linked to a coding region of said at least one heterologous protein, wherein said chimeric 5' regulatory region comprises a promoter element, a leader sequence and a downstream box element and enhances translational efficiency of an mRNA molecule encoded by said DNA construct, relative to constructs lacking said chimeric regulatory region, and wherein said chimeric 5' regulatory region is PrrnLT7g10+DB/Ec (SEQ ID NO: 14).

2. A vector comprising the DNA construct as claimed in claim 1.

3. The DNA construct as claimed in claim 1 wherein the coding region is a synthetic bar encoding nucleic acid selected from the group consisting of SEQ ID NO:19 and SEQ ID NO:20.

4. The DNA construct as claimed in claim 1, wherein said heterologous protein is a fusion protein.

5. The DNA construct as claimed in claim 4, wherein said fusion protein is encoded by a first and second coding region, wherein said first coding region encodes a selectable marker and said second coding region encodes a fluorescent molecule to facilitate visualization of transformed plant cells.

6. A vector comprising the DNA construct of claim 5.

7. The DNA construct as claimed in claim 4, wherein said fusion protein is encoded by a polynucleotide consisting of an aadA coding region operably linked to a green fluorescent protein coding region.

8. The DNA construct as claimed in claim 7, wherein said aadA coding region is operably linked to said green fluorescent protein coding region via a nucleic acid molecule encoding a peptide linker comprising an amino acid sequence selected from the group consisting of ELVEGKLELVEGLKVA (SEQ NO: 104) and ELAVEGKLEVA (SEQ ID NO: 105).

9. The DNA construct as claimed in claim 5, wherein said construct comprises a sequence selected from the group of SEQ ID NOS: 21, 22, 23, 24, and 25.

10. A plasmid for transforming the plastids of higher plants, wherein said plasmid is selected from the group consisting of PMSK49 and pMSK35.

11. A transgenic plant comprising the plasmid as claimed in claim 10.

12. The transgenic plant as claimed in claim 11, wherein said plant is a monocot or a dicot.

* * * * *

SEQUENCE LISTING

<160> NUMBER OF SEQ ID NOS: 132

<210> SEQ ID NO 1
<211> LENGTH: 227
<212> TYPE: DNA
<213> ORGANISM: Artificial Sequence
<220> FEATURE:
<223> OTHER INFORMATION: Synthetic sequence

<400> SEQUENCE: 1

```
gagctcgctc ccccgccgtc gttcaatgag aatggataag aggctcgtgg gattgacgtg      60 aggggcagg gatggctata tttctgggag aattaaccga tcgacgtgca agcggacatt     120
tattttaaat tcgataattt ttgcaaaaac atttcgacat atttatttat tttattatta     180
tgagaatcaa tcctactact tctggttctg gggtttccac ggctagc                   227
```

<210> SEQ ID NO 2
<211> LENGTH: 191
<212> TYPE: DNA
<213> ORGANISM: Artificial Sequence
<220> FEATURE:
<223> OTHER INFORMATION: Synthetic sequence

<400> SEQUENCE: 2

```
gagctcgctc ccccgccgtc gttcaatgag aatggataag aggctcgtgg gattgacgtg      60 aggggcagg gatggctata tttctgggag aattaaccga tcgacgtgca agcggacatt     120
tattttaaat tcgataattt ttgcaaaaac atttcgacat atttatttat tttattatta     180
tgagagctag c                                                          191
```

<210> SEQ ID NO 3
<211> LENGTH: 227
<212> TYPE: DNA
<213> ORGANISM: Artificial Sequence
<220> FEATURE:
<223> OTHER INFORMATION: Synthetic sequence

<400> SEQUENCE: 3

```
gagctcgctc cccgccgtc gttcaatgag aatggataag aggctcgtgg gattgacgtg      60
agggggcagg gatggctata tttctgggag aattaaccga tcgacgtgca agcggacatt    120
tattttaaat tcgataattt ttgcaaaaac atttcgacat atttatttat tttattatta    180
tgagaataaa cccgacaaca agtggaagtg gggtgtccac ggctagc                  227
```

<210> SEQ ID NO 4
<211> LENGTH: 196
<212> TYPE: DNA
<213> ORGANISM: Artificial Sequence
<220> FEATURE:
<223> OTHER INFORMATION: Synthetic sequence

<400> SEQUENCE: 4

```
gagctcgctc cccgccgtc gttcaatgag aatggataag aggctcgtgg gattgacgtg      60
agggggcagg gatggctata tttctgggag ttacgtttcc acctcaaagt gaaatatagt    120
atttagttct ttctttcatt taatgcctat tggtgttcca aaagtccctt tccgaagtcc    180
tggagaggaa gctagc                                                    196
```

<210> SEQ ID NO 5
<211> LENGTH: 154
<212> TYPE: DNA
<213> ORGANISM: Artificial Sequence
<220> FEATURE:
<223> OTHER INFORMATION: Synthetic sequence

<400> SEQUENCE: 5

```
gagctcgctc cccgccgtc gttcaatgag aatggataag aggctcgtgg gattgacgtg      60
agggggcagg gatggctata tttctgggag ttacgtttcc acctcaaagt gaaatatagt    120
atttagttct ttctttcatt taatgcctgc tagc                                154
```

<210> SEQ ID NO 6
<211> LENGTH: 195
<212> TYPE: DNA
<213> ORGANISM: Artificial Sequence
<220> FEATURE:
<223> OTHER INFORMATION: Synthetic sequence

<400> SEQUENCE: 6

```
gagctcgctc cccgccgtc gttcaatgag aatggataag aggctcgtgg gattgacgtg      60
agggggcagg gatggctata tttctgggag tcgagtagac cttgttgttg tgaaaattct    120
taattcatga gttgtaggga gggatttatg tcaccacaaa cagagactaa agcaagtgtt    180
ggattcaaag ctagc                                                     195
```

<210> SEQ ID NO 7
<211> LENGTH: 159
<212> TYPE: DNA
<213> ORGANISM: Artificial Sequence
<220> FEATURE:
<223> OTHER INFORMATION: Synthetic sequence

<400> SEQUENCE: 7

```
gagctcgctc ccccgccgtc gttcaatgag aatggataag aggctcgtgg gattgacgtg      60
agggggcagg gatggctata tttctgggag tcgagtagac cttgttgttg tgaaaattct     120
taattcatga gttgtaggga gggatttatg tcagctagc                            159

<210> SEQ ID NO 8
<211> LENGTH: 195
<212> TYPE: DNA
<213> ORGANISM: Artificial Sequence
<220> FEATURE:
<223> OTHER INFORMATION: Synthetic sequence

<400> SEQUENCE: 8
gagctcgctc ccccgccgtc gttcaatgag aatggataag aggctcgtgg gattgacgtg      60
agggggcagg gatggctata tttctgggag tcgagtagac cttgttgttg tgaaaattct     120
taattcatga gttgtaggga gggatttatg aguccucaga cagaaacaaa agccucagta     180
ggattcaaag ctagc                                                     195

<210> SEQ ID NO 9
<211> LENGTH: 195
<212> TYPE: DNA
<213> ORGANISM: Artificial Sequence
<220> FEATURE:
<223> OTHER INFORMATION: Synthetic sequence

<400> SEQUENCE: 9
gagctcgctc ccccgccgtc gttcaatgag aatggataag aggctcgtgg gattgacgtg      60
agggggcagg gatggctata tttctgggag caatgcaata aagttacgta gtgtctattt     120
atctttgata taagggtat ttccatgggt ttgccttggt atcgtgttca taccgttgta     180
ttgaatgatg ctagc                                                     195

<210> SEQ ID NO 10
<211> LENGTH: 153
<212> TYPE: DNA
<213> ORGANISM: Artificial Sequence
<220> FEATURE:
<223> OTHER INFORMATION: Synthetic sequence

<400> SEQUENCE: 10
gagctcgctc ccccgccgtc gttcaatgag aatggataag aggctcgtgg gattgacgtg      60
agggggcagg gatggctata tttctgggag caatgcaata aagttacgta gtgtctattt     120
atctttgata taagggtat ttccatggct agc                                   153

<210> SEQ ID NO 11
<211> LENGTH: 201
<212> TYPE: DNA
<213> ORGANISM: Artificial Sequence
<220> FEATURE:
<223> OTHER INFORMATION: Synthetic sequence

<400> SEQUENCE: 11
gagctcgctc ccccgccgtc gttcaatgag aatggataag aggctcgtgg gattgacgtg      60
agggggcagg gatggctata tttctgggaa aaaagccttc cattttctat tttgatttgt     120
agaaaactag tgtgcttggg agtccctgat gattaaaataa accaagattt taccatgact    180
gcaattttag agagagctag c                                              201

<210> SEQ ID NO 12
```

<211> LENGTH: 183
<212> TYPE: DNA
<213> ORGANISM: Artificial Sequence
<220> FEATURE:
<223> OTHER INFORMATION: Synthetic sequence

<400> SEQUENCE: 12
gagctcgctc cccgccgtc gttcaatgag aatggataag aggctcgtgg gattgacgtg      60
aggggcagg gatggctata tttctgggaa aaagccttc cattttctat tttgatttgt      120
agaaaactag tgtgcttggg agtccctgat gattaaataa accaagattt taccatggct    180
agc                                                                  183

<210> SEQ ID NO 13
<211> LENGTH: 185
<212> TYPE: DNA
<213> ORGANISM: Artificial Sequence
<220> FEATURE:
<223> OTHER INFORMATION: Synthetic sequence

<400> SEQUENCE: 13
gagctcgctc cccgccgtc gttcaatgag aatggataag aggctcgtgg gattgacgtg      60
aggggcagg gatggctata tttctgggag caaaaagcct tccatttct attttgattt      120
gtagaaaact agtgtgcttg ggagtccctg atgattaaat aaaccaagat tttaccatgg    180
ctagc                                                                185

<210> SEQ ID NO 14
<211> LENGTH: 182
<212> TYPE: DNA
<213> ORGANISM: Artificial Sequence
<220> FEATURE:
<223> OTHER INFORMATION: Synthetic sequence

<400> SEQUENCE: 14
gagctcgctc cccgccgtc gttcaatgag aatggataag aggctcgtgg gattgacgtg      60
aggggcagg gatggctata tttctgggag ggagaccaca acggtttccc actagaaata    120
attttgttta actttaagaa ggagatatac atatggcaag catgactggt ggacaggcta    180
gc                                                                   182

<210> SEQ ID NO 15
<211> LENGTH: 182
<212> TYPE: DNA
<213> ORGANISM: Artificial Sequence
<220> FEATURE:
<223> OTHER INFORMATION: Synthetic sequence

<400> SEQUENCE: 15
gagctcgctc cccgccgtc gttcaatgag aatggataag aggctcgtgg gattgacgtg      60
aggggcagg gatggctata tttctgggag ggagaccaca acggtttccc actagaaata    120
attttgttta actttaagaa ggagatatac atatggcaat cactagccct gccttggcta    180
gc                                                                   182

<210> SEQ ID NO 16
<211> LENGTH: 161
<212> TYPE: DNA
<213> ORGANISM: Artificial Sequence
<220> FEATURE:
<223> OTHER INFORMATION: Synthetic sequence

<400> SEQUENCE: 16

```
gagctcgctc ccccgccgtc gttcaatgag aatggataag aggctcgtgg gattgacgtg      60 aggggggcagg gatggctata tttctgggag ggagaccaca acggtttccc actagaaata    120
attttgttta actttaagaa ggagatatac atatggctag c                        161
```

```
<210> SEQ ID NO 17
<211> LENGTH: 1183
<212> TYPE: DNA
<213> ORGANISM: Artificial Sequence
<220> FEATURE:
<223> OTHER INFORMATION: Synthetic sequence

<400> SEQUENCE: 17
gagctcggta cccaaagctc ccccgccgtc gttcaatgag aatggataag aggctcgtgg      60
gattgacgtg aggggggcagg gatggctata tttctgggag cgaactccgg gcgaatacga    120
agcgcttgga tacagttgta gggagggatc catggctagc attgaacaag atggattgca    180
cgcaggttct ccggccgctt gggtggagag gctattcggc tatgactggg cacaacagac    240
aatcggctgc tctgatgccg ccgtgttccg gctgtcagcg caggggcgcc cggttctttt    300
tgtcaagacc gacctgtccg gtgccctgaa tgaactccag gacgaggcag cgcggctatc    360
gtggctggcc acgacgggcg ttccttgcgc agctgtgctc gacgttgtca ctgaagcggg    420
aagggactgg ctgctattgg gcgaagtgcc ggggcaggat ctcctgtcat ctcaccttgc    480
tcctgccgag aaagtatcca tcatggctga tgcaatgcgg cggctgcata cgcttgatcc    540
ggctacctgc ccattcgacc accaagcgaa acatcgcatc gagcgagcac gtactcggat    600
ggaagccggt cttgtcgatc aggatgatct ggacgaagag catcaggggc tcgcgccagc    660
cgaactgttc gccaggctca aggcgcgcat gcccgacggc gaggatctcg tcgtgacaca    720
tggcgatgcc tgcttgccga atatcatggt ggaaaatggc cgcttttctg gattcatcga    780
ctgtggccgg ctgggtgtgg cggaccgcta tcaggacata gcgttggcta cccgtgatat    840
tgctgaagag cttggcggcg aatgggctga ccgcttcctc gtgctttacg gtatcgccgc    900
tcccgattcg cagcgcatcg ccttctatcg ccttcttgac gagttcttct gagcgggtct    960
agagtagaca ttagcagata aattagcagg aaataaagaa ggataaggag aaagaactca   1020
agtaattatc cttcgttctc ttaattgaat tgcaattaaa ctcggcccaa tcttttacta   1080
aaaggattga gccgaataca acaaagattc tattgcatat attttgacta agtatatact   1140
tacctagata tacaagattt gaaatacaaa atctagcaag ctt                    1183
```

```
<210> SEQ ID NO 18
<211> LENGTH: 610
<212> TYPE: DNA
<213> ORGANISM: Artificial Sequence
<220> FEATURE:
<223> OTHER INFORMATION: Synthetic sequence

<400> SEQUENCE: 18
ccatggcacc acaaacagag agcccagaac gacgcccggc cgacatccgc cgtgccaccg      60
aggcggacat gccggcggtc tgcaccatcg tcaaccacta catcgagaca agcacggtca    120
acttccgtac cgagccgcag gaaccgcagg agtggacgga cgacctcgtc cgtctgcggg    180
agcgctatcc ctggctcgtc gccgaggtgg acggcgaggt cgccggcatc gcctacgcgg    240
gcccctggaa ggcacgcaac gcctacgact ggacggccga gtcgaccgtg tacgtctccc    300
cccgccacca gcggacggga ctgggctcca cgctctacac ccacctgctg aagtccctgg    360
```

```
aggcacaggg cttcaagagc gtggtcgctg tcatcgggct gcccaacgac ccgagcgtgc    420
gcatgcacga ggcgctcgga tatgcccccc gcggcatgct gcgggcggcc ggcttcaagc    480
acgggaactg gcatgacgtg ggtttctggc agctggactt cagcctgccg gtaccgcccc    540
gtccggtcct gcccgtcacc gagatctgat gatcgaattc ctgcagcccg gggatccac    600 tagttctaga                                                          610
```

<210> SEQ ID NO 19
<211> LENGTH: 566
<212> TYPE: DNA
<213> ORGANISM: Artificial Sequence
<220> FEATURE:
<223> OTHER INFORMATION: Synthetic sequence

<400> SEQUENCE: 19

```
ccatggctag cccagaaaga agaccggccg atattagacg tgctacagaa gctgatatgc    60
cagcagtttg tacaattgtt aatcattata tagaaacaag taccgtaaac tttcgaactg    120
aacctcaaga acctcaagaa tggactgatg atttagtccg tttacgagag cgctatcctt    180
ggcttgtagc agaagttgac ggagaagtag ctgggattgc atatgcgggc cgtggaaag    240 cacgaaatgc atatgattgg acggctgaat caactgtgta cgtttcacca cgtcatcaac    300
ggacaggact tggttctact ttatataccc atctactgaa atctttggag cacaggggtt    360
ttaagagtgt ggtagctgtt ataggattgc cgaatgatcc ctcggtacgc atgcacgaag    420
ctctcggata tgctcccaga ggtatgttga gggccgcagg tttcaaacat ggaaattggc    480
atgatgtagg ttttttggcaa cttgacttct ctttaccagt acctcctcgt cccgttttac    540
ccgttactga gatctgatga tctaga                                        566
```

<210> SEQ ID NO 20
<211> LENGTH: 566
<212> TYPE: DNA
<213> ORGANISM: Artificial Sequence
<220> FEATURE:
<223> OTHER INFORMATION: Synthetic sequence

<400> SEQUENCE: 20

```
ccatggctag cccagaaaga agaccggccg atattagacg tgctacagaa gctgatatgc    60
cagcagtttg tacaattgtt aatcattata tagaaacaag tacagtaaat tttcgaactg    120
aacctcaaga acctcaagaa tggactgatg atttagtacg tttacgagaa cgttatcctt    180
ggcttgtagc agaagttgac ggagaagtag ctggaattgc atatgctggt ccgtggaaag    240
cacgaaatgc atatgattgg acagctgaat caactgttta tgtttcacca cgtcatcaac    300
gtacaggact tggttctact ttatatactc atcttcttaa atctttggaa gcacaaggtt    360 ttaaagtgt agtagctgtt ataggattgc cgaatgatcc ctcagtacgc atgcatgaag    420
ctcttggata tgctcccaga ggtatgttga gggcagcagg tttcaaacat ggaaattggc    480
atgatgtagg ttttttggcaa cttgacttct ctttaccagt acctcctcgt cccgttttac    540
ccgttactga gatctgatga tctaga                                        566
```

<210> SEQ ID NO 21
<211> LENGTH: 1574
<212> TYPE: DNA
<213> ORGANISM: Artificial Sequence
<220> FEATURE:
<223> OTHER INFORMATION: Synthetic sequence

<400> SEQUENCE: 21

-continued

```
ccatggggc tagcgaagcg gtgatcgccg aagtatcgac tcaactatca gaggtagttg     60
gcgtcatcga gcgccatctc gaaccgacgt tgctggccgt acatttgtac ggctccgcag    120
tggatggcgg cctgaagcca cacagtgata ttgatttgct ggttacggtg accgtaaggc    180
ttgatgaaac aacgcggcga gctttgatca cgacctttt ggaaacttcg gcttcccctg    240
gagagagcga gattctccgc gctgtagaag tcaccattgt tgtgcacgac gacatcattc    300
cgtggcgtta tccagctaag cgcgaactgc aatttggaga atggcagcgc aatgacattc    360
ttgcaggtat cttcgagcca gccacgatcg acattgatct ggctatcttg ctgacaaaag    420
caagagaaca tagcgttgcc ttggtaggtc cagcggcgga ggaactcttt gatccggttc    480
ctgaacagga tctatttgag gcgctaaatg aaaccttaac gctatggaac tcgccgcccg    540
actgggctgg cgatgagcga aatgtagtgc ttacgttgtc ccgcatttgg tacagcgcag    600
taaccggcaa aatcgcgccg aaggatgtcg ctgccgactg gcaatggagc gcctgccgg     660
cccagtatca gcccgtcata cttgaagcta gacaggctta tcttggacaa gaagaagatc    720
gcttggcctc gcgcgcagat cagttggaag aatttgtcca ctacgtgaaa ggcgagatca    780
ccaaggtagt gggcaaagaa cttgttgaag gaaaattgga gctagtagaa ggtcttaaag    840
tcgccatggc tagtaaagga gaagaacttt tcactggagt tgtcccaatt cttgttgaat    900
tagatggtga tgttaatggg cacaaatttt ctgtcagtgg agagggtgaa ggtgatgcaa    960
catacgaaaa acttacccct aaatttattt gcactactgg aaaactacct gttccttggc   1020
caacacttgt cactactttc tcttatggtg ttcaatgctt ttcaagatac ccagatcata   1080
tgaagcggca cgacttcttc aagagcgcca tgcctgaggg atacgtgcag gagaggacca   1140
tctctttcaa ggacgacggg aactacaaga cacgtgctga gtcaagtttt gagggagaca   1200
ccctcgtcaa caggatcgag cttaagggaa tcgatttcaa ggaggacgga aacatcctcg   1260
gccacaagtt ggaatacaac tacaactccc acaacgtata catcacggca gacaaacaaa   1320
agaatggaat caaagctaac ttcaaaatta gacacaacat tgaagatgga agcgttcaac   1380
tagcagacca ttatcaacaa aatactccaa ttggcgatgg ccctgtcctt ttaccagaca   1440
accattacct gtccacacaa tctgcccttt cgaaagatcc caacgaaaag agagaccaca   1500
tggtccttct tgagtttgta acagctgctg ggattacaca tggcatggat gaactataca   1560
aataaggctc taga                                                     1574
```

<210> SEQ ID NO 22
<211> LENGTH: 1953
<212> TYPE: DNA
<213> ORGANISM: Artificial Sequence
<220> FEATURE:
<223> OTHER INFORMATION: Synthetic sequence

<400> SEQUENCE: 22

```
gagctcgctc ccccgccgtc gttcaatgag aatggataag aggctcgtgg gattgacgtg     60
aggggggcagg gatggctata tttctgggag tcgagtagac cttgttgttg tgaaaattct    120
taattcatga gttgtaggga gggatttatg tcaccacaaa cagagactaa agcaagtgtt    180
ggattcaaag ctagcgaagc ggtgatcgcc gaagtatcga ctcaactatc agaggtagtt    240
ggcgtcatcg agcgccatct cgaaccgacg ttgctggccg tacatttgta cggctccgca    300
gtggatggcg gcctgaagcc acacagtgat attgatttgc tggttacggt gaccgtaagg    360
cttgatgaaa caacgcggcg agctttgatc aacgaccttt tggaaacttc ggcttcccct    420
```

```
ggagagagcg agattctccg cgctgtagaa gtcaccattg ttgtgcacga cgacatcatt    480
ccgtggcgtt atccagctaa gcgcgaactg caatttggag aatggcagcg caatgacatt    540
cttgcaggta tcttcgagcc agccacgatc gacattgatc tggctatctt gctgacaaaa    600
gcaagagaac atagcgttgc cttggtaggt ccagcggcgg aggaactctt tgatccggtt    660
cctgaacagg atctatttga ggcgctaaat gaaaccttaa cgctatggaa ctcgccgccc    720
gactgggctg gcgatgagcg aaatgtagtg cttacgttgt cccgcatttg gtacagcgca    780
gtaaccggca aaatcgcgcc gaaggatgtc gctgccgact gggcaatgga gcgcctgccg    840
gcccagtatc agcccgtcat acttgaagct agacaggctt atcttggaca agaagaagat    900
cgcttggcct cgcgcgcaga tcagttggaa gaatttgtcc actacgtgaa aggcgagatc    960
accaaggtag tgggcaaaga acttgttgaa ggaaaattgg agctagtaga aggtcttaaa    1020
gtcgccatgg ctagtaaagg agaagaactt ttcactggag ttgtcccaat tcttgttgaa    1080
ttagatggtg atgttaatgg cacaaatttc tctgtcagtg gagagggtga aggtgatgca    1140
acatacggaa aacttaccct taaatttatt tgcactactg gaaaactacc tgttccttgg    1200
ccaacacttg tcactacttt ctcttatggt gttcaatgct tttcaagata cccagatcat    1260
atgaagcggc acgacttctt caagagcgcc atgcctgagg gatacgtgca ggagaggacc    1320
atctctttca aggacgacgg gaactacaag acacgtgctg aagtcaagtt tgagggagac    1380
accctcgtca acaggatcga gcttaaggga atcgatttca aggaggacgg aaacatcctc    1440
ggccacaagt tggaatacaa ctacaactcc cacaacgtat acatcacggc agacaaacaa    1500
aagaatggaa tcaaagctaa cttcaaaatt agacacaaca ttgaagatgg aagcgttcaa    1560
ctagcagacc attatcaaca aaatactcca attggcgatg gccctgtcct tttaccagac    1620
aaccattacc tgtccacaca atctgccctt tcgaaagatc ccaacgaaaa gagagaccac    1680
atggtccttc ttgagtttgt aacagctgct gggattacac atggcatgga tgaactatac    1740
aaataaggct ctagagcgat cctggcctag tctataggag gttttgaaaa gaaaggagca    1800
ataatcattt tcttgttcta tcaagagggt gctattgctc ctttcttttt tctttttat    1860 ttatttacta gtattttact tacatagact tttttgttta cattatagaa aaagaaggag    1920
aggttatttt cttgcattta ttcatgaaag ctt                                 1953
```

<210> SEQ ID NO 23
<211> LENGTH: 1985
<212> TYPE: DNA
<213> ORGANISM: Artificial Sequence
<220> FEATURE:
<223> OTHER INFORMATION: Synthetic sequence

<400> SEQUENCE: 23

```
gagctcgctc cccgccgtc gttcaatgag aatggataag aggctcgtgg gattgacgtg      60 aggggggcagg gatggctata tttctgggag aattaaccga tcgacgtgca agcggacatt   120
tattttaaat tcgataattt ttgcaaaaac atttcgacat atttatttat tttattatta   180
tgagaatcaa tcctactact tctggttctg gggtttccac ggctagcgaa gcggtgatcg   240
ccgaagtatc gactcaacta tcagaggtag ttggcgtcat cgagcgccat ctcgaaccga   300
cgttgctggc cgtacatttg tacgctccg cagtggatgg cggcctgaag ccacacagtg    360
atattgattt gctggttacg gtgaccgtaa ggcttgatga acaacgcgg cgagctttga   420 tcaacgacct tttggaaact tcggcttccc ctggagagag cgagattctc cgcgctgtag   480
aagtcaccat tgttgtgcac gacgacatca ttccgtggcg ttatccagct aagcgcgaac   540
```

```
tgcaatttgg agaatggcag cgcaatgaca ttcttgcagg tatcttcgag ccagccacga      600
tcgacattga tctggctatc ttgctgacaa agcaagaga acatagcgtt gccttggtag       660
gtccagcggc ggaggaactc tttgatccgg ttcctgaaca ggatctattt gaggcgctaa      720
atgaaacctt aacgctatgg aactcgccgc ccgactgggc tggcgatgag cgaaatgtag      780
tgcttacgtt gtcccgcatt tggtacagcg cagtaaccgg caaaatcgcg ccgaaggatg      840
tcgctgccga ctgggcaatg gagcgcctgc cggcccagta tcagcccgtc atacttgaag      900
ctagacaggt ttatcttgga caagaagaag atcgcttggc ctcgcgcgca gatcagttgg      960
aagaatttgt ccactacgtg aaaggcgaga tcaccaaggt agtgggcaaa gaacttgttg     1020
aaggaaaatt ggagctagta gaaggtctta agtcgccat  ggctagtaaa ggagaagaac     1080
ttttcactgg agttgtccca attcttgttg aattagatgg tgatgttaat gggcacaaat     1140
tttctgtcag tggagagggt gaaggtgatg caacatacgg aaaacttacc cttaaattta     1200
tttgcactac tggaaaacta cctgttcctt ggccaacact tgtcactact ttctcttatg     1260
gtgttcaatg cttttcaaga tacccagatc atatgaagcg gcacgacttc ttcaagagcg     1320
ccatgcctga gggatacgtg caggagagga ccatctcttt caaggacgac gggaactaca     1380
agacacgtgc tgaagtcaag tttgagggag acaccctcgt caacaggatc gagcttaagg     1440
gaatcgattt caaggaggac ggaaacatcc tcggccacaa gttggaatac aactacaact     1500
cccacaacgt atacatcacg gcagacaaac aaaagaatgg aatcaaagct aacttcaaaa     1560
ttagacacaa cattgaagat ggaagcgttc aactagcaga ccattatcaa caaaatactc     1620
caattggcga tggccctgtc cttttaccag acaaccatta cctgtccaca caatctgccc     1680
tttcgaaaga tcccaacgaa aagagagacc acatggtcct tcttgagttt gtaacagctg     1740
ctgggattac acatggcatg gatgaactat acaaataagg ctctagagcg atcctggcct     1800
agtctatagg aggttttgaa aagaaggag caataatcat tttcttgttc tatcaagagg     1860
gtgctattgc tcctttcttt ttttcttttt atttatttac tagtatttta cttacataga     1920
cttttttgtt tacattatag aaaagaagg agaggttatt tcttgcatt tattcatgaa       1980
agctt                                                                 1985

<210> SEQ ID NO 24
<211> LENGTH: 1595
<212> TYPE: DNA
<213> ORGANISM: Artificial Sequence
<220> FEATURE:
<223> OTHER INFORMATION: Synthetic sequence

<400> SEQUENCE: 24 ccatggggc tagcgaacaa aaactcattt ctgaagaaga cttgcctagc gaagcggtga       60
tcgccgaagt atcgactcaa ctatcagagg tagttggcgt catcgagcgc catctcgaac     120
cgacgttgct ggccgtacat ttgtacggct ccgcagtgga tggcggcctg aagccacaca     180
gtgatattga tttgctggtt acggtgaccg taaggcttga tgaaacaacg cggcgagctt     240
tgatcaacga ccttttggaa acttcggctt cccctggaga gagcgagatt ctccgcgctg     300
tagaagtcac cattgttgtg cacgacgaca tcattccgtg cgttatcca gctaagcgcg     360
aactgcaatt tggagaatgg cagcgcaatg acattcttgc aggtatcttc gagccagcca     420
cgatcgacat tgatctggct atcttgctga caaaagcaag agaacatagc gttgccttgg     480
taggtccagc ggcggaggaa ctctttgatc cggttcctga acaggatcta tttgaggcgc     540
```

-continued

```
taaatgaaac cttaacgcta tggaactcgc cgcccgactg ggctggcgat gagcgaaatg      600
tagtgcttac gttgtcccgc atttggtaca gcgcagtaac cggcaaaatc gcgccgaagg      660
atgtcgctgc cgactgggca atggagcgcc tgccggccca gtatcagccc gtcatacttg      720
aagctagaca ggcttatctt ggacaagaag aagatcgctt ggcctcgcgc gcagatcagt      780
tggaagaatt tgtccactac gtgaaaggcg agatcaccaa ggtagtgggc aaagaacttg      840
cagttgaagg aaaattggag gtcgccatgg ctagtaaagg agaagaactt ttcactggag      900
ttgtcccaat tcttgttgaa ttagatggtg atgttaatgg gcacaaattt tctgtcagtg      960
gagagggtga aggtgatgca acatacggaa aacttaccct taaatttatt tgcactactg     1020
gaaaactacc tgttccttgg ccaacacttg tcactacttt ctcttatggt gttcaatgct     1080
tttcaagata cccagatcat atgaagcggc acgacttctt caagagcgcc atgcctgagg     1140
gatacgtgca ggagaggacc atctctttca aggacgacgg gaactacaag acacgtgctg     1200
aagtcaagtt tgagggagac accctcgtca acaggatcga gcttaaggga atcgatttca     1260
aggaggacgg aaacatcctc ggccacaagt tggaatacaa ctacaactcc cacaacgtat     1320
acatcacggc agacaaacaa aagaatggaa tcaaagctaa cttcaaaatt agacacaaca     1380
ttgaagatgg aagcgttcaa ctagcagacc attatcaaca aaatactcca attggcgatg     1440
gccctgtcct tttaccagac aaccattacc tgtccacaca atctgccctt tcgaaagatc     1500
ccaacgaaaa gagagaccac atggtccttc ttgagtttgt aacagctgct gggattacac     1560
atggcatgga tgaactatac aaataaggct ctaga                                1595
```

<210> SEQ ID NO 25
<211> LENGTH: 1961
<212> TYPE: DNA
<213> ORGANISM: Artificial Sequence
<220> FEATURE:
<223> OTHER INFORMATION: Synthetic sequence

<400> SEQUENCE: 25

```
gagctcgctc ccccgccgtc gttcaatgag aatggataag aggctcgtgg gattgacgtg       60 aggggcagg gatggctata tttctgggag ggagaccaca acggtttccc actagaaata      120
attttgttta actttaagaa ggagatatac atatggcaag catgactggt ggacaggcta      180
gcgaacaaaa actcatttct gaagaagact tgcctagcga agcggtgatc gccgaagtat      240
cgactcaact atcagaggta gttggcgtca tcgagcgcca tctcgaaccg acgttgctgg      300
ccgtacattt gtacggctcc gcagtggatg gcggcctgaa gccacacagt gatattgatt      360
tgctggttac ggtgaccgta aggcttgatg aaacaacgcg gcgagctttg atcaacgacc      420
ttttggaaac ttcggcttcc cctggagaga gcgagattct ccgcgctgta gaagtcacca      480
ttgttgtgca cgacgacatc attccgtggc gttatccagc taagcgcgaa ctgcaatttg      540
gagaatggca gcgcaatgac attcttgcag gtatcttcga ccagccacg atcgacattg      600 atctggctat cttgctgaca aaagcaagag aacatagcgt tgccttggta ggtccagcgg      660
cggaggaact ctttgatccg gttcctgaac aggatctatt tgaggcgcta atgaaacct      720 taacgctatg gaactcgccg cccgactggg ctggcgatga gcgaaatgta gtgcttacgt      780
tgtcccgcat ttggtacagc gcagtaaccg gcaaaatcgc gccgaaggat gtcgctgccg      840
actgggcaat ggagcgcctg ccggcccagt atcagcccgt catacttgaa gctagacagg      900
cttatcttgg acaagaagaa gatcgcttgg cctcgcgcgc agatcagttg gaagaatttg      960
tccactacgt gaaaggcgag atcaccaagg tagtgggcaa agaacttgca gttgaaggaa     1020
```

```
aattggaggt cgccatggct agtaaaggag aagaactttt cactggagtt gtcccaattc    1080
ttgttgaatt agatggtgat gttaatgggc acaaattttc tgtcagtgga gagggtgaag    1140
gtgatgcaac atacgaaaaa cttaccctta aatttatttg cactactgga aaactacctg    1200
ttccttggcc aacacttgtc actactttct cttatggtgt tcaatgcttt tcaagatacc    1260
cagatcatat gaagcggcac gacttcttca agagcgccat gcctgaggga tacgtgcagg    1320
agaggaccat ctcttcaag gacgacggga actacaagac acgtgctgaa gtcaagtttg    1380
agggagacac cctcgtcaac aggatcgagc ttaagggaat cgatttcaag gaggacggaa    1440
acatcctcgg ccacaagttg aatacaact acaactccca caacgtatac atcacggcag    1500
acaaacaaaa gaatgaatc aaagctaact tcaaaattag acacaacatt gaagatggaa    1560
gcgttcaact agcagaccat tatcaacaaa atactccaat tggcgatggc cctgtccttt    1620
taccagacaa ccattacctg tccacacaat ctgcccttc gaaagatccc aacgaaaaga    1680
gagaccacat ggtccttctt gagtttgtaa cagctgctgg gattacacat ggcatggatg    1740
aactatacaa ataaggctct agagcgatcc tggcctagtc tataggaggt tttgaaaaga    1800
aaggagcaat aatcattttc ttgttctatc aagagggtgc tattgctcct ttctttttt    1860 ctttttattt atttactagt attttactta catagacttt tttgtttaca ttatagaaaa    1920
agaaggagag gttattttct tgcatttatt catgaaagct t    1961
```

<210> SEQ ID NO 26
<211> LENGTH: 4671
<212> TYPE: DNA
<213> ORGANISM: Artificial Sequence
<220> FEATURE:
<223> OTHER INFORMATION: Synthetic sequence

<400> SEQUENCE: 26

```
gggaacggat tcaccgccgt atggctgacc ggcgattact agcgattcct gcttcatgca     60
ggcgagttgc agcctgcaat ccgaactgag gacgggtttt tggagttagc tcaccctcgc    120
gagatcgcga ccctttgtcc cgcccattgt agcacgtgtg tcgcccaggg cataaggggc    180
atgatgactt ggcctcatcc tctccttcct ccggcttaac accggcggtc tgttcagggt    240
tccaaactca tagtggcaac taaacacgag ggttgcgctc gttgcgagac ttaacccaac    300
accttacggc acgagctgac gacagccatg caccacctgt gtccgcgttc ccgagggcac    360
ccctctcttt caagaggatt cgcggcatgt caagccctgg taaggttctt cgctttgcat    420
cgaattaaac cacatgctcc accgcttgtg cgggccccg tcaattcctt tgagtttcat    480
tcttgcgaac gtactcccca ggcgggatac ttaacgcgtt agctacagca ctgcacgggt    540
cgagtcgcac agcacctagt atccatcgtt tacggctagg actactgggg tctctaatcc    600
catttgctcc cctagctttc gtctctcagt gtcagtgtcg gccagcaga gtgctttcgc    660 cgttggtgtt ctttccgatc tcaatgcatt tcaccgctcc accggaaatt ccctctgccc    720
ctaccgtact ccagcttggt agtttccacc gcctgtccag ggttgagccc tgggatttga    780
cggcggactt gaaaagccac ctacagacgc tttacgccca atcattccgg ataacgcttg    840
catcctctgt cttaccgcgg ctgctggcac agagttagcc gatgcttatt cctcagatac    900
cgtcattgtt tcttctccga gaaagaagt tgacgacccg tgggccttcc acctccacgc    960
ggcattgctc cgtcaggctt tcgcccattg cggaaaattc cccactgctg cctcccgtag   1020
gagtctgggc cgtgtctcag tcccagtgtg gctgatcatc ctctcggacc agctactgat   1080
```

-continued

```
catcgccttg gtaagctatt gcctcaccaa ctagctaatc agacgcgagc ccctccttgg    1140
gcggatttct cctttttgctc ctcagcctac ggggtattag caaccgtttc cagttgttgt   1200
tcccctccca agggcaggtt cttacgcgtt actcacccgt tcgccactgg aaacaccact   1260
tcccgttcga cttgcatgtg ttaagcatgc cgccagcgtt catcctgagc caggatcgaa   1320
ctctccatga gattcatagt tgcattactt atagcttcct tattcgtaga caaagcggat   1380
tcggaattgt ctttccttcc aaggataact tgtatccatg cgcttcagat tattagcctg   1440
gagttcgcca ccagcagtat agccaaccct accctatcac gtcaatccca caagcctctt   1500
atccattccc gttcgatcgt ggcgggggga gtaagtcaaa atagaaaaaa ctcacattgg   1560
gtttagggat aatcaggctc gaactgatga cttccaccac gtcaaggtga cactctaccg   1620
ctgagttata tcccttcccc gtcccctcga gaaagagaat taccgaatcc taaggcaaag   1680
gggcgagaaa ctcaaggcca cccttcctcc gggctttctt tccacactat tatggatagt   1740
caaataatgg gaaaaattgg attcaattgt caaccggtcc tatcgaaaat aggattgact   1800
atggattcga gccatagcac atggtttcat aaaatctgta cgattttccc gatctaaatc   1860
gagcaggttt ccatgaagaa gatcgacggt atcgataagc ttgcatgcct gcaggtcgaa   1920
tatagctctt ctttcttatt tcaatgatat tattatttca aagataagag atattcaaag   1980
ataagagata gaagaagtc aaaatttgat ttttttttttg gaaaaaaaaa atcaaaagga   2040
tatagtaaca ttagcaagaa gagaaacaag ttctatttca caatttaaac aaatacaaaa   2100
tcaaaataga atactcaatc atgaataaat gcaagaaaat aacctctcct tcttttttcta  2160 taatgtaaac aaaaaaagtct atgtaagtaa aatactagta aataaataaa aagaaaaaaa   2220
gaaaggagca atagcaccct cttgatagaa caagaaaatg attattgctc ctttcttttc    2280
aaaacctcct atagactagg ccaggatcgc tctagctaga cattatttgc cgactacctt    2340
ggtgatctcg cctttcacgt agtggacaaa ttcttccaac tgatctgcgc gcgaggccaa   2400
gcgatcttct tcttgtccaa gataagcctg tctagcttca agtatgacgg gctgatactg    2460
ggccggcagg cgctccattg cccagtcggc agcgacatcc ttcggcgcga ttttgccggt    2520
tactgcgctg taccaaatgc gggacaacgt aagcactaca tttcgctcat cgccagccca    2580
gtcgggcggc gagttccata gcgttaaggt ttcatttagc gcctcaaata gatcctgttc    2640
aggaaccgga tcaaagagtt cctccgccgc tggacctacc aaggcaacgc tatgttctct    2700
tgcttttgtc agcaagatag ccagatcaat gtcgatcgtg gctggctcga agatacctgc    2760
aagaatgtca ttgcgctgcc attctccaaa ttgcagttcg cgcttagctg gataacgcca    2820
cggaatgatg tcgtcgtgca caacaatggt gacttctaca gcgcggagaa tctcgctctc    2880 tccagggga gccgaagttt ccaaaaggtc gttgatcaaa gctcgccgcg ttgtttcatc    2940
aagccttacg gtcaccgtaa ccagcaaatc aatatcactg tgtggcttca ggccgccatc    3000
cactgcggag ccgtacaaat gtacggccag caacgtcggt tcgagatggc gctcgatgac    3060
gccaactacc tctgatagtt gagtcgatac ttcggcgatc accgcttccc tcatggatcc    3120
ctccctacaa ctgtatccaa gcgcttcgta ttcgcccgga gttcgctccc agaaatatag    3180
ccatccctgc cccctcacgt caatcccacg agcctcttat ccattctcat tgaacgacgg    3240
cgggggagct ttgggtaccg agctcgaatt cctgcagccc gatcttacca tttccgaagg    3300
aactggggct acatttcttt tcaatttcca ttcaagagtt tcttatctgt ttccacgccc    3360 tttttttgaga cctcgaaaca tgaaatggac aaattccttc tcttaggaac acatacaaga    3420
aaaaggataa tggtagccct cccattaact acttcatttc atttatgaat ttcatagtaa    3480
```

-continued

```
tagaaatcca tgtcctaccg agacagaatt tcgaacttgc tatcctcttg cctaataggc    3540
aaagattgac ctctgtagaa agaatgattc attcggatcg atatgaggac ccaactacgt    3600
tgcattgcag aatccatgtt ccatatttga agagggttga cctctgtgct tctctcatgg    3660
tacaatcctc ttcctgctga gccccctttc tcctcggtcc acagagaaaa aatggaggac    3720
tggtgccgac agttcatcac ggaagaaaga actcacagag ccgggatcgc taactaatag    3780
aatagtacta ctaactaata ctaatatata gaaatagata tctagctaga aatagaaaca    3840
actaatatat agataatcga aattgaaaag aactgtcttt tctgtatact ttccccgttc    3900
tattgctacc gcgggtctta tgcaatcgat cggatcatat agatatccct tcaacacaac    3960
ataggtcatc gaaaggatct cggacgactc accaaagcac gaaagccagt tagaaaatgg    4020
attcctattt gaagagtgcc taaccgcatg gataagctca cattaacccg tcaattttgg    4080
atccaattcg ggattttcct tgggaagttt cgggaagaaa ttggaatgga ataatataga    4140
ttcatacaga ggaaaaggtt ctctattgat gcaaacgctg tacctagagg atagggatag    4200
aggaagaggg aaaaatcgaa atgaaataaa taagaataa agcaaaaaaa aaataagtcg    4260
aagatagaag agcccagatt ccaaatgaag aaatggaaac tcgaaaagga tccttctgat    4320
tctcaaagaa tgaggggcaa ggggattgat accgagaaag atttcttctt attataagac    4380
gtgatttgat ccgcatatgt ttggtaaaag aacaatcttc tcctttaatc ataaatggaa    4440
agtgttcaat tagaacatga aaacgtgact caattggtct tagttagtct tcggacgga     4500 gtggaagaaa gggcgaagac ctctcgaacga ggaaaaggat cccttcgaaa gaattgaacg    4560
aggagccgta ttaggtgaaa atctcatgta cgattctgta gagggacagg aagggtgact    4620
tatctgtcga cttttccact atcaaccca aaaaacccaa ctctgcctta c              4671
```

<210> SEQ ID NO 27
<211> LENGTH: 5263
<212> TYPE: DNA
<213> ORGANISM: Artificial Sequence
<220> FEATURE:
<223> OTHER INFORMATION: Synthetic sequence

<400> SEQUENCE: 27

```
gggaacggat tcaccgccgt atggctgacc ggcgattact agcgattcct gcttcatgca     60
ggcgagttgc agcctgcaat ccgaactgag gacgggtttt tggagttagc tcaccctcgc    120
gagatcgcga ccctttgtcc cgcccattgt agcacgtgtg tcgcccaggg cataaggggc    180
atgatgactt ggcctcatcc tctccttcct ccggcttaac accggcggtc tgttcagggt    240
tccaaactca tagtggcaac taaacacgag ggttgcgctc gttgcgagac ttaacccaac    300
accttacggc acgagctgac gacagccatg caccacctgt gtccgcgttc ccgagggcac    360
ccctctcttt caagaggatt cgcggcatgt caagccctgg taaggttctt cgctttgcat    420
cgaattaaac cacatgctcc accgcttgtg cgggccccg tcaattcctt tgagtttcat    480
tcttgcgaac gtactcccca ggcgggatac ttaacgcgtt agctacagca ctgcacgggt    540
cgagtcgcac agcacctagt atccatcgtt tacggctagg actactgggg tctctaatcc    600
catttgctcc cctagctttc gtctctcagt gtcagtgtcg gcccagcaga gtgctttcgc    660
cgttggtgtt ctttccgatc tcaatgcatt tcaccgctcc accggaaatt ccctctgccc    720
ctaccgtact ccagcttggt agttccaccc gcctgtccag ggttgagccc tgggatttga    780
cggcggactt gaaaagccac ctacagacgc tttacgccca atcattccgg ataacgcttg    840
```

```
catcctctgt cttaccgcgg ctgctggcac agagttagcc gatgcttatt cctcagatac      900
cgtcattgtt tcttctccga gaaaagaagt tgacgacccg tgggccttcc acctccacgc      960
ggcattgctc cgtcaggctt tcgcccattg cggaaaattc cccactgctg cctcccgtag     1020
gagtctgggc cgtgtctcag tcccagtgtg gctgatcatc ctctcggacc agctactgat     1080
catcgccttg gtaagctatt gcctcaccaa ctagctaatc agacgcgagc ccctccttgg     1140
gcggatttct ccttttgctc ctcagcctac ggggtattag caaccgtttc cagttgttgt     1200
tcccctccca agggcaggtt cttacgcgtt actcacccgt tcgccactgg aaacaccact     1260
tcccgttcga cttgcatgtg ttaagcatgc cgccagcgtt catcctgagc caggatcgaa     1320
ctctccatga gattcatagt tgcattactt atagcttcct tattcgtaga caaagcggat     1380
tcggaattgt ctttccttcc aaggataact tgtatccatg cgcttcagat tattagcctg     1440
gagttcgcca ccagcagtat agccaaccct accctatcac gtcaatccca caagcctctt     1500
atccattccc gttcgatcgt ggcgggggga gtaagtcaaa atagaaaaaa ctcacattgg     1560
gtttagggat aatcaggctc gaactgatga cttccaccac gtcaaggtga cactctaccg     1620
ctgagttata tccttccccc gtcccctcga gaaagagaat taccgaatcc taaggcaaag     1680
gggcgagaaa ctcaaggcca cccttcctcc gggctttctt tccacactat tatggatagt     1740
caaataatgg gaaaaattgg attcaattgt caaccggtcc tatcgaaaat aggattgact     1800
atggattcga gccatagcac atggtttcat aaaatctgta cgattttccc gatctaaatc     1860
gagcaggttt ccatgaagaa gatcgacggt atcgataagc tttcatgaat aaatgcaaga     1920
aaataacctc tccttctttt tctataatgt aaacaaaaaa gtctatgtaa gtaaaatact     1980
agtaaataaa taaaagaaa aaagaaaagg agcaatagca ccctcttgat agaacaagaa     2040
aatgattatt gctcctttct tttcaaaacc tcctatagac taggccagga tcgctctaga     2100
gccttatttg tatagttcat ccatgccatg tgtaatccca gcagctgtta caaactcaag     2160
aaggaccatg tggtctctct tttcgttggg atctttcgaa agggcagatt gtgtggacag     2220
gtaatggttg tctggtaaaa ggacagggcc atcgccaatt ggagtatttt gttgataatg     2280
gtctgctagt tgaacgcttc catcttcaat gttgtgtcta attttgaagt tagctttgat     2340
tccattcttt tgtttgtctg ccgtgatgta tacgttgtgg gagttgtagt tgtattccaa     2400
cttgtggccg aggatgtttc cgtcctcctt gaaatcgatt cccttaagct cgatcctgtt     2460
gacgagggtg tctccctcaa acttgacttc agcacgtgtc ttgtagttcc cgtcgtcctt     2520
gaaagagatg gtccctctcct gcacgtatcc ctcaggcatg gcgctcttga agaagtcgtg     2580
ccgcttcata tgatctgggt atcttgaaaa gcattgaaca ccataagaga agtagtgac      2640 aagtgttggc caaggaacag gtagttttcc agtagtgcaa ataaatttaa gggtaagttt     2700
tccgtatgtt gcatcacctt caccctctcc actgacagaa aatttgtgcc cattaacatc     2760
accatctaat tcaacaagaa ttgggacaac tccagtgaaa agttcttctc ctttactagc     2820
catggcgacc tccaattttc cttcaactgc aagttctttg cccactacct tggtgatctc     2880
gcctttcacg tagtggacaa attcttccaa ctgatctgcg cgcgaggcca agcgatcttc     2940
ttcttgtcca agataagcct gtctagcttc aagtatgacg ggctgatact gggccggcag     3000
gcgctccatt gcccagtcgg cagcgacatc cttcggcgcg attttgccgg ttactgcgct     3060
gtaccaaatg cgggacaacg taagcactac atttcgctca tcgccagccc agtcgggcgg     3120
cgagttccat agcgttaagg tttcatttag cgcctcaaat agatcctgtt caggaaccgg     3180
atcaaagagt tcctccgccg ctggacctac caaggcaacg ctatgttctc ttgcttttgt     3240
```

-continued

```
cagcaagata gccagatcaa tgtcgatcgt ggctggctcg aagatacctg caagaatgtc    3300
attgcgctgc cattctccaa attgcagttc gcgcttagct ggataacgcc acggaatgat    3360
gtcgtcgtgc acaacaatgg tgacttctac agcgcggaga atctcgctct ctccagggga    3420
agccgaagtt tccaaaaggt cgttgatcaa agctcgccgc gttgtttcat caagccttac    3480
ggtcaccgta accagcaaat caatatcact gtgtggcttc aggccgccat ccactgcgga    3540
gccgtacaaa tgtacggcca gcaacgtcgg ttcgagatgg cgctcgatga cgccaactac    3600
ctctgatagt tgagtcgata cttcggcgat caccgcttcg ctaggcaagt cttcttcaga    3660
aatgagtttt tgttcgctag cctgtccacc agtcatgctt gccatatgta tatctccttc    3720
ttaaagttaa acaaaattat ttctagtggg aaaccgttgt ggtctccctc ccagaaatat    3780
agccatccct gcccctcac gtcaatccca cgagcctctt atccattctc attgaacgac    3840
ggcgggggag cgagctcgaa ttcctgcagc ccgatcttac catttccgaa ggaactgggg    3900
ctacatttct tttcaatttc cattcaagag tttcttatct gtttccacgc ccttttttga    3960
gacctcgaaa catgaaatgg acaaattcct tctcttagga acacatacaa gaaaaaggat    4020
aatggtagcc ctcccattaa ctacttcatt tcatttatga atttcatagt aatagaaatc    4080
catgtcctac cgagacagaa tttcgaactt gctatcctct tgcctaatag gcaaagattg    4140
acctctgtag aaagaatgat tcattcggat cgatatgagg acccaactac gttgcattgc    4200
agaatccatg ttccatattt gaagagggtt gacctctgtg cttctctcat ggtacaatcc    4260
tcttcctgct gagcccccctt tctcctcggt ccacagagaa aaaatggagg actggtgccg    4320
acagttcatc acggaagaaa gaactcacag agccgggatc gctaactaat agaatagtac    4380
tactaactaa tactaatata tagaaataga tatctagcta gaaatagaaa caactaatat    4440
atagataatc gaaattgaaa agaactgtct tttctgtata ctttccccgt tctattgcta    4500
ccgcgggtct tatgcaatcg atcggatcat atagatatcc cttcaacaca acataggtca    4560
tcgaaaggat ctcggacgac tcaccaaagc acgaaagcca gttagaaaat ggattcctat    4620
ttgaagagtg cctaaccgca tggataagct cacattaacc cgtcaatttt ggatccaatt    4680
cgggattttt cttgggaagt ttcgggaaga aattggaatg gaataatata gattcataca    4740
gaggaaaagg ttctctattg atgcaaacgc tgtacctaga ggatagggat agaggaagag    4800
ggaaaaatcg aaatgaaata aataaagaat aaagcaaaaa aaaataagt cgaagataga    4860
agagcccaga ttccaaatga agaaatgaa actcgaaaag gatccttctg attctcaaag    4920
aatgagggc aagggattg ataccgagaa agatttcttc ttattataag acgtgatttg    4980
atccgcatat gtttggtaaa agaacaatct tctcctttaa tcataaatgg aaagtgttca    5040
attagaacat gaaaacgtga ctcaattggt cttagttagt cttcgggacg gagtggaaga    5100
aagggcgaag actctcgaac gaggaaaagg atcccttcga aagaattgaa cgaggagccg    5160
tattaggtga aaatctcatg tacgattctg tagagggaca ggaagggtga cttatctgtc    5220
gactttccca ctatcaaccc caaaaaaccc aactctgcct tac                      5263
```

<210> SEQ ID NO 28
<211> LENGTH: 11
<212> TYPE: DNA
<213> ORGANISM: Artificial Sequence
<220> FEATURE:
<223> OTHER INFORMATION: Synthetic sequence

<400> SEQUENCE: 28

```
uaaggaggug a                                                              11

<210> SEQ ID NO 29
<211> LENGTH: 26
<212> TYPE: DNA
<213> ORGANISM: Artificial Sequence
<220> FEATURE:
<223> OTHER INFORMATION: Synthetic sequence

<400> SEQUENCE: 29
tccagtcact agccctgcct tcggca                                              26

<210> SEQ ID NO 30
<211> LENGTH: 26
<212> TYPE: DNA
<213> ORGANISM: Artificial Sequence
<220> FEATURE:
<223> OTHER INFORMATION: Synthetic sequence

<400> SEQUENCE: 30
cccagtcatg aatcacaaag tggtaa                                              26

<210> SEQ ID NO 31
<211> LENGTH: 27
<212> TYPE: DNA
<213> ORGANISM: Artificial Sequence
<220> FEATURE:
<223> OTHER INFORMATION: Synthetic sequence

<400> SEQUENCE: 31
cccgagctcg ctcccccgcc gtcgttc                                             27

<210> SEQ ID NO 32
<211> LENGTH: 64
<212> TYPE: DNA
<213> ORGANISM: Artificial Sequence
<220> FEATURE:
<223> OTHER INFORMATION: Synthetic sequence

<400> SEQUENCE: 32
cgaatttaaa ataaatgtcc gcttgcacgt cgatcggtta attctcccag aaatatagcc         60
atcc                                                                      64

<210> SEQ ID NO 33
<211> LENGTH: 27
<212> TYPE: DNA
<213> ORGANISM: Artificial Sequence
<220> FEATURE:
<223> OTHER INFORMATION: Synthetic sequence

<400> SEQUENCE: 33
cccgctagcc gtggaaaccc cagaacc                                             27

<210> SEQ ID NO 34
<211> LENGTH: 39
<212> TYPE: DNA
<213> ORGANISM: Artificial Sequence
<220> FEATURE:
<223> OTHER INFORMATION: Synthetic sequence

<400> SEQUENCE: 34
cccgctagct ctcataataa taaataaat aaatatgtc                                 39

<210> SEQ ID NO 35
<211> LENGTH: 43
```

```
<212> TYPE: DNA
<213> ORGANISM: Artificial Sequence
<220> FEATURE:
<223> OTHER INFORMATION: Synthetic sequence

<400> SEQUENCE: 35
tcactttgag gtggaaacgt aactcccaga aatatagcca tcc                    43

<210> SEQ ID NO 36
<211> LENGTH: 27
<212> TYPE: DNA
<213> ORGANISM: Artificial Sequence
<220> FEATURE:
<223> OTHER INFORMATION: Synthetic sequence

<400> SEQUENCE: 36
cccgctagct tcctctccag gacttcg                                      27

<210> SEQ ID NO 37
<211> LENGTH: 32
<212> TYPE: DNA
<213> ORGANISM: Artificial Sequence
<220> FEATURE:
<223> OTHER INFORMATION: Synthetic sequence

<400> SEQUENCE: 37
cccgctagca ggcattaaat gaaagaaaga ac                                32

<210> SEQ ID NO 38
<211> LENGTH: 53
<212> TYPE: DNA
<213> ORGANISM: Artificial Sequence
<220> FEATURE:
<223> OTHER INFORMATION: Synthetic sequence

<400> SEQUENCE: 38
taagaatttt cacaacaaca aggtctactc gactcccaga aatatagcca tcc         53

<210> SEQ ID NO 39
<211> LENGTH: 32
<212> TYPE: DNA
<213> ORGANISM: Artificial Sequence
<220> FEATURE:
<223> OTHER INFORMATION: Synthetic sequence

<400> SEQUENCE: 39
cccgctagct ttgaatccaa cacttgcttt ag                                32

<210> SEQ ID NO 40
<211> LENGTH: 29
<212> TYPE: DNA
<213> ORGANISM: Artificial Sequence
<220> FEATURE:
<223> OTHER INFORMATION: Synthetic sequence

<400> SEQUENCE: 40
cccgctagct gacataaatc cctccctac                                    29

<210> SEQ ID NO 41
<211> LENGTH: 58
<212> TYPE: DNA
<213> ORGANISM: Artificial Sequence
<220> FEATURE:
<223> OTHER INFORMATION: Synthetic sequence

<400> SEQUENCE: 41
```
caaagataaa tagacactac gtaactttat tgcattgctc ccagaaatat agccatcc      58

<210> SEQ ID NO 42
<211> LENGTH: 36
<212> TYPE: DNA
<213> ORGANISM: Artificial Sequence
<220> FEATURE:
<223> OTHER INFORMATION: Synthetic sequence

<400> SEQUENCE: 42
cccgctagca tcattcaata caacggtatg aacacg      36

<210> SEQ ID NO 43
<211> LENGTH: 48
<212> TYPE: DNA
<213> ORGANISM: Artificial Sequence
<220> FEATURE:
<223> OTHER INFORMATION: Synthetic sequence

<400> SEQUENCE: 43
ttctagtggg aaaccgttgt ggtctccctc ccagaaatat agccatcc      48

<210> SEQ ID NO 44
<211> LENGTH: 33
<212> TYPE: DNA
<213> ORGANISM: Artificial Sequence
<220> FEATURE:
<223> OTHER INFORMATION: Synthetic sequence

<400> SEQUENCE: 44
cccgctagcc atatgtatat ctccttctta aag      33

<210> SEQ ID NO 45
<211> LENGTH: 34
<212> TYPE: DNA
<213> ORGANISM: Artificial Sequence
<220> FEATURE:
<223> OTHER INFORMATION: Synthetic sequence

<400> SEQUENCE: 45
cccgctagcc tgtccaccag tcatgcttgc cata      34

<210> SEQ ID NO 46
<211> LENGTH: 48
<212> TYPE: DNA
<213> ORGANISM: Artificial Sequence
<220> FEATURE:
<223> OTHER INFORMATION: Synthetic sequence

<400> SEQUENCE: 46
cccgctagcc aaggcagggc tagtgattgc catatgtata tctccttc      48

<210> SEQ ID NO 47
<211> LENGTH: 50
<212> TYPE: DNA
<213> ORGANISM: Artificial Sequence
<220> FEATURE:
<223> OTHER INFORMATION: Synthetic sequence

<400> SEQUENCE: 47
tttgtttaac tttaagaagg agatatacat atggcaagca tgactggtgg      50

<210> SEQ ID NO 48
<211> LENGTH: 47
<212> TYPE: DNA
<213> ORGANISM: Artificial Sequence

```
<220> FEATURE:
<223> OTHER INFORMATION: Synthetic sequence

<400> SEQUENCE: 48
ctccttctta aagttaaaca aaattatttc tagtgggaaa ccgttgt                    47

<210> SEQ ID NO 49
<211> LENGTH: 48
<212> TYPE: DNA
<213> ORGANISM: Artificial Sequence
<220> FEATURE:
<223> OTHER INFORMATION: Synthetic sequence

<400> SEQUENCE: 49
caaaatagaa aatggaaggc tttttgctcc cagaaatata gccatccc                  48

<210> SEQ ID NO 50
<211> LENGTH: 46
<212> TYPE: DNA
<213> ORGANISM: Artificial Sequence
<220> FEATURE:
<223> OTHER INFORMATION: Synthetic sequence

<400> SEQUENCE: 50
caaaatagaa aatggaaggc ttttttccca gaaatatagc catccc                    46

<210> SEQ ID NO 51
<211> LENGTH: 31
<212> TYPE: DNA
<213> ORGANISM: Artificial Sequence
<220> FEATURE:
<223> OTHER INFORMATION: Synthetic sequence

<400> SEQUENCE: 51
gggccatggt aaaatcttgg tttatttaat c                                    31

<210> SEQ ID NO 52
<211> LENGTH: 27
<212> TYPE: DNA
<213> ORGANISM: Artificial Sequence
<220> FEATURE:
<223> OTHER INFORMATION: Synthetic sequence

<400> SEQUENCE: 52
ggggctagct ctctctaaaa ttgcagt                                         27

<210> SEQ ID NO 53
<211> LENGTH: 18
<212> TYPE: DNA
<213> ORGANISM: Artificial Sequence
<220> FEATURE:
<223> OTHER INFORMATION: Synthetic sequence

<400> SEQUENCE: 53
gaatagcctc tccaccca                                                   18

<210> SEQ ID NO 54
<211> LENGTH: 51
<212> TYPE: DNA
<213> ORGANISM: Artificial Sequence
<220> FEATURE:
<223> OTHER INFORMATION: Synthetic sequence

<400> SEQUENCE: 54
cccgctagcc gtggacaccc cacttccact tgttgtcggg tttattctca t              51
```

<210> SEQ ID NO 55
<211> LENGTH: 51
<212> TYPE: DNA
<213> ORGANISM: Artificial Sequence
<220> FEATURE:
<223> OTHER INFORMATION: Synthetic sequence

<400> SEQUENCE: 55
cccgctagct ttgaatccta ctgaggcttt tgtttctgtt tgaggactca t       51

<210> SEQ ID NO 56
<211> LENGTH: 21
<212> TYPE: DNA
<213> ORGANISM: Artificial Sequence
<220> FEATURE:
<223> OTHER INFORMATION: Synthetic sequence

<400> SEQUENCE: 56
tcacctgccg aatcaactag c                                        21

<210> SEQ ID NO 57
<211> LENGTH: 20
<212> TYPE: DNA
<213> ORGANISM: Artificial Sequence
<220> FEATURE:
<223> OTHER INFORMATION: Synthetic sequence

<400> SEQUENCE: 57
gacttccctt gcctacattg                                          20

<210> SEQ ID NO 58
<211> LENGTH: 40
<212> TYPE: DNA
<213> ORGANISM: Artificial Sequence
<220> FEATURE:
<223> OTHER INFORMATION: Synthetic sequence

<400> SEQUENCE: 58
aaaccatggc accacaaaca gagagcccag aacgacgccc                    40

<210> SEQ ID NO 59
<211> LENGTH: 29
<212> TYPE: DNA
<213> ORGANISM: Artificial Sequence
<220> FEATURE:
<223> OTHER INFORMATION: Synthetic sequence

<400> SEQUENCE: 59
aaaatctaga tcatcagatc tcggtgacg                                29

<210> SEQ ID NO 60
<211> LENGTH: 40
<212> TYPE: DNA
<213> ORGANISM: Artificial Sequence
<220> FEATURE:
<223> OTHER INFORMATION: Synthetic sequence

<400> SEQUENCE: 60
ccatggctag cccagaaaga agaccggccg atattagacg                    40

<210> SEQ ID NO 61
<211> LENGTH: 40
<212> TYPE: DNA
<213> ORGANISM: Artificial Sequence
<220> FEATURE:
<223> OTHER INFORMATION: Synthetic sequence

<400> SEQUENCE: 61
gcatatcagc ttctgtagca cgtctaatat cggccggtct          40

<210> SEQ ID NO 62
<211> LENGTH: 40
<212> TYPE: DNA
<213> ORGANISM: Artificial Sequence
<220> FEATURE:
<223> OTHER INFORMATION: Synthetic sequence

<400> SEQUENCE: 62
tgctacagaa gctgatatgc cagcagtttg tacaatcgtt          40

<210> SEQ ID NO 63
<211> LENGTH: 40
<212> TYPE: DNA
<213> ORGANISM: Artificial Sequence
<220> FEATURE:
<223> OTHER INFORMATION: Synthetic sequence

<400> SEQUENCE: 63
cttgtttcta taatggtt aacgattgta caaactgctg          40

<210> SEQ ID NO 64
<211> LENGTH: 40
<212> TYPE: DNA
<213> ORGANISM: Artificial Sequence
<220> FEATURE:
<223> OTHER INFORMATION: Synthetic sequence

<400> SEQUENCE: 64
aaccattata tagaaacaag tacagtaaac tttagaactg          40

<210> SEQ ID NO 65
<211> LENGTH: 40
<212> TYPE: DNA
<213> ORGANISM: Artificial Sequence
<220> FEATURE:
<223> OTHER INFORMATION: Synthetic sequence

<400> SEQUENCE: 65
ttcttgaggt tcttgaggtt cagttctaaa gtttactgta          40

<210> SEQ ID NO 66
<211> LENGTH: 40
<212> TYPE: DNA
<213> ORGANISM: Artificial Sequence
<220> FEATURE:
<223> OTHER INFORMATION: Synthetic sequence

<400> SEQUENCE: 66
aacctcaaga acctcaagaa tggactgatg atctagtccg          40

<210> SEQ ID NO 67
<211> LENGTH: 40
<212> TYPE: DNA
<213> ORGANISM: Artificial Sequence
<220> FEATURE:
<223> OTHER INFORMATION: Synthetic sequence

<400> SEQUENCE: 67
aaggatagcg ctctcgtaga cggactagat catcagtcca          40

<210> SEQ ID NO 68

```
<211> LENGTH: 40
<212> TYPE: DNA
<213> ORGANISM: Artificial Sequence
<220> FEATURE:
<223> OTHER INFORMATION: Synthetic sequence

<400> SEQUENCE: 68
tctacgagag cgctatcctt ggcttgtagc agaagttgac                    40

<210> SEQ ID NO 69
<211> LENGTH: 40
<212> TYPE: DNA
<213> ORGANISM: Artificial Sequence
<220> FEATURE:
<223> OTHER INFORMATION: Synthetic sequence

<400> SEQUENCE: 69
gcgataccag ctacttcacc gtcaacttct gctacaagcc                    40

<210> SEQ ID NO 70
<211> LENGTH: 40
<212> TYPE: DNA
<213> ORGANISM: Artificial Sequence
<220> FEATURE:
<223> OTHER INFORMATION: Synthetic sequence

<400> SEQUENCE: 70
ggtgaagtag ctggtatcgc atatgcgggc ccttggaagg                    40

<210> SEQ ID NO 71
<211> LENGTH: 40
<212> TYPE: DNA
<213> ORGANISM: Artificial Sequence
<220> FEATURE:
<223> OTHER INFORMATION: Synthetic sequence

<400> SEQUENCE: 71
ccaatcatat gcatttcttg ccttccaagg gcccgcatat                    40

<210> SEQ ID NO 72
<211> LENGTH: 40
<212> TYPE: DNA
<213> ORGANISM: Artificial Sequence
<220> FEATURE:
<223> OTHER INFORMATION: Synthetic sequence

<400> SEQUENCE: 72
caagaaatgc atatgattgg acagctgaat caactgttta                    40

<210> SEQ ID NO 73
<211> LENGTH: 40
<212> TYPE: DNA
<213> ORGANISM: Artificial Sequence
<220> FEATURE:
<223> OTHER INFORMATION: Synthetic sequence

<400> SEQUENCE: 73
gttgatgacg tggtgaaacg taaacagttg attcagctgt                    40

<210> SEQ ID NO 74
<211> LENGTH: 40
<212> TYPE: DNA
<213> ORGANISM: Artificial Sequence
<220> FEATURE:
<223> OTHER INFORMATION: Synthetic sequence

<400> SEQUENCE: 74
```
cgtttcacca cgtcatcaac gtacaggact tggttctact                           40

<210> SEQ ID NO 75
<211> LENGTH: 40
<212> TYPE: DNA
<213> ORGANISM: Artificial Sequence
<220> FEATURE:
<223> OTHER INFORMATION: Synthetic sequence

<400> SEQUENCE: 75
ttcagtagat gtgtatatag agtagaacca agtcctgtac                           40

<210> SEQ ID NO 76
<211> LENGTH: 40
<212> TYPE: DNA
<213> ORGANISM: Artificial Sequence
<220> FEATURE:
<223> OTHER INFORMATION: Synthetic sequence

<400> SEQUENCE: 76
ctatatacac atctactgaa atctttggag gcacaaggtt                           40

<210> SEQ ID NO 77
<211> LENGTH: 40
<212> TYPE: DNA
<213> ORGANISM: Artificial Sequence
<220> FEATURE:
<223> OTHER INFORMATION: Synthetic sequence

<400> SEQUENCE: 77
aacagctaca acactcttaa aaccttgtgc ctccaaagat                           40

<210> SEQ ID NO 78
<211> LENGTH: 40
<212> TYPE: DNA
<213> ORGANISM: Artificial Sequence
<220> FEATURE:
<223> OTHER INFORMATION: Synthetic sequence

<400> SEQUENCE: 78
ttaagagtgt tgtagctgtt ataggattgc ctaatgatcc                           40

<210> SEQ ID NO 79
<211> LENGTH: 40
<212> TYPE: DNA
<213> ORGANISM: Artificial Sequence
<220> FEATURE:
<223> OTHER INFORMATION: Synthetic sequence

<400> SEQUENCE: 79
cttcatgcat gcgtacactt ggatcattag gcaatcctat                           40

<210> SEQ ID NO 80
<211> LENGTH: 40
<212> TYPE: DNA
<213> ORGANISM: Artificial Sequence
<220> FEATURE:
<223> OTHER INFORMATION: Synthetic sequence

<400> SEQUENCE: 80
aagtgtacgc atgcatgaag ctctaggata tgctccaaga                           40

<210> SEQ ID NO 81
<211> LENGTH: 40
<212> TYPE: DNA

```
<213> ORGANISM: Artificial Sequence
<220> FEATURE:
<223> OTHER INFORMATION: Synthetic sequence

<400> SEQUENCE: 81
cctgcagccc tcaacatacc tcttggagca tatcctagag                              40

<210> SEQ ID NO 82
<211> LENGTH: 40
<212> TYPE: DNA
<213> ORGANISM: Artificial Sequence
<220> FEATURE:
<223> OTHER INFORMATION: Synthetic sequence

<400> SEQUENCE: 82
ggtatgttga gggctgcagg tttcaaacat ggaaactggc                              40

<210> SEQ ID NO 83
<211> LENGTH: 40
<212> TYPE: DNA
<213> ORGANISM: Artificial Sequence
<220> FEATURE:
<223> OTHER INFORMATION: Synthetic sequence

<400> SEQUENCE: 83
ttgccaaaaa cctacatcat gccagtttcc atgtttgaaa                              40

<210> SEQ ID NO 84
<211> LENGTH: 40
<212> TYPE: DNA
<213> ORGANISM: Artificial Sequence
<220> FEATURE:
<223> OTHER INFORMATION: Synthetic sequence

<400> SEQUENCE: 84
atgatgtagg tttttggcaa cttgatttca gtctaccagt                              40

<210> SEQ ID NO 85
<211> LENGTH: 40
<212> TYPE: DNA
<213> ORGANISM: Artificial Sequence
<220> FEATURE:
<223> OTHER INFORMATION: Synthetic sequence

<400> SEQUENCE: 85
gtagaactgg acgaggaggt actggtagac tgaaatcaag                              40

<210> SEQ ID NO 86
<211> LENGTH: 40
<212> TYPE: DNA
<213> ORGANISM: Artificial Sequence
<220> FEATURE:
<223> OTHER INFORMATION: Synthetic sequence

<400> SEQUENCE: 86
acctcctcgt ccagttctac cagttactga gatctgatga                              40

<210> SEQ ID NO 87
<211> LENGTH: 26
<212> TYPE: DNA
<213> ORGANISM: Artificial Sequence
<220> FEATURE:
<223> OTHER INFORMATION: Synthetic sequence

<400> SEQUENCE: 87
tctagatcat cagatctcag taactg                                             26
```

<210> SEQ ID NO 88
<211> LENGTH: 56
<212> TYPE: DNA
<213> ORGANISM: Artificial Sequence
<220> FEATURE:
<223> OTHER INFORMATION: Synthetic sequence

<400> SEQUENCE: 88
gtgggcaaag aacttgttga aggaaaattg gagctagtag aaggtcttaa agtcgc                56

<210> SEQ ID NO 89
<211> LENGTH: 64
<212> TYPE: DNA
<213> ORGANISM: Artificial Sequence
<220> FEATURE:
<223> OTHER INFORMATION: Synthetic sequence

<400> SEQUENCE: 89
catggcgact ttaagacctt ctactagctc caatttcct tcaacaagtt ctttgcccac           60
tacc                                                                        64

<210> SEQ ID NO 90
<211> LENGTH: 40
<212> TYPE: DNA
<213> ORGANISM: Artificial Sequence
<220> FEATURE:
<223> OTHER INFORMATION: Synthetic sequence

<400> SEQUENCE: 90
ggccatgggg gctagcgaag cggtgatcgc cgaagtatcg                                 40

<210> SEQ ID NO 91
<211> LENGTH: 40
<212> TYPE: DNA
<213> ORGANISM: Artificial Sequence
<220> FEATURE:
<223> OTHER INFORMATION: Synthetic sequence

<400> SEQUENCE: 91
cgaattctag acattatttg cccactacct tggtgatctc                                 40

<210> SEQ ID NO 92
<211> LENGTH: 51
<212> TYPE: DNA
<213> ORGANISM: Artificial Sequence
<220> FEATURE:
<223> OTHER INFORMATION: Synthetic sequence

<400> SEQUENCE: 92
ccggatccaa ggagatataa caccatggct agtaaaggag aagaactttt c                    51

<210> SEQ ID NO 93
<211> LENGTH: 28
<212> TYPE: DNA
<213> ORGANISM: Artificial Sequence
<220> FEATURE:
<223> OTHER INFORMATION: Synthetic sequence

<400> SEQUENCE: 93
gtgttggcca aggaacaggt agttttcc                                              28

<210> SEQ ID NO 94
<211> LENGTH: 44
<212> TYPE: DNA

```
<213> ORGANISM: Artificial Sequence
<220> FEATURE:
<223> OTHER INFORMATION: Synthetic sequence

<400> SEQUENCE: 94 catggggct agcgaacaaa aactcatttc tgaagaagac ttgc                    44

<210> SEQ ID NO 95
<211> LENGTH: 44
<212> TYPE: DNA
<213> ORGANISM: Artificial Sequence
<220> FEATURE:
<223> OTHER INFORMATION: Synthetic sequence

<400> SEQUENCE: 95
ctaggcaagt cttcttcaga aatgagtttt tgttcgctag cccc                   44

<210> SEQ ID NO 96
<211> LENGTH: 41
<212> TYPE: DNA
<213> ORGANISM: Artificial Sequence
<220> FEATURE:
<223> OTHER INFORMATION: Synthetic sequence

<400> SEQUENCE: 96
gtgggcaaag aacttgcagt tgaaggaaaa ttggaggtcg c                      41

<210> SEQ ID NO 97
<211> LENGTH: 49
<212> TYPE: DNA
<213> ORGANISM: Artificial Sequence
<220> FEATURE:
<223> OTHER INFORMATION: Synthetic sequence

<400> SEQUENCE: 97
catggcgacc tccaattttc cttcaactgc aagttctttg cccactacc              49

<210> SEQ ID NO 98
<211> LENGTH: 22
<212> TYPE: DNA
<213> ORGANISM: Artificial Sequence
<220> FEATURE:
<223> OTHER INFORMATION: Synthetic sequence

<400> SEQUENCE: 98
atggatgaac tatacaaata ag                                           22

<210> SEQ ID NO 99
<211> LENGTH: 17
<212> TYPE: DNA
<213> ORGANISM: Artificial Sequence
<220> FEATURE:
<223> OTHER INFORMATION: Synthetic sequence

<400> SEQUENCE: 99
gctcctatag tgtgacg                                                 17

<210> SEQ ID NO 100
<211> LENGTH: 22
<212> TYPE: DNA
<213> ORGANISM: Artificial Sequence
<220> FEATURE:
<223> OTHER INFORMATION: Synthetic sequence

<400> SEQUENCE: 100
actacctctg atagttgagt cg                                           22
```

-continued

<210> SEQ ID NO 101
<211> LENGTH: 20
<212> TYPE: DNA
<213> ORGANISM: Artificial Sequence
<220> FEATURE:
<223> OTHER INFORMATION: Synthetic sequence

<400> SEQUENCE: 101
agaggttaat cgtactctgg                                                    20

<210> SEQ ID NO 102
<211> LENGTH: 24
<212> TYPE: DNA
<213> ORGANISM: Artificial Sequence
<220> FEATURE:
<223> OTHER INFORMATION: Synthetic sequence

<400> SEQUENCE: 102
ggctccgcag tggatggcgg cctg                                               24

<210> SEQ ID NO 103
<211> LENGTH: 22
<212> TYPE: DNA
<213> ORGANISM: Artificial Sequence
<220> FEATURE:
<223> OTHER INFORMATION: Synthetic sequence

<400> SEQUENCE: 103
gggctgatac tgggccggca gg                                                 22

<210> SEQ ID NO 104
<211> LENGTH: 16
<212> TYPE: PRT
<213> ORGANISM: Artificial Sequence
<220> FEATURE:
<223> OTHER INFORMATION: Synthetic sequence

<400> SEQUENCE: 104

Glu Leu Val Glu Gly Lys Leu Glu Leu Val Glu Gly Leu Lys Val Ala
 1               5                  10                  15

<210> SEQ ID NO 105
<211> LENGTH: 11
<212> TYPE: PRT
<213> ORGANISM: Artificial Sequence
<220> FEATURE:
<223> OTHER INFORMATION: Synthetic sequence

<400> SEQUENCE: 105

Glu Leu Ala Val Glu Gly Lys Leu Glu Val Ala
 1               5                  10

<210> SEQ ID NO 106
<211> LENGTH: 10
<212> TYPE: PRT
<213> ORGANISM: Artificial Sequence
<220> FEATURE:
<223> OTHER INFORMATION: Synthetic sequence

<400> SEQUENCE: 106

Glu Gln Lys Leu Ile Ser Glu Glu Asp Leu
 1               5                  10

<210> SEQ ID NO 107
<211> LENGTH: 10

```
<212> TYPE: DNA
<213> ORGANISM: Artificial Sequence
<220> FEATURE:
<223> OTHER INFORMATION: Synthetic sequence

<400> SEQUENCE: 107
gctctagagc                                                              10

<210> SEQ ID NO 108
<211> LENGTH: 117
<212> TYPE: RNA
<213> ORGANISM: tabacum

<400> SEQUENCE: 108
accgcccguc acacuauggg agcuggccau gcccgaaguc guuaccuuaa ccgcaaggag        60
ggggaugccg acuggaguga agucguaaca agguagccgu acuggaaggu gcggcug         117

<210> SEQ ID NO 109
<211> LENGTH: 26
<212> TYPE: RNA
<213> ORGANISM: Artificial Sequence
<220> FEATURE:
<223> OTHER INFORMATION: Synthetic Sequence

<400> SEQUENCE: 109
ugccgaaggc agggcuagug acugga                                            26

<210> SEQ ID NO 110
<211> LENGTH: 26
<212> TYPE: RNA
<213> ORGANISM: Artificial Sequence
<220> FEATURE:
<223> OTHER INFORMATION: Snythetic Sequence

<400> SEQUENCE: 110
uuaccacuuu gugauucaug acuggg                                            26

<210> SEQ ID NO 111
<211> LENGTH: 50
<212> TYPE: RNA
<213> ORGANISM: Artificial Sequence
<220> FEATURE:
<223> OTHER INFORMATION: Snythetic Sequence

<400> SEQUENCE: 111
augagaauca auccuacuac uucgguucu ggguuucca cgcuugaaaa                     50

<210> SEQ ID NO 112
<211> LENGTH: 48
<212> TYPE: RNA
<213> ORGANISM: Artificial Sequence
<220> FEATURE:
<223> OTHER INFORMATION: Snythetic Sequence

<400> SEQUENCE: 112
augagaauaa acccgacaac aaguggaagu gggugucca cggcuagc                     48

<210> SEQ ID NO 113
<211> LENGTH: 50
<212> TYPE: RNA
<213> ORGANISM: Artificial Sequence
<220> FEATURE:
<223> OTHER INFORMATION: Snythetic Sequence

<400> SEQUENCE: 113
```

```
augccuauug uguuccaaa agucccuuuc cgaaguccug gagaggaaga          50

<210> SEQ ID NO 114
<211> LENGTH: 50
<212> TYPE: RNA
<213> ORGANISM: Artificial Sequence
<220> FEATURE:
<223> OTHER INFORMATION: Snythetic Sequence

<400> SEQUENCE: 114
augucaccac aaacagagac uaaagcaagu guuggauuca aagcuggugu          50

<210> SEQ ID NO 115
<211> LENGTH: 48
<212> TYPE: RNA
<213> ORGANISM: Artificial Sequence
<220> FEATURE:
<223> OTHER INFORMATION: Snythetic Sequence

<400> SEQUENCE: 115
augaguccuc agacagaaac aaaagccuca guaggauuca aagcuagc            48

<210> SEQ ID NO 116
<211> LENGTH: 58
<212> TYPE: RNA
<213> ORGANISM: Artificial Sequence
<220> FEATURE:
<223> OTHER INFORMATION: Snythetic Sequence

<400> SEQUENCE: 116
guauuuccau ggguuugccu ugguaucgug uucauaccgu uguauugaau gaucccgg  58

<210> SEQ ID NO 117
<211> LENGTH: 51
<212> TYPE: RNA
<213> ORGANISM: Artificial Sequence
<220> FEATURE:
<223> OTHER INFORMATION: Snythetic Sequence

<400> SEQUENCE: 117
caugacugca auuuagaga gacgcgaaag cgaaagccua uggggucgcu u          51

<210> SEQ ID NO 118
<211> LENGTH: 50
<212> TYPE: RNA
<213> ORGANISM: Artificial Sequence
<220> FEATURE:
<223> OTHER INFORMATION: Snythetic Sequence

<400> SEQUENCE: 118
auggcuagca ugacuggugg acagcaaaug ggucgcggau ccggcugcua          50

<210> SEQ ID NO 119
<211> LENGTH: 30
<212> TYPE: RNA
<213> ORGANISM: Artificial Sequence
<220> FEATURE:
<223> OTHER INFORMATION: Snythetic Sequence

<400> SEQUENCE: 119
auggcaagca ugacuggugg acaggcuagc                                30

<210> SEQ ID NO 120
<211> LENGTH: 30
<212> TYPE: RNA
<213> ORGANISM: Artificial Sequence
```

```
<220> FEATURE:
<223> OTHER INFORMATION: Snythetic Sequence

<400> SEQUENCE: 120
auggcaauca cuagcccugc cuuggcuagc                              30

<210> SEQ ID NO 121
<211> LENGTH: 34
<212> TYPE: RNA
<213> ORGANISM: Artificial Sequence
<220> FEATURE:
<223> OTHER INFORMATION: Snythetic Sequence

<400> SEQUENCE: 121
acauaugcgu agcauugaac aagauggauu gcau                         34

<210> SEQ ID NO 122
<211> LENGTH: 14
<212> TYPE: PRT
<213> ORGANISM: Artificial Sequence
<220> FEATURE:
<223> OTHER INFORMATION: Snythetic Sequence

<400> SEQUENCE: 122

Met Ser Pro Gln Thr Glu Thr Lys Ala Ser Val Gly Phe Lys
 1               5                   10

<210> SEQ ID NO 123
<211> LENGTH: 42
<212> TYPE: RNA
<213> ORGANISM: Artificial Sequence
<220> FEATURE:
<223> OTHER INFORMATION: Snythetic Sequence

<400> SEQUENCE: 123
auggcaagca ugacuggugg acaggcuagc auugaacaag au                42

<210> SEQ ID NO 124
<211> LENGTH: 14
<212> TYPE: PRT
<213> ORGANISM: Artificial Sequence
<220> FEATURE:
<223> OTHER INFORMATION: Snythetic Sequence

<400> SEQUENCE: 124

Met Ala Ser Met Thr Gly Gly Gln Ala Ser Ile Glu Gln Asp
 1               5                   10

<210> SEQ ID NO 125
<211> LENGTH: 42
<212> TYPE: RNA
<213> ORGANISM: Artificial Sequence
<220> FEATURE:
<223> OTHER INFORMATION: Snythetic Sequence

<400> SEQUENCE: 125
auggcaauca cuagcccugc cuuggcuagc auugaacaag au                42

<210> SEQ ID NO 126
<211> LENGTH: 14
<212> TYPE: PRT
<213> ORGANISM: Artificial Sequence
<220> FEATURE:
<223> OTHER INFORMATION: Snythetic Sequence

<400> SEQUENCE: 126
```

Met Ala Ile Thr Ser Pro Ala Leu Ala Ser Ile Glu Gln Asp
1               5                   10

<210> SEQ ID NO 127
<211> LENGTH: 42
<212> TYPE: RNA
<213> ORGANISM: Artificial Sequence
<220> FEATURE:
<223> OTHER INFORMATION: Snythetic Sequence

<400> SEQUENCE: 127
auggcuagca uugaacaaga uggauugcac gcagguucuc cg            42

<210> SEQ ID NO 128
<211> LENGTH: 14
<212> TYPE: PRT
<213> ORGANISM: Artificial Sequence
<220> FEATURE:
<223> OTHER INFORMATION: Snythetic Sequence

<400> SEQUENCE: 128

Met Ala Ser Ile Glu Gln Asp Gly Leu His Ala Gly Ser Pro
1               5                   10

<210> SEQ ID NO 129
<211> LENGTH: 188
<212> TYPE: PRT
<213> ORGANISM: Artificial Sequence
<220> FEATURE:
<223> OTHER INFORMATION: Snythetic Sequence

<400> SEQUENCE: 129

Met Ala Pro Gln Thr Glu Ser Pro Glu Arg Arg Pro Ala Asp Ile Arg
1               5                   10                  15

Arg Ala Thr Glu Ala Asp Met Pro Ala Val Cys Thr Ile Val Asn His
                20                  25                  30

Tyr Ile Glu Thr Ser Thr Val Asn Phe Arg Thr Glu Pro Gln Glu Pro
            35                  40                  45

Gln Glu Trp Thr Asp Asp Leu Val Arg Leu Arg Glu Arg Tyr Pro Trp
        50                  55                  60

Leu Val Ala Glu Val Asp Gly Glu Val Ala Gly Ile Ala Tyr Ala Gly
65                  70                  75                  80

Pro Trp Lys Ala Arg Asn Ala Tyr Asp Trp Thr Ala Glu Ser Thr Val
                85                  90                  95

Tyr Val Ser Pro Arg His Gln Arg Thr Gly Leu Gly Ser Thr Leu Tyr
            100                 105                 110

Thr His Leu Leu Lys Ser Leu Glu Ala Gln Gly Phe Lys Ser Val Val
        115                 120                 125

Ala Val Ile Gly Leu Pro Asn Asp Pro Ser Val Arg Met His Glu Ala
    130                 135                 140

Leu Gly Tyr Ala Pro Arg Gly Met Leu Arg Ala Ala Gly Phe Lys His
145                 150                 155                 160

Gly Asn Trp His Asp Val Gly Phe Trp Gln Leu Asp Phe Ser Leu Pro
                165                 170                 175

Val Pro Pro Arg Pro Val Leu Pro Val Thr Glu Ile
            180                 185

<210> SEQ ID NO 130
<211> LENGTH: 184
<212> TYPE: PRT
<213> ORGANISM: Artificial Sequence

```
<220> FEATURE:
<223> OTHER INFORMATION: Snythetic Sequence

<400> SEQUENCE: 130

Met Ala Ser Pro Glu Arg Arg Pro Ala Asp Ile Arg Arg Ala Thr Glu
 1               5                  10                  15

Ala Asp Met Pro Ala Val Cys Thr Ile Val Asn His Tyr Ile Glu Thr
            20                  25                  30

Ser Thr Val Asn Phe Arg Thr Glu Pro Gln Glu Pro Gln Glu Trp Thr
             35                  40                  45

Asp Asp Leu Val Arg Leu Arg Glu Arg Tyr Pro Trp Leu Val Ala Glu
 50                  55                  60

Val Asp Gly Glu Val Ala Gly Ile Ala Tyr Ala Gly Pro Trp Lys Ala
65                   70                  75                  80

Arg Asn Ala Tyr Asp Trp Thr Ala Glu Ser Thr Val Tyr Val Ser Pro
                 85                  90                  95

Arg His Gln Arg Thr Gly Leu Gly Ser Thr Leu Tyr Thr His Leu Leu
                100                 105                 110

Lys Ser Leu Glu Ala Gln Gly Phe Lys Ser Val Val Ala Val Ile Gly
            115                 120                 125

Leu Pro Asn Asp Pro Ser Val Arg Met His Glu Ala Leu Gly Tyr Ala
        130                 135                 140

Pro Arg Gly Met Leu Arg Ala Ala Gly Phe Lys His Gly Asn Trp His
145                 150                 155                 160

Asp Val Gly Phe Trp Gln Leu Asp Phe Ser Leu Pro Val Pro Pro Arg
                165                 170                 175

Pro Val Leu Pro Val Thr Glu Ile
                180

<210> SEQ ID NO 131
<211> LENGTH: 65
<212> TYPE: DNA
<213> ORGANISM: Artificial Sequence
<220> FEATURE:
<223> OTHER INFORMATION: Synthetic sequence

<400> SEQUENCE: 131
ggtagtgggc aaagaacttg ttgaaggaaa attggagcta gtagaaggtc ttaaagtcgc      60
catgg                                                                 65

<210> SEQ ID NO 132
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 132

Met Arg Ile Asn Pro Thr Thr Ser Gly Ser Gly Val Ser Thr
 1               5                  10
```